(12) United States Patent
Allerton et al.

(10) Patent No.: US 6,949,577 B2
(45) Date of Patent: Sep. 27, 2005

(54) PHARMACEUTICALS

(75) Inventors: Charlotte Moira Norfor Allerton, Kent (GB); Julian Blagg, Kent (DE); Mark Edward Bunnage, Kent (GB); John Steele, Kent (GB)

(73) Assignee: Pfizer, Inc., Groton, CT (US)

( * ) Notice: Subject to any disclaimer, the term of this patent is extended or adjusted under 35 U.S.C. 154(b) by 0 days.

(21) Appl. No.: 10/390,305

(22) Filed: Mar. 17, 2003

(65) Prior Publication Data

US 2003/0236420 A1 Dec. 25, 2003

Related U.S. Application Data

(63) Continuation of application No. 09/932,826, filed on Aug. 17, 2001, now abandoned.
(60) Provisional application No. 60/232,498, filed on Sep. 13, 2000, and provisional application No. 60/260,606, filed on Jan. 9, 2001.

(51) Int. Cl.$^7$ .................. A61K 31/4164; C07D 233/64
(52) U.S. Cl. ..................................... 514/396; 548/340.1
(58) Field of Search ........................ 548/340.1; 514/396

(56) References Cited

U.S. PATENT DOCUMENTS 4,528,397 A * 7/1985 Shibamoto et al. ......... 514/400
4,743,614 A * 5/1988 Terano et al. ............... 514/400

* cited by examiner

*Primary Examiner*—Laura L. Stockton
(74) *Attorney, Agent, or Firm*—Daniel S. Kasten; Charles Ashbrook

(57) ABSTRACT

The present invention provides compounds of formula (I)

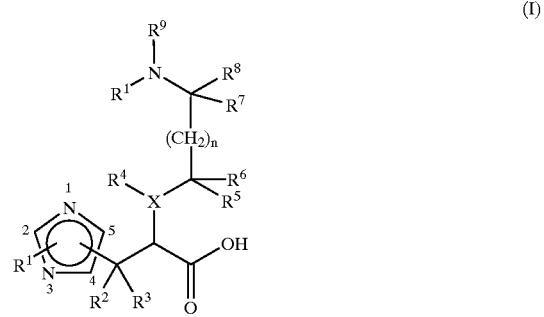

(I)

as well as the use of such compounds in pharmaceutical compositions and methods of treatment.

The compounds described herein represent a class of TAFIa inhibitors suitable for use in treating conditions such as thrombosis, atherosclerosis, adhesions, dermal scarring, cancer, fibrotic conditions, inflammatory diseases and those conditions which benefit from maintaining or enhancing bradykinin levels in the body.

24 Claims, 1 Drawing Sheet

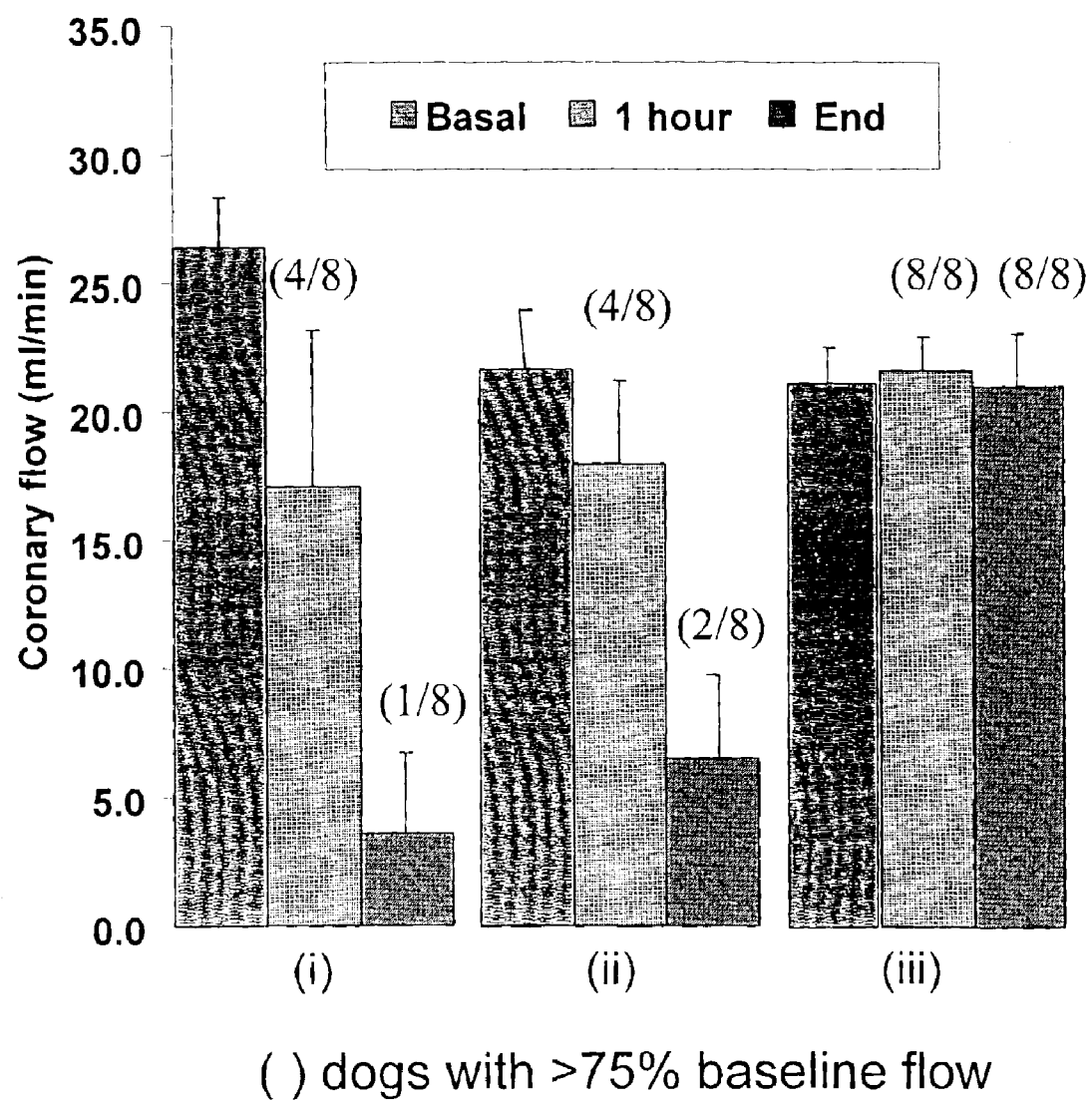

PHARMACEUTICALS

This application is a continuation of U.S. patent application Ser. No. 09/932,826 filed Aug. 17, 2001, now abandoned, which claims the benefit of U.S. Provisional Patent Application Nos. 60/232,498, filed Sep. 13, 2000 and 60/260,606 filed Jan. 9, 2001, all of which are incorporated herein by reference in their entirety.

FIELD OF INVENTION

The present invention describes a series of substituted imidazoles as TAFIa inhibitors, useful in the treatment of disease.

BACKGROUND

Thrombin Activatable Fibrinolysis Inhibitor, TAFI, is a 60 kDa glycoprotein found in human plasma. It is also known as procarboxypeptidase B, carboxypeptidase B, plasma carboxypeptidase B, carboxypeptidase U and carboxypeptidase R. It plays an intrinsic part in the blood coagulation process during which it is transformed into an activated form, TAFIa, whereupon it acts upon the fibrin matrix which comprises a developing blood clot to prevent its dissolution. Imbalances in the blood coagulation process are thought to be the origin of a large and disparate number of disease conditions which are linked by an unwanted build up of fibrin. The scale of fibrin build up is determined by the delicate equilibrium between two biochemical cascades in the human body; the coagulation and fibrinolysis cascades. These cascades are an integral part of maintaining hemostasis.

To maintain hemostasis in the blood, mammals have developed mechanisms to repair the body in the event of vascular injury. The injured blood vessel will constrict to reduce the blood flow to the area. Platelets will aggregate to reduce the loss of blood from the area followed by fibrinogen which polymerizes and forms a fibrin clot. This clot will cover the area of vascular damage preventing blood loss. Once the blood vessel has been repaired the clot will then dissolve. The coagulation cascade is responsible for the forming of a clot; the fibrinolysis cascade is responsible for the dissolution of the clot.

Studies have shown that these two processes are intrinsically linked through the generation of α-thrombin. α-Thrombin is the final product of the blood coagulation cascade and is responsible for the conversion of soluble plasma fibrinogen to an insoluble fibrin matrix. Polymerized fibrin provides a haemostatic plug which prevents blood loss from the site of vascular injury and provides a provisional matrix which enhances the subsequent repair process. In addition to mediating coagulation, α-thrombin also reduces the rate at which blood clots are broken down by the serine protease plasmin. The anti-fibrinolytic activity of α-thrombin results from its activation of TAFI. TAFI circulates in normal plasma at a concentration of about 75 nM in an inactive form. Thrombin converts the inactive zymogen to the active TAFI (TAFIa); a reaction that is augmented about 1250-fold by thrombomodulin. Once activated, TAFIa cleaves both C-terminal arginine and lysine residues from the developing fibrin clot. The removal of di-basic amino acids from the surface of the fibrin matrix attenuates clot lysis by inhibiting the binding of the key mediators of fibrinolysis: tissue plasminogen activator (tPA) and its substrate, plasminogen, which is the precursor of plasmin. Both tPA and plasminogen contain a structural motif called a kringle domain which binds tightly to C-terminal lysine residues. The removal of these binding sites prevents the formation of a ternary complex between tPA, plasminogen and fibrin and this inhibits the conversion of plasminogen to plasmin thus protecting the clot from rapid degradation.

It can be seen that if the equilibrium between coagulation and fibrinolysis is in favor of coagulation, then there will be a larger amount of fibrin present than normal. This makes it more likely that the subject will develop one or more of the conditions in which thrombus build up is implicated. By the use of a TAFIa inhibitor, TAFIa will not be able to act upon a developing fibrin clot as described above to inhibit-fibrinolysis of the clot. Therefore, a TAFIa inibitor should serve to enhance the fibrinolysis cascade.

The use of TAFI inhibitors to treat certain conditions is known in the art. Whilst the use of TAFIa inhibitors to treat such conditions is unknown, certain weak, non-specific TAFIa inhibitors have been identified.

U.S. Pat. No. 5,993,815 teaches the use of a peptide that binds to the TAFI zymogen, inhibiting activation of the TAFI zymogen, to treat those disorders where a C-terminal lysine or arginine is cleaved from an intact peptide. The disorders include arthritis, sepsis, thrombosis, strokes, deep vein thrombosis and myocardial infarctions. The peptide used is an antibody or a functionally active fragment. The peptide should be used in an amount to promote fibrinolysis in vivo.

McKay et al, *Biochemistry*, 17, 401 (1978), discloses the testing of a number of compounds as competitive inhibitors of bovine carboxypeptidase B of pancreatic origin. Inhibition was measured by the inhibitor's efficiency in protecting the active centre tyrosine and glutamic acid of bovine carboxypeptidase B from irreversible alkylation by bromoacetyl-D-arginine or bromoacetamidobutylguanidine. It is suggested that such inhibitors could act as bradykinin potentiators.

Bovine enzymes of pancreatic origin are very different to those found in human plasma, so one would not expect inhibitors of one to inhibit the other. Moreover, such inhibitors are directed towards a very different utility. Accordingly the above reference contains no teaching of TAFIa inhibitors or their utility.

Redlitz et al, *J. Clin. Invest.*, 96, 2534 (1995), teaches the involvement of plasma carboxypeptidase B (pCPB, or TAFI) in the formation of clots. The lysis of blood clots was followed in the absence and presence of pCPB, whereupon it was found that the presence of pCPB slowed clot lysis. To confirm that pCPB was responsible, two control reactions were run: (1) where the lysis experiment was repeated in the presence of pCPB and a carboxypeptidase inhibitor, PCI; and (2) where the lysis reaction was conducted in the presence of plasma from which pCPB was removed. In both cases lysis proceeded uninhibited.

Boffa et al, *J. Biol. Chem.*, 273, 2127 (1998), compares plasma and recombinant TAFI and TAFIa with respect to glycosylation, activation, thermal stability and enzymatic properties. Inhibition constants for three competitive inhibitors were determined: ε-aminocaproic acid (ε-ACA), 2-guanidinoethyl-mercaptosuccinic acid (GEMSA) and potato carboxypeptidase inhibitor (PCI).

There are large numbers of carboxypeptidases characterized by cleaving the C-terminal amino acid from a peptide. They may be divided into acidic, neutral or basic, depending on the type of amino acid they cleave. Basic carboxypeptidases cleave arginine, lysine and histidine. TAFIa is a specific subset of basic carboxypeptidases. In terms of the present invention, the inhibitors disclosed above by Redlitz, et al. and Boffa, et al., are too weak, non-specific or otherwise unsuitable to be considered as suitable TAFIa inhibitors for therapeutic application. Further, while the role of TAFIa in clot lysis is explained, there is no suggestion that TAFIa inhibitors can be used to treat disease.

PCT publication WO00/66550 discusses a broad class of compounds useful as inhibitors of carboxypeptidase U. Inhibitors of carboxypeptidase U are postulated to facilitate fibrinolysis and thus the compounds are taught as useful in the treatment of thrombotic conditions. Although details of a suitable assay are given, there is no data to support this assertion.

PCT publication WO00/66152 discloses formulations containing a carboxypeptidase U inhibitor and a thrombin inhibitor. Suitable carboxypeptidase U inhibitors are those of PCT publication WO00/66550. The formulations are taught as being useful primarily in treating thrombotic conditions.

SUMMARY OF THE INVENTION

In the present invention, it has been discovered that the active site on TAFIa, that is responsible for reacting with a developing clot, is small; therefore, it can be blocked by a small molecule (e.g., a compound having a molecular weight of less than about 1000, preferably less than about 500). Accordingly, one aspect of the present invention provides a potent class of TAFIa inhibitors based on this discovery.

In one embodiment of the present invention, a preferred set of TAFIa inhibitors is provided that are represented by Formula (I)

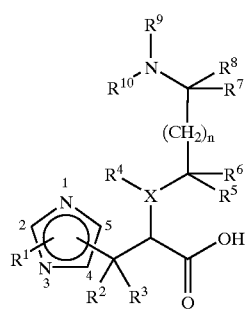

(I)

wherein
X is N or CH;
n is 0, 1, 2 or 3;
$R^1$ is hydrogen, heterocycle, aromatic heterocycle, aryl, $(C_1\text{-}C_6)$alkyl, $(C_1\text{-}C_6)$alkenyl, or $(C_1\text{-}C_6)$alkynyl, where each of $(C_1\text{-}C_6)$alkyl, $(C_1\text{-}C_6)$alkenyl, and $(C_1\text{-}C_6)$alkynyl are optionally substituted by $(C_3\text{-}C_7)$cycloalkyl, aryl, aromatic heterocycle, heterocycle, $OR^{11}$, $NR^{11}R^{12}$, $S(O)_pR^{11}$, $OC(O)R^{11}$, $CO_2R^{11}$, $CONR^{11}R^{12}$, $SO_2NR^{11}R^{12}$, halo or $NHSO_2R^{11}$, where p is 0, 1 or 2, and $R^{11}$ and $R^{12}$ are each independently hydrogen, $(C_1\text{-}C_6)$alkyl, or when forming a $NR^{11}R^{12}$ moiety, $R^{11}$ and $R^{12}$ is optionally taken together to form a $(C_2\text{-}C_6)$alkylene linkage;
$R^2$ and $R^3$ are each independently hydrogen, $(C_1\text{-}C_6)$alkyl optionally substituted by $OR^{11}$ or halo, or $R^2$ and $R^3$ taken together form a $(C_2\text{-}C_6)$alkylene linkage;
$R^4$ is hydrogen, $(C_1\text{-}C_6)$alkyl optionally substituted by $(C_3\text{-}C_7)$cycloalkyl, aryl, $OR^{11}$, halo or $R^{11}$, or $R^4$ taken together with $R^{10}$ forms a $(C_1\text{-}C_4)$alkylene linkage optionally substituted by halo, $OR^{11}$, or $R^{11}$, where $R^{11}$ is hydrogen or $(C_1\text{-}C_6)$alkyl;

$R^5$ and $R^6$ are each independently hydrogen, aryl, $(C_1\text{-}C_6)$alkyl optionally substituted by $(C_3\text{-}C_7)$cycloalkyl, aromatic heterocycle, heterocycle, aryl, $OR^{11}$, $R^{11}$ or halo, $R^5$ or $R^6$ taken together with $R^{10}$ forms a $(C_1\text{-}C_3)$alkylene optionally substituted by $OR^{11}$, halo, $R^{11}$, or aryl, or $R^5$ and $R^6$ taken together form a $(C_2\text{-}C_6)$alkylene linkage, where $R^{11}$ is hydrogen or $(C_1\text{-}C_6)$alkyl;
$R^7$ and $R^8$ are each independently hydrogen, $(C_1\text{-}C_6)$alkyl optionally substituted by $OR^{11}$, halo, aryl, or $R^{11}$, or $R^7$ and $R^8$ taken together form a $(C_2\text{-}C_6)$alkylene linkage, where $R^{11}$ is hydrogen or $(C_1\text{-}C_6)$alkyl; and
$R^9$ and $R^{10}$ are each independently hydrogen, $C(NR^{11})NR^{11}R^{12}$, $(C_1\text{-}C_6)$alkyl optionally substituted by $OR^{11}$, halo, aryl or $R^{11}$, where $R^{11}$ and $R^{12}$ are each independently hydrogen or $(C_1\text{-}C_6)$alkyl, or $R^9$ and $R^{10}$ taken together form a $(C_2\text{-}C_6)$alkylene linkage;
a pharmaceutically acceptable salt thereof, a solvate of the compound or the salt, or a prodrug of the compound, salt, or solvate.

In another embodiment of the present invention, there is provided the stereoisomers of formula (I)—compounds of formulae (IA) and (IB):

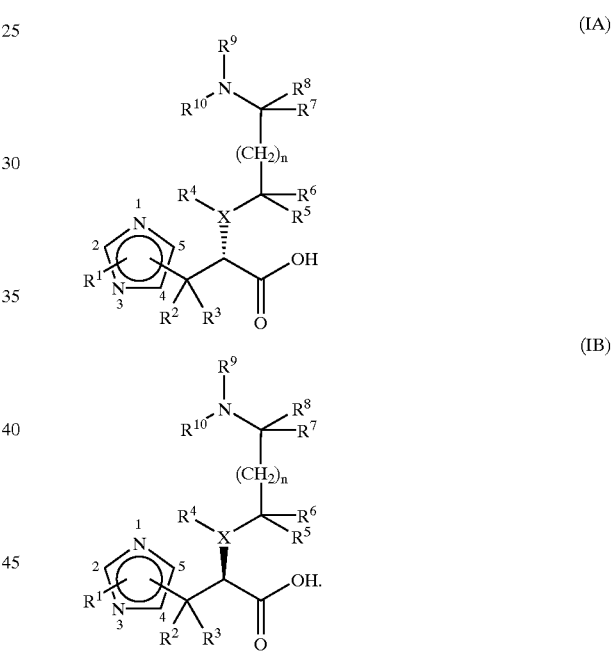

The preferred isomeric form is the compound of formula (IA). The compounds of the present invention may also be incorporated into a pharmaceutical composition which comprises a compound of the present invention and a pharmaceutically acceptable excipient, diluent or carrier.

In yet another embodiment of the present invention, compounds of formula (XXIII) and (XXIV) are provided

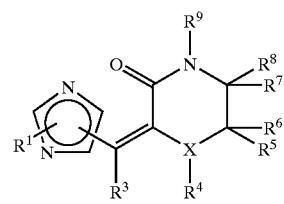

(XXIII)

(XXIV)

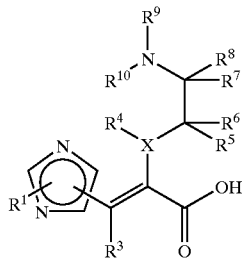

where $R^1$, $R^3$, $R^5$, $R^6$, $R^7$, $R^8$ and $R^{10}$ are as described above, $R^4$ is hydrogen, n is 0, X is CH, and $R^9$ is as described above or an appropriate nitrogen protecting group (N-Pg).

In another embodiment of the present invention, there is provided a process for producing the compounds of formula (IA) and (IB) comprising the steps of:
(i) hydrolyzing a compound of formula (XXIII) to produce a compound of (XXIV) wherein $R^{10}$ is hydrogen;
(ii) hydrogenating said compound from step (a) to produce an enantiomeric mix of compounds of formula (IA) and formula (IB);
(iii) resolving said enantiomeric mix to separate said compound of formula (IA) from said compound of formula (IB); and
(iv) optionally removing said nitrogen-protecting group when $R^9$ is a nitrogen-protecting group.

Another aspect of the present invention is the use of a TAFIa inhibitor for the treatment or prevention of a condition selected from thrombosis, atherosclerosis, adhesions, dermal scarring, cancer, fibrotic conditions, inflammatory diseases and those conditions which benefit from maintaining or enhancing bradykinin levels in the body. Preferred TAFIa inhibitors are those compounds of formula (I) above.

In yet another aspect of the present invention, there is provided a method of treating or preventing a condition selected from the group consisting of thrombosis, atherosclerosis, adhesions, dermal scarring, cancer, fibrotic conditions, inflammatory diseases and those conditions which benefit from maintaining or enhancing bradykinin levels in the body comprising the step of administering a therapeutically effective amount of a TAFIa inhibitor, a pharmaceutically acceptable salt of the inhibitor, a solvate of the inhibitor or salt, or a prodrug of the inhibitor, salt, or solvate to a patient in need of such treatment. Preferred TAFIa inhibitors are those compounds of formula (I) above, prodrugs thereof, pharmaceutically acceptable salts of the compounds or prodrugs, and solvates of the compounds, prodrugs or salts. Thrombosis includes conditions such as myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events following intervention surgery.

Another aspect of the present invention includes an intravascular device comprising a coating which comprises a TAFIa or TAFI inhibitor. A preferred TAFIa inhibitor is a compound of the present invention described above.

In yet another aspect of the present invention, there is provided a pharmaceutical kit which comprises a first pharmaceutical composition comprising a compound of the present invention and a pharmaceutically acceptable diluent or carrier; (ii) a second pharmaceutical composition comprising an antithrombotic agent and a pharmaceutically acceptable excipient, diluent or carrier; and (iii) a container.

Definitions

As used herein, the term "alkyl" is defined as a hydrocarbon radical of the general formula $C_nH_{2n+1}$. The alkane radical may be straight or branched. For example, the term "$(C_1-C_4)$alkyl" refers to a monovalent, straight, or branched aliphatic group containing 1 to 4 carbon atoms (e.g., methyl, ethyl, n-propyl, i-propyl, n-butyl, i-butyl, s-butyl, t-butyl, and other constitutional isomers containing 1 to 4 carbon atoms (including stereoisomers). The alkane radical may be unsubstituted or substituted with one or more substituents. For example, a "halo-substituted alkyl" refers to an alkyl group substituted with one or more halogen atoms (e.g., fluoromethyl, difluoromethyl, trifluoromethyl, perfluoroethyl, chloromethyl, bromomethyl, and the like). Similarly, the alkyl portion of an alkylene, alkenyl or alkynyl group has the same meaning as alkyl defined above and the halo-substituted alkyl portion of a halo-substituted alkenyl or alkynyl group has the same meaning as halo-substituted alkyl defined above. An alkylene may be straight or branched, e.g., a $C_2$ alkylene may be an ethylene or methylmethylene, a $C_3$ alkylene may be a propylene, 2-methylethylene, 1-methylethylene, or ethylmethylene, and so on.

The term "cycloalkyl" is defined herein as nonaromatic rings that are either partially or fully hydrogenated. For example, a partially or fully saturated $(C_3-C_6)$cycloalkyl includes groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, and the like.

The term "aryl" is defined herein as a 6–14 membered, substituted or unsubstituted, aromatic carbocyclic ring. Suitable substituents include $R^{11}$, halo, $OR^{11}$, $NR^{11}R^{12}$, $NR^{11}CO_2R^{12}$, $CO_2R^{11}$, $NR^{11}SO_2R^{12}$, CN, haloalkyl, O(haloalkyl), $S(O)_pR^{11}$ (p=0, 1, or 2), $OC(O)R^{11}$, $SO_2NR^{11}R^{12}$, or $C(O)NR^{11}R^{12}$, where $R^{11}$ and $R^{12}$ are as defined above. Aryl moieties include groups such as phenyl, naphthyl, indenyl, anthryl and phenanthryl groups.

The term "aromatic heterocycle" is defined herein as a 5 to 7 membered substituted or unsubstituted aromatic ring containing 1 to 3 heteroatoms each independently selected from O, S and N. Suitable substituents include $OR^{11}$, $NR^{11}R^{12}$, $CO_2R^{11}$, $NR^{11}CO_2R^{12}$, $R^{11}$, halo, CN, haloalkyl, O(haloalkyl), $S(O)_pR^{11}$(p=0, 1, or 2), $OC(O)R^{11}$, $NR^{11}SO_2R^{12}$, $SO_2NR^{11}R^{12}$, or $C(O)NR^{11}R^{12}$, where $R^{11}$ and $R^{12}$ are as defined above.

The term "heterocycle" is defined herein as a saturated or partially saturated, substituted or unsubstituted, 3–8 membered ring containing from 1–3 heteroatoms, each independently selected from O, S and N. Suitable substituents include $OR^{11}$, $NR^{11}R^{12}$, $CO_2R^{11}$, $NR^{11}CO_2R^{12}$, $R^{11}$, halo, CN, haloalkyl, O(haloalkyl), $S(O)_pR^{11}$ (p=0, 1, or 2), $OC(O)R^{11}$, $NR^{11}SO_2R^{12}$, $SO_2NR^{11}R^{12}$, or $C(O)NR^{11}R^{12}$, where $R^{11}$ and $R^{12}$ are as defined above.

Compounds of formula (I) also include zwitterions, pharmaceutically acceptable salts, prodrugs, solvates and polymorphs thereof.

The term "halo" refers to fluoro, chloro, bromo and iodo groups.

The term "substituted" means that a hydrogen atom on a molecule has been replaced with a different atom or molecule. The atom or molecule replacing the hydrogen atom is denoted as a "substituent." The term substituted specifically envisions and allows for substitutions that are common in the art. However, it is generally understood by those skilled in the art that the substituents should be selected so as to not adversely affect the pharmacological characteristics of the compound or adversely interfere with the use of the medicament.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative (e.g., prophylactic) and palliative treatment.

The term "compounds of the present invention" (unless specifically identified otherwise) refer to compounds of Formula (I), prodrugs thereof, pharmaceutically acceptable salts of the compounds and/or prodrugs, and hydrates or solvates of the compounds, salts, and/or prodrugs, as well as, all stereoisomers (including diastereoisomers and enantiomers), tautomers and isotopically labeled compounds. The compounds of the present invention may exist in unsolvated as well as solvated forms with pharmaceutically acceptable solvents such as water, ethanol, and the like, and it is intended that the invention embrace both solvated and unsolvated forms.

BRIEF DESCRIPTION OF THE FIGURE

FIG. 1 provides a graphical representation comparing the effect of (i) aspirin and tPA, (ii) tPA, and (iii) TAFIa inhibitor and tPA on blood flow post-reperfusion.

DETAILED DESCRIPTION

There are very great advantages in using a TAFIa inhibitor over a TAFI inhibitor. TAFI is activated to TAFIa by reaction with thrombin. A TAFI inhibitor must prevent these two large peptides coming together to react at the appropriate site. To date, only large peptides have been described which can interfere with this reaction (U.S. Pat. No. 5,993,815). However, it has been discovered that the active site on TAFIa that is responsible for reacting with a developing clot is small; therefore, it can be blocked by a small molecule (e.g., a compound having a molecular weight of less than about 1000, preferably less than about 500). It is a great advantage to have a low molecular weight compound as the 'active' in a medicament. They are associated with oral bioavailability and patients usually prefer oral formulations. Further there is the potential for peptide therapeutics to induce an immune response. This is unlikely to be an issue with a small molecule. Small molecules are also generally more stable in plasma and thus have a greater duration of action. This is unlikely to be the case with large molecules, particularly peptides. For these reasons a TAFIa inhibitor is preferred, in particular, those TAFIa inhibitors having formula (I):

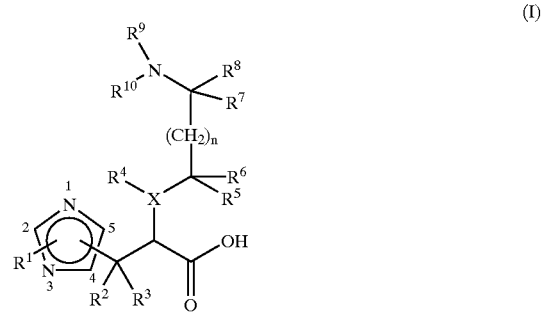

(I)

where n, X, $R^1$, $R^2$, $R^3$, $R^4$, $R^5$, $R^6$, $R^7$, $R^8$, $R^9$, and $R^{10}$ are as defined above.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent. Pharmaceutically acceptable salts of the compounds of the formula (I) include both the acid addition and the base salts thereof. Suitable acid addition salts are formed from acids which form non-toxic salts, e.g., hydrochloride, hydrobromide, hydroiodide, sulfate, bisulfate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts e.g., sodium, potassium, aluminium, calcium, magnesium, zinc and diethanolamine salts. For a review on suitable salts, see, Berge, et al., *J. Pharm. Sci.*, 66, 1 (1977).

Pharmaceutically acceptable solvates of the compounds of the formula (I) include the hydrates thereof.

Also included within the scope of the compounds of the formula (I) are polymorphs thereof.

It will also be appreciated by those skilled in the art that the compounds of the present invention also include prodrugs thereof. Prodrugs include pharmaceutically acceptable derivatives of (I) wherein the functional groups explicitly recited above have been derivatized to provide compounds which can be converted to the parent compound in vivo. Such prodrugs are discussed in *Drugs of Today*, 1983, 19, 499–538 and *Annual Reports in Medicinal Chemistry*, 1975, Vol. 10, Ch 31, 306–326. Suitable prodrugs include compounds of formula (II) and (III).

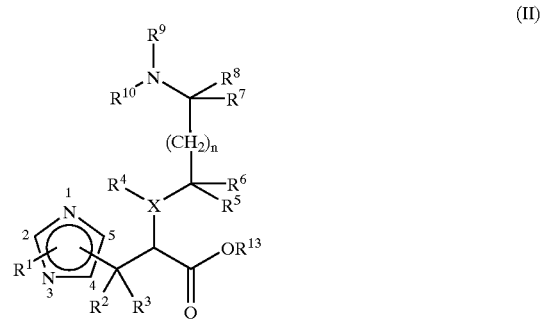

(II)

-continued (III)

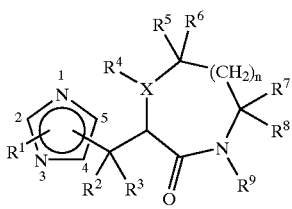

R¹, R², R³, R⁴, R⁵, R⁶, R⁷, R⁸, n and X are as described above, R⁹ and R¹⁰ are as described above or in addition one or both groups may be a suitable nitrogen-protecting group (N-Pg) and R¹³ is an appropriate oxygen-protecting group or carboxy-protecting group (O-Pg). The term "protecting group" or "Pg" refers to a substituent that is commonly employed to block or protect a particular functionality while reacting other functional groups on the compound. For example, a "nitrogen-protecting group" is a substituent attached to a nitrogen that blocks or protects the nitrogen functionality in the compound. Suitable nitrogen-protecting groups include carbamates (e.g., t-butoxycarbonyl (BOC) and benzyl groups). A "carboxy-protecting group" refers to a substituent of the carboxy group that blocks or protects the carboxy functionality. "Oxygen-protecting groups" or "carboxy-protecting groups" are also well-known to those skilled in the art and include allyl, aryl and alkyl groups optionally substituted by aryl or $(C_3-C_7)$cycloalkyl. Preferred oxygen-protecting groups include benzyl, pivaloyloxymethyl (POM) and $(C_1-C_6)$alkyl. For a general description of protecting groups and their use, see T. W. Greene, *Protective Groups in Organic Synthesis*, John Wiley & Sons, New York, 1991.

Compounds of formula (I) contain one or more asymmetric carbon atoms; therefore, the compounds of formula (I) may exist in two or more stereoisomeric forms. Where compounds of formula (I) contain an alkenyl or alkenylene group, cis (E) and trans (Z) isomerism may also occur. The present invention includes the individual stereoisomers of the compounds of formula (I) and, where appropriate, the individual tautomeric forms thereof, together with mixtures thereof.

Preferred compounds of formula (I) include those that possess the stereochemistry shown below.

(IA)

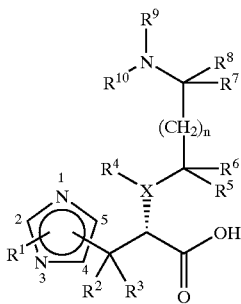

-continued (IB)

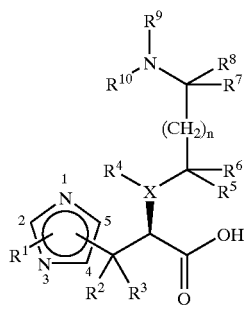

Those compounds of formula (IA) are preferred.

Separation of diastereoisomers (e.g., cis and trans isomers) may be achieved by conventional techniques, e.g. by fractional crystallization, chromatography or high pressure liquid chromatograph (HPLC) of a stereoisomeric mixture of a compound of the formula (IA) or (IB) or a suitable salt or derivative thereof. An individual enantiomer of a compound of formulae (IA) or (IB) may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. For a more detailed description, see *Enantiomers, Racemates and Resolutions* J. Jacques and A. Collet, published by Wiley, NY,. 1981; and *Handbook of Chiral Chemicals*, chapter 8, Eds D. Ager and M. Dekker, ISBN:0-8247-1058-4.

Preferred compounds of formula (I) include those where the imidazole is substituted at any position by R¹ and at the C2 or C4 positions by the amino acid fragment.

Particularly preferred are those compounds of formula (I) where R¹ is attached to N1 of the imidazole moiety so as to give the (1,4)-disubstituted imidazole and compounds of formula (I) where R¹ is attached to C4 of the imidazole so as to give the (2,4)-disubstituted imidazole.

Preferably R¹ is an aryl group, a $(C_3-C_7)$ cycloalkyl group, a $(C_1-C_6)$alkenyl group or a $(C_1-C_6)$alkyl group, the alkyl or alkenyl groups may be optionally substituted by one or more groups selected from $(C_3-C_7)$cycloalkyl, heterocycle, aromatic heterocycle, $OR^{11}$, $CO_2R^{11}$, $NR^{11}SO_2R^{12}$, $NR^{11}R^{12}$, $C(O)NR^{11}R^{12}$, $SO_2NR^{11}R^{12}$, halo, $OC(O)R^{11}$, aryl or $S(O)_p$ $R^{11}$, where p is 0–2, and $R^{11}$ and $R^{12}$ are as defined earlier. More preferably, R¹ is an aryl group, $(C_1-C_6)$alkenyl group, or a $(C_1-C_6)$alkyl group optionally substituted by one or more groups selected from $CO_2R^{11}$, $OR^{11}$, aryl, $(C_3-C_7)$ cycloalkyl, $NHSO_2R^{11}$, halo, or aromatic heterocycle, where $R^{11}$ is as defined earlier. Yet more preferably, R¹ is a $CF_3$ group or a $(C_1-C_6)$alkyl group optionally substituted by a $(C_3-C_7)$cycloalkyl group, aromatic heterocycle, $OR^{11}$, $CO_2R^{11}$, $NR^{11}SO_2R^{12}$ or aryl, where $R^{11}$ and $R^{12}$ are as defined earlier. Even more preferably R¹ is $(C_1-C_6)$alkyl optionally substituted by a $(C_3-C_4)$cycloalkyl group or aryl group. Most preferably R¹ is $(C_1-C_3)$alkyl.

Preferably, R² and R³ are each independently selected from hydrogen and $(C_1-C_6)$alkyl. Most preferably R² and R³ are each hydrogen.

Preferably, R⁴ is hydrogen, $(C_1-C_6)$alkyl optionally substituted by phenyl, or taken together with R¹⁰ forms a $(C_2-C_3)$alkylene linkage. More preferably, R⁴ is hydrogen, $(C_1-C_3)$alkyl, or taken together with R¹⁰ forms a $(C_2-C_3)$ alkylene. Yet more preferably, R⁴ is hydrogen or taken together with R¹⁰ forms a $(C_2-C_3)$alkylene linkage. Most preferably, R⁴ is hydrogen.

Preferably, $R^5$ and $R^6$ are each independently hydrogen, $(C_1\text{-}C_6)$alkyl optionally substituted by phenyl, or $R^5$ taken together with $R^{10}$ forms a $(C_1\text{-}C_3)$alkylene linkage. More preferably, $R^5$ and $R^6$ are each independently hydrogen, $(C_1\text{-}C_3)$alkyl optionally substituted by phenyl, or $R^5$ taken together with $R^{10}$ forms a $C_2$ alkylene linkage. Yet more preferably, $R^5$ and $R^6$ are each independently hydrogen or $(C_1\text{-}C_3)$alkyl. Most preferably, $R^5$ and $R^6$ are each hydrogen.

Preferably, $R^7$ and $R^8$ are each independently hydrogen or $(C_1\text{-}C_6)$alkyl optionally substituted by phenyl. More preferably, $R^7$ and $R^8$ are each independently hydrogen or $(C_1\text{-}C_6)$alkyl. Yet more preferably, $R^7$ and $R^8$ are each independently hydrogen or $(C_1\text{-}C_3)$alkyl. Even more preferred are compounds of the present invention where $R^7$ and $R^8$ are each independently hydrogen or $CH_3$. Most preferably, $R^7$ and $R^8$ are each hydrogen.

Preferably, $R^9$ and $R^{10}$ are each independently hydrogen, $C(NH)NH_2$, $(C_1\text{-}C_6)$alkyl, or $R^{10}$ taken together with $R^4$ forms a $(C_2\text{-}C_3)$alkylene linkage. More preferably, $R^9$ and $R^{10}$ are each independently hydrogen, $(C_1\text{-}C_3)$alkyl, or $R^{10}$ taken together with $R^4$ forms a $(C_2\text{-}C_3)$alkylene linkage. Yet more preferably, $R^9$ and $R^{10}$ are each independently hydrogen or $(C_1\text{-}C_3)$alkyl. Most preferred are those compounds of the present invention where $R^9$ and $R^{10}$ are each hydrogen.

Preferably, $R^{11}$ and $R^{12}$ are each independently hydrogen or $(C_1\text{-}C_3)$alkyl. More preferably, $R^{11}$ and $R^{12}$ are each independently hydrogen or $CH_3$.

X is preferably CH.

n is preferably 0 or 1. Most preferably, n is 0.

"Aryl" is preferably phenyl optionally substituted by 1–3 groups selected from $R^{11}$ halo, $OR^{11}$, $NR^{11}R^{12}$, $CO_2R^{11}$, $NHSO_2R^{11}$, CN and haloalkyl, where $R^{11}$ and $R^{12}$ are as defined earlier. Most preferably, aryl is phenyl.

Preferably, "aromatic heterocycle" is a 5 to 6 membered ring containing from 1 to 3 heteroatoms (each independently selected from O, S and N) optionally substituted by 1–3 groups selected from $OR^{11}$, $NR^{11}R^{12}$, $CO_2R^{11}$, $NR^{11}CO_2R^{12}$, $R^{11}$, halo, CN, haloalkyl, O(haloalkyl), $S(O)_p R^{11}$, $OC(O)R^{11}$, $NR^{11}SO_2R^{12}$, $SO_2NR^{11}R^{12}$, and $C(O)NR^{11}R^{12}$, where $R^{11}$ and $R^{12}$ are as defined earlier. More preferably, the aromatic heterocycle moiety is a 5 to 6 membered ring containing from 1 to 2 heteroatoms (each independently selected from O, S and N) optionally substituted by 1–3 groups selected from $OR^{11}$, $NR^{11}R^{12}$, $CO_2R^{11}$, $NR^{11}CO_2R^{12}$, $R^{11}$, halo, CN, haloalkyl, O(haloalkyl), $S(O)_p R^{11}$, $OC(O)R^{11}$, $NR^{11}SO_2R^{12}$, $SO_2NR^{11}R^{12}$, and $C(O)NR^{11}R^{12}$, where $R^{11}$ and $R^{12}$ are as defined earlier. Most preferably, the aromatic heterocycle moiety is a 5 to 6 membered ring containing from 1 to 2 heteroatoms (each independently selected from O, S and N).

Preferably, "heterocycle" is a 3–8 membered, saturated or partially saturated, ring containing from 1–2 heteroatoms (each independently selected from O, S and N) optionally substituted by 1–3 groups selected from $OR^{11}$, $NR^{11}R^{12}$, $CO_2R^{11}$, $NR^{11}CO_2R^{12}$, $R^{11}$, halo, CN, haloalkyl, O(haloalkyl), $S(O)_p R^{11}$, $OC(O)R^{11}$, $NR^{11}SO_2R^{12}$, $SO_2NR^{11}R^{12}$, $C(O)NR^{11}R^{12}$, where $R^{11}$ and $R^{12}$ are as defined earlier. More preferably, the heterocycle moiety is a 5–6 membered, saturated or partially saturated, ring containing from 1–2 heteroatoms (each independently selected from O, S and N) optionally substituted by 1–3 groups selected from $OR^{11}$, $NR^{11}R^{12}$, $CO_2R^{11}$, $NR^{11}CO_2R^{12}$, $R^{11}$, halo, CN, haloalkyl, O(haloalkyl), $S(O)_p R^{11}$, $OC(O)R^{11}$, $NR^{11}SO_2R^{12}$, $SO_2NR^{11}R^{12}$, and $C(O)NR^{11}R^{12}$, where $R^{11}$ and $R^{12}$ are as defined earlier. Most preferably, the heterocycle moiety is a 5–6 membered, saturated or partially saturated, ring containing from 1–2 heteroatoms (each independently selected from O, S and N).

Preferred compounds of the present invention include:
(±)-5-Amino-2-[(1-n-propyl-1H-imidazol-4-yl)methyl]pentanoic acid (Example 2);
(+)-(2S)-5-Amino-2-[(1-n-butyl-1H-imidazol-4-yl)methyl]pentanoic acid (Example 5);
(+)-(2S)-5-Amino-2-[(1-n-propyl-1H-imidazol-4-yl)methyl]pentanoic acid (Example 7);
(+)-(2S)-5-Amino-2-(1H-imidazol-4-ylmethyl)pentanoic acid (Example 9);
(2S)-2-[(2-Aminoethyl)amino]-3-(1-n-propyl-1H-imidazol-4-yl)propanoic acid (Example 25);
(2S)-2-[(2-Aminoethyl)amino]-3-(1-n-butyl-1H-imidazol-4-yl)propanoic acid (Example 26);
(2S)-2-[(2-Aminoethyl)amino]-3-(1-n-isobutyl-1H-imidazol-4-yl)propanoic acid (Example 29); and
(2S)-2-[(2-Aminoethyl)amino]-3-(1-n-isopentyl-1H-imidazol-4-yl)propanoic acid (Example 30).

A particularly preferred compound of the present invention is (+)-(2S)-5-amino-2-[(1-n-propyl-1H-imidazol-4-yl)methyl]pentanoic acid (Example 7)

The present invention also includes compounds of formula (XXIII) and (XXIV)

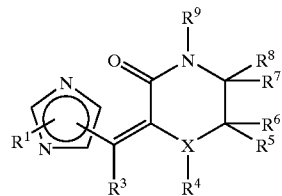

(XXIII)

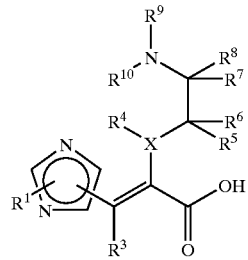

(XXIV)

where $R^1$, $R^3$, $R^5$, $R^6$, $R^7$, $R^8$ and $R^{10}$ are as described above, $R^4$ is hydrogen, n is 0, X is CH, and $R^9$ is as described above or is an appropriate nitrogen protecting group(N-Pg). Appropriate nitrogen-protecting groups include carbamates (e.g., BOC and benzyl groups). These compounds are useful intermediates in the synthesis of compounds of formula (I).

The invention further provides methods for the preparation of the compounds of the invention, which are described below and in the Examples and Preparations section. One skilled in the art will appreciate that the compounds of the invention could be made by methods other than those described herein, by adaptation of the methods described herein and/or adaptation of a plethora of methods known in the art. It is to be understood that the synthetic transformation methods specifically mentioned herein may be carried out in various different sequences to achieve an efficient synthesis of the desired substances. The skilled chemist will exercise his judgement and skill as to the most efficient sequence of reactions for synthesis of a given target substance.

It will also be apparent to one skilled in the art that sensitive functional groups may need to be protected and deprotected during synthesis of a substance of the invention. This may be achieved by conventional techniques, for example as described in *Protective Groups in Organic Synthesis* by T. W. Greene and P. G. M. Wuts, John Wiley and Sons Inc, 1991.

Compounds of formula (I) may be prepared by reacting a compound of formula (II) with a suitable reagent to remove the oxygen-protecting group.

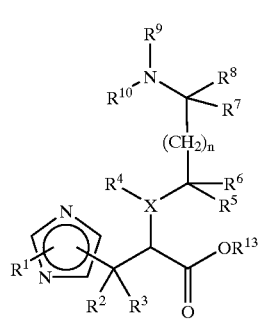

(II)

wherein $R^1$, $R^2$, $R^3$, $R^4$, $R^5$, $R^6$, $R^7$, $R^8$, $R^9$, $R^{10}$, n, and X are as described above. $R^{13}$ is an appropriate oxygen-protecting group (e.g., allyl groups or alkyl groups optionally substituted by aryl groups). Alternatively, one or both of $R^9$ and $R^{10}$ may be a suitable nitrogen-protecting group.

Suitable reagents and conditions to remove the protecting groups are well known to those skilled in the art. Suitable means for removing the protecting groups include hydrolysis and hydrogenation.

When $R^9$ and/or $R^{10}$ is a nitrogen-protecting group, it may be necessary to remove the nitrogen-protecting group after reaction of (II) with a suitable reagent to remove the oxygen-protecting group. Suitable nitrogen-protecting groups are well known to those skilled in the art, as are suitable conditions for their removal.

Compounds of formula (II), where $R^1$, $R^3$, $R^4$, $R^5$, $R^6$, $R^7$, $R^8$, $R^9$, $R^{10}$, $R^{13}$ and X are as described above and $R^2$ is hydrogen may be prepared from compounds of formula (V) and (VI) in accordance with the following reaction Scheme I.

Scheme I

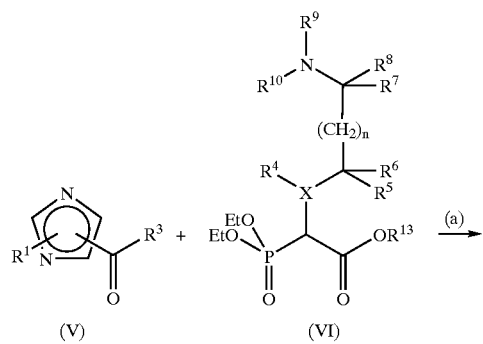

Compounds of formula (IV) may be formed by process step (a), a Wadsworth-Emmons reaction between compounds of formula (V) and (VI). This may be conducted under standard conditions, such as described in Org. Synth. Coll. Vol., 1988, 6, 358 and 1993, 8, 265. Suitable conditions include formation of the phosphonate anion with a suitable base such as NaH at 0° C., then reacting with 1 eq of the appropriate aldehyde at room temperature for 18 hours. A suitable solvent would be tetrahydrofuran.

Compounds of formula (II) may be formed by process step (b), a hydrogenation. This may be carried out by a method such as catalytic hydrogenation, e.g. 10% Pd/C at 4 atmospheres, in an alcoholic solvent (methanol or ethanol) at room temperature to 60° C. for between 4 and 72 hours; or by activated metal hydride reduction, e.g. 30 eq $NaBH_4$, 1.5 to 2.5 eq CuCl, in methanol, at room temperature for 2 hours. The process may also be conducted to give an asymmetric hydrogenation of the alkene bond. Such methods are well known to those skilled in the art and are discussed in *Asymmetric Synthetic Methodology*, chapter 9, Eds D. Ager and M. East, CRC Press, 1996, ISBN: 0-8493-8492-9.

Compounds of formula (V) are commercially available or may be prepared by a number of literature methods well known to those skilled in the art. See, e.g., the preparations described herein and G. Shapiro et al, *Heterocycles*, 1995, 41, 215; L. A. Reiter, *J. Org. Chem.*, 1987, 52, 2714; B. H. Lipshutz et al, *Tetrahedron Lett.* 1986, 27, 4095; F. Aldebbagh et al, *Tetrahedron Lett.*, 1997, 38 7937; and S. M. Abdelaal, *J. Het. Chem.* 1995, 32, 903.

Compounds of formula (VI) where $R^4$, $R^5$, $R^6$, $R^7$, $R^8$, $R^9$, $R^{10}$ and $R^{13}$ are as described above and X is CH, may be prepared in accordance with the following Scheme II.

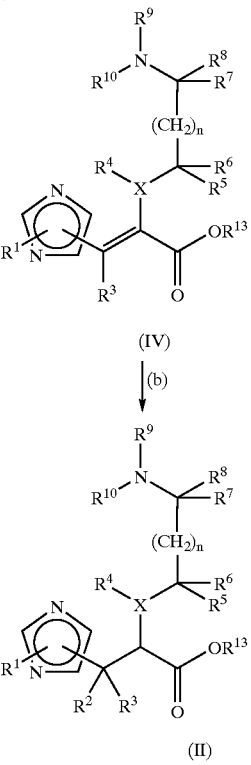

Scheme II

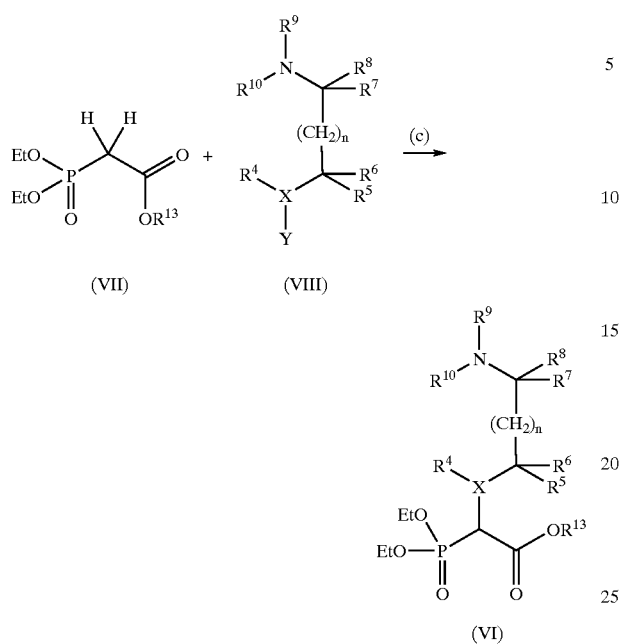

(VII)   (VIII)

(VI)

Compounds of formula (VI) may be prepared from the compounds of formula (VII) and (VIII) where Y is halo, under the conditions of process step (c), an alkylation reaction. This may be carried out under standard conditions, typically 1 eq of (VII) is treated with 1.1 eq of NaH, before reaction with (VIII), 18-crown-6 (cat) at reflux for 18 hours.

Compounds of formula (VI) where $R^5, R^6, R^7, R^8, R^9, R^{10}$ and $R^{13}$ are as described above, $R^4$ is a suitable nitrogen protecting group and X is N, may be prepared using the reaction scheme described above.

Compounds of formula (I) may also be prepared by treating a compound of formula (III) under the conditions of a lactam hydrolysis reaction. Suitable conditions include those of process step (d), a lactam hydrolysis. This may be conducted under standard conditions, typically basic conditions, e.g. aqueous LiOH in tetrahydrofuran at room temperature for 4–18 hours.

Compounds of formula (III) where $R^1, R^3, R^4, R^5, R^6, R^7, R^8, R^9, R^{13}$, X and Z are as described above and $R^2$ is hydrogen, may be prepared by the following process illustrated in Scheme III.

Scheme III

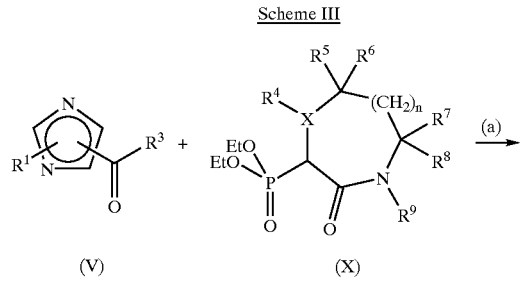

(V)   (X)

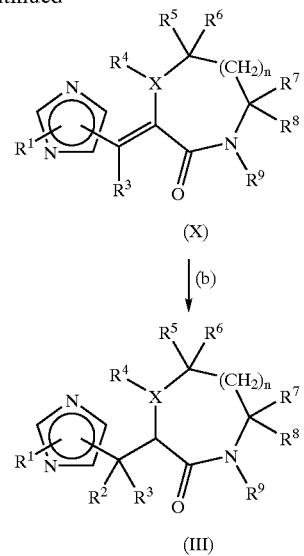

(X)

(III)

Compounds of formula (IX) may be prepared by reacting compounds of formula (V) and (X) under the conditions of process step (a) described above. Compounds of formula (III) may be prepared by reacting compounds of formula (IX) under the conditions of process step (b) described above.

Compounds of formula (X) where $R^4, R^5, R^6, R^7, R^8, R^9, R^{10}$ and $R^{13}$ are as described above, with the proviso $R^9$ and $R^{10}$ may not be linked and X is CH may be prepared from a compound of formula (XI) where Y is halo, in accordance with the following reaction Scheme IV.

Scheme IV

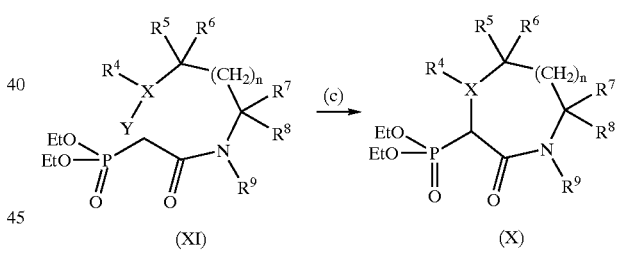

(XI)   (X)

Compounds of formula (X) may be prepared from compounds of formula (XI) under the conditions of process step (c) described above.

Compounds of formula (II) where $R^1, R^2, R^3, R^4, R^6, R^7, R^8, R^{10}$ and $R^{13}$ are as described above, $R^9$ is as above or is a suitable nitrogen-protecting group, X is N and $R^6$ is hydrogen may be prepared from a compounds of formula (XII) and (XIII), in accordance with the following reaction Scheme V.

Scheme V

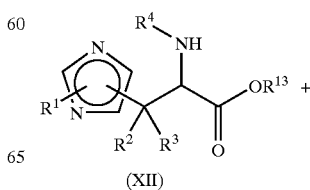

(XII)

-continued

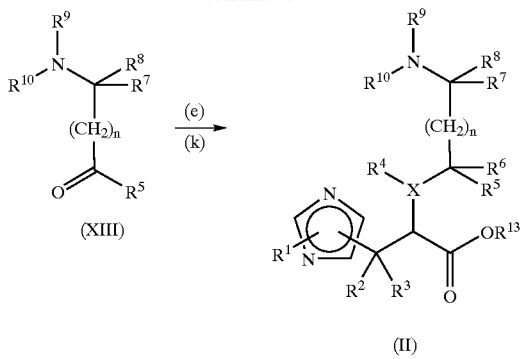

(II)

Compounds of formula (II) may be prepared by reacting compounds of formula (XII) and (XIII) under the conditions of process step (e), a reductive alkylation reaction, performed under standard conditions known to those skilled in the art. Suitable conditions would include reacting (XII) and (XIII) in the presence of sodium acetate and sodium cyanoborohydride.

Compounds of formula (II) wherein $R^9$ is H may be obtained from compounds of formulae (II) where $R^9$ is a suitable nitrogen-protecting group by optional process step (k), removal of a nitrogen-protecting group. Appropriate conditions for the removal of nitrogen-protecting groups are described in *Protective Groups in Organic Synthesis*, $2^{nd}$ edition, T. W. Greene and P. G. M. Wutz, Wiley-Interscience (1991).

For example, appropriate conditions for the removal of a BOC group is the treatment of the protected compound with 6N aqueous hydrochloric acid at room temperature at reflux temperature for between 1 and 3 hours.

For the removal of a benzyl protecting group, the protected compound is subjected to a dissolving metal reduction, e.g. Na, liq $NH_3$, $-78°$ C.

Compounds of formula (XIII) are commercially available or may be prepared by methods well known to one skilled in the art.

Compounds of formula (XII) above are commercially available. Alternatively where $R^1$, $R^3$, $R^4$ and $R^{13}$ are as described above, and $R^2$ is hydrogen, they may be made by the route disclosed in *Helv. Chim. Acta.*, 1994, 77, 1395 or as disclosed below in Scheme VI.

Scheme VI

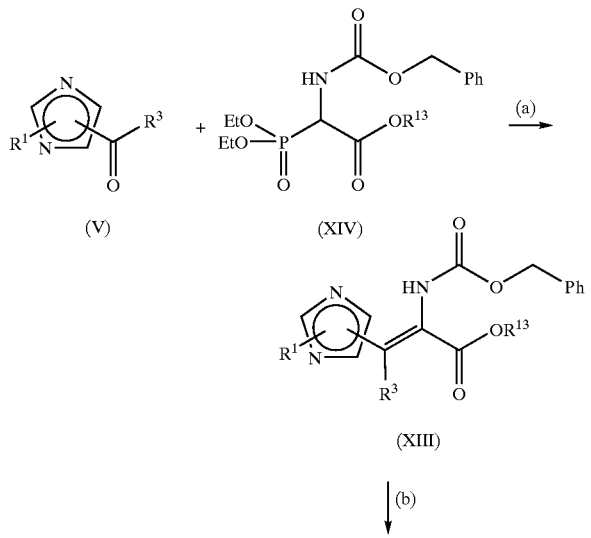

-continued

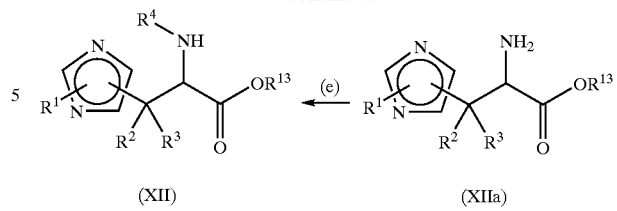

Compounds of formula (XII) may be prepared by reacting compounds of formula (V) and (XIV) under the conditions of process step (a) described above. Compounds of formula (XIIa) may be prepared by reacting compounds of formula (XIII) under the conditions of process step (b) described above. If a compound of formula (XII) is required where $R^4$ is not hydrogen, then compounds of formula (XII) may be prepared by reacting compounds of formula (XIIa) under the conditions of process step (e), described above.

Compounds of formula (XIIa) where $R^1$, $R^2$ and $R^3$, are as described above, with the proviso $R^2$ and $R^3$ are not linked and $R^{13}$ is methyl, may also be asymmetrically prepared from a compound of formula (XVI), where Y is halo, in accordance with the following reaction Scheme VII.

Scheme VII

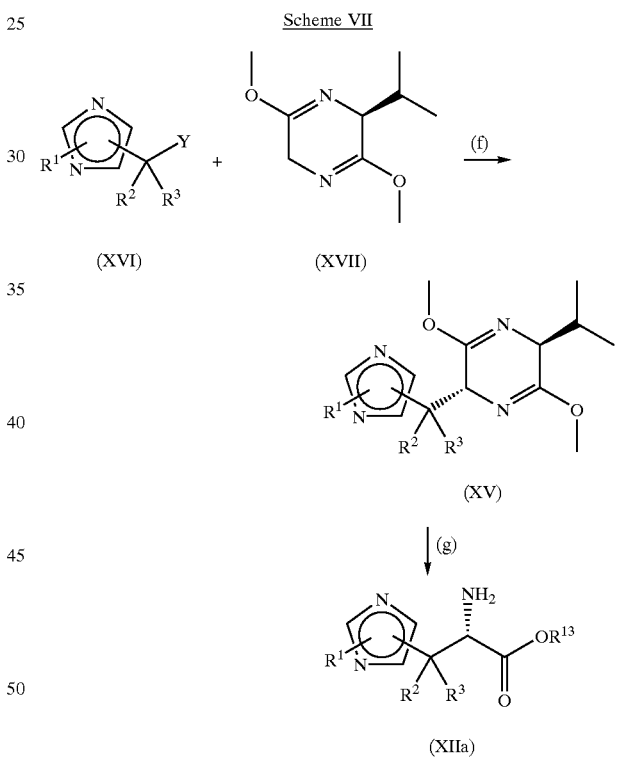

Compounds of formula (XV) may be prepared by reacting compounds of formula (XVII) and (XVI) under the conditions of process step (f) a Schollkopf asymmetric alkylation reaction comprising reaction of a halide with a suitable deprotonated Schollkopf chiral auxiliary (*Angew. Chem. Int. Ed. Engl.*, 1981, 20, 798). Suitable conditions are treating the Schollkopf auxiliary in tetrahydrofuran at $-78°$ C. with BuLi, followed by addition of (XVI) then 24 hours at room temperature. Compounds of formula (XIIa) may be prepared by reacting compounds of formula (XV) under the conditions of process step (g), a hydrolysis reaction, described in *Angew. Chem. Int. Ed. Engl.*, 1981, 20, 798. Suitable conditions are 5 eq of 0.25N aqueous hydrochloric acid at room temperature for 2 hours.

Compounds of formula (XII) may be obtained by methods well known to those skilled in the art or as exemplified in the examples. It should be noted that compounds of formula (XII) and intermediates thereto wherein $R^1$ is not H may be produced by coupling compounds of formula (XII) and intermediates thereto where $R^1$ is H, with an appropriate reagent containing $R^1$, where $R^1$ is as disclosed above.

Compounds of formula (II) where $R^1$, $R^2$, $R^3$, $R^4$, $R^5$, $R^6$, $R^7$, $R^8$, $R^9$, $R^{10}$ and $R^{13}$ are as described above and X is nitrogen may also be prepared from compounds of formula (XIX) and (XVIII) Where Y is halo by the method described in the following reaction Scheme VIII.

Scheme VIII

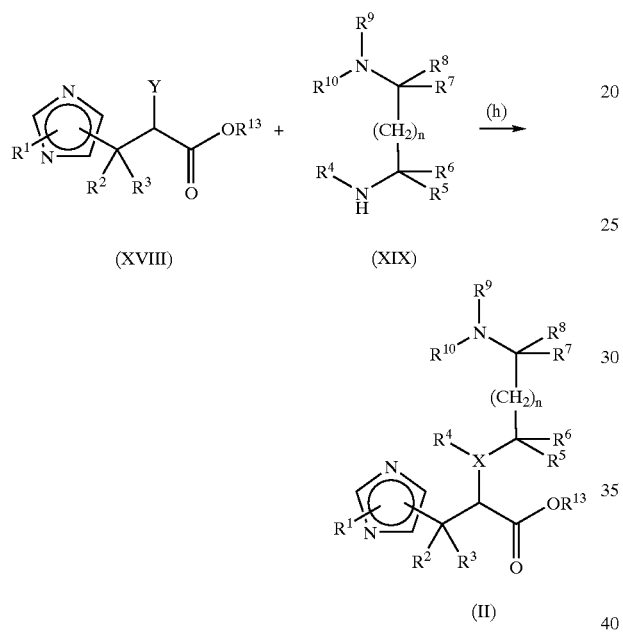

Compounds of formula (II) may be prepared by reacting compounds of formula (XVIII) and (XIX) under the conditions of process step (h) an alkylation reaction, reacting an excess of the amine with the halide. Suitable conditions are 6 eq of (XIX) and 1 eq of (XVIII) in acetonitrile at room temperature for 2 hours followed by 18 hours at reflux.

Compounds of formula (XIX) may be prepared by a number of literature routes, well known to one skilled in the art, as well as being commercially available.

Compounds of formula (XX) where $R^1$, $R^2$, $R^3$ and $R^{13}$ are as described above, with the proviso $R^2$ and $R^3$ are not linked, may be prepared by the method described in the following reaction Scheme IX.

Scheme IX

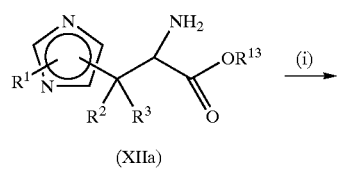

(XIIa)

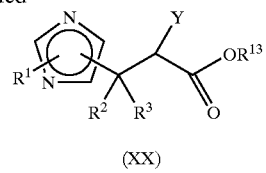

(XX)

Compounds of formula (XX) may be prepared by reacting compounds of formula (XIIa) under the conditions of process step (i) a diazotization/halogenation reaction, comprising conversion of the amine group to a diazo group, followed by reaction with a suitable halide, typically in situ. Suitable conditions are treating 1 eq of amine with 3.3 eq of $NaNO_2$ in concentrated hydrochloric acid:water (30:5) at $-5°$ C., then 17 hours at room temperature.

Compounds of formulae (IA) and (IB) where $R^1$, $R^3$, $R^5$, $R^6$, $R^7$ and $R^8$ are as described above, $R^2$, $R^4$ and $R^{10}$ are hydrogen, $R^9$ is as described above or is a suitable nitrogen-protecting group, n is 0 and X is CH may be prepared from compounds of formula (XXIII), both the E and Z isomers in accordance with the following Scheme X.

Scheme X

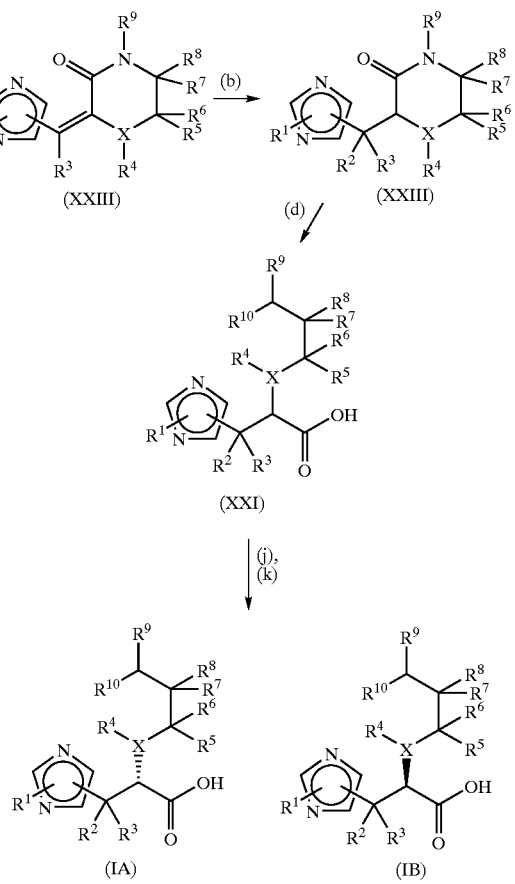

Compounds of formula (XXII) may be prepared from compounds of formula (XXIII), under the conditions of process step (b), as described above. Appropriate nitrogen protecting groups include carbamates, particularly BOC and benzyl groups. Process step (b) may also be conducted asymmetrically, using techniques known to those skilled in the art.

Compounds of formula (XXI) may be prepared from compounds of formula (XXII) under the conditions of process step (d), a lactam hydrolysis reaction which may be conducted under acidic or basic conditions as appropriate.

Compounds of formulae (IA) and (IB) may be prepared from compounds of formula (XXI) under the conditions of process step (j), resolution of the enantiomers, followed by optional process step (k), removal of the nitrogen-protecting group when $R^9$ is a nitrogen-protecting group.

In process step (j), individual enantiomers of a compound of the formulae (IA) or (IB) may be prepared by resolution, such as by HPLC of the corresponding racemate using a suitable chiral support or by fractional crystallization of the diastereoisomeric salts formed by reaction of the corresponding racemate with a suitable optically active acid or base, as appropriate. Reference is made herein to *Enantiomers, Racemates and Resolutions* J. Jacques and A. Collet, published by Wiley, NY, 1981; and *Handbook of Chiral Chemicals* chapter 8, Eds D. Ager and M. Dekker, ISBN:0-8247-1058-4.

Compounds of formulae (IA) or (IB) wherein $R^9$ is H may be obtained from compounds of formulae (IA) or (IB) where $R^9$ is a suitable nitrogen-protecting group by optional process step (k), removal of a nitrogen protecting group; appropriate conditions for the removal of nitrogen protecting groups $R^9$ are described in *Protective Groups in Organic Synthesis*, $2^{nd}$ edition, T. W. Greene and P. G. M. Wutz, Wiley-Interscience (1991). Appropriate conditions for removal of the BOC group entail the treatment of the protected compound with 6N aqueous hydrochloric acid at room temperature to reflux temp, for between 1 and 3 hours. The removal of the benzyl group is accomplished by dissolving metal reduction, e.g. Na, liq $NH_3$, $-78°$ C.

Compounds of formulae (IA) and (IB) where $R^1$, $R^3$, $R^5$, $R^6$, $R^7$, $R^8$ and X are as described above and $R^2$, $R^4$, and $R^{10}$ are hydrogen and $R^9$ is as described above or is an appropriate nitrogen-protecting group may also be prepared asymmetrically from compounds of formula (XXIII), where (XXIII) is either the E or Z isomer, in accordance with the reaction Scheme XI shown below.

Scheme XI

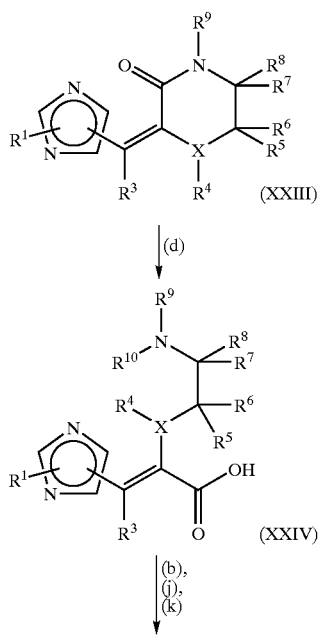

-continued

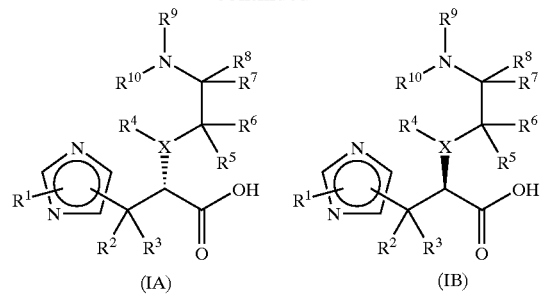

Compounds of formula (XXIV) may be prepared from compounds of formula (XXIII) under the conditions of process step (d), as described above.

Compounds of formula (IA) or (IB) may be prepared from compounds of formula (XXIV) under the conditions of process steps (b), a hydrogenation, (j), resolution of enantiomers and optionally, (k), removal of the nitrogen-protecting group (Pg) when $R^9$ is a nitrogen protecting group. Process steps (b), (j) and (k) are described above.

In an alternative embodiment, compounds of formula (IA) where $R^1$, $R^3$, $R^5$, $R^6$, $R^7$, $R^8$, $R^{10}$ and X are as described above, $R^2$ and $R^4$ are hydrogen and $R^9$ is as described above or may be an appropriate nitrogen protecting group, may also be prepared asymmetrically from compounds of formula (XXIV), where (XXIV) is either the E or Z isomer, in accordance with the reaction Scheme XII shown below.

Scheme XII

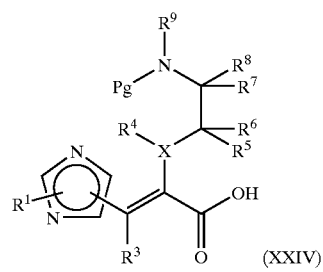

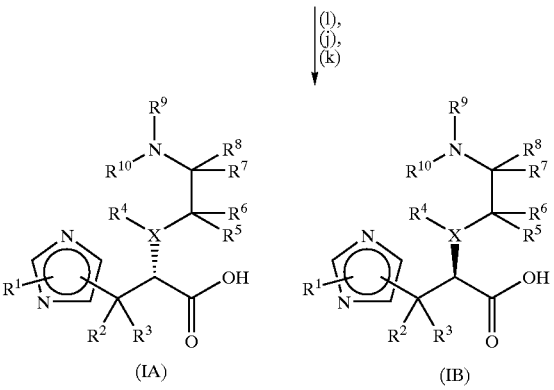

Compounds of formulae (IA) or (IB) may be prepared from compounds of formula (XXIV) under the conditions of process steps (I), an asymmetric hydrogenation, (j), resolution of the enantiomers and optionally (k), removal of the nitrogen-protecting group (Pg) when $R^9$ is a nitrogen-protecting group. Process step (j) is optional and is dependent upon the degree of enantiomeric selectivity obtained in step (l). Process step (j) may also be conducted in situ during process step (l). Process steps (j) and (k) are described above and are further exemplified in the examples.

The methods used to conduct process step (l) are well known to those skilled in the art and are discussed in *Asymmetric Synthetic Methodology*, chapter 9, Eds D. Ager and M. East, CRC Press, 1996, ISBN: 0-8493-8492-9, as well as being further exemplified in the examples.

Compounds of formula (XXIII) where $R^1$, $R^3$, $R^5$, $R^6$, $R^7$, $R^8$ and X are as described above and $R^9$ is as described above or a suitable nitrogen protecting group may be prepared from compounds of formula (V) and (XXVI) in accordance with the reaction Scheme XIII below.

Scheme XIII

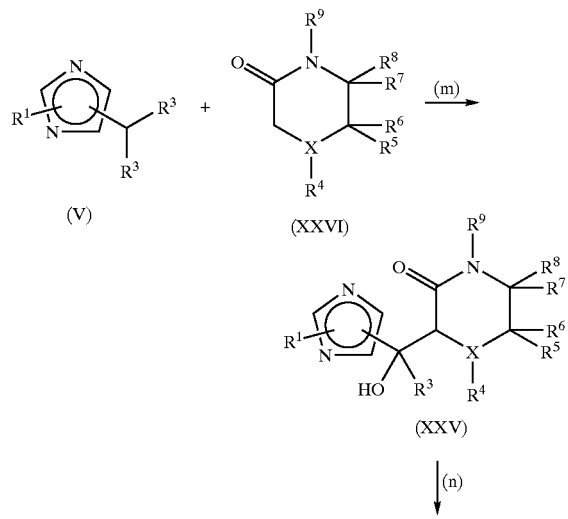

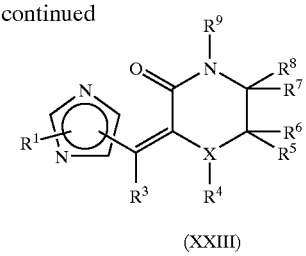

Compounds of formula (XXV) may be prepared from compounds of formula (V) and (XXVI) under the conditions of process step (m), an Aldol type reaction. Suitable conditions for such a reaction are well known to one skilled in the art. For a more detailed description see *Advanced Organic Chemistry* ($4^{th}$ Edition) by Jerry March, John Wiley and Sons Inc.

Compounds of formula (XXIII) may be prepared from compounds of formula (XXV) under the conditions of process step (n), an elimination reaction. (XXV) may be treated such that the hydroxy group is removed directly in a dehydration reaction, or it may be eliminated having first being transformed into a good leaving group such as a tosylate or mesylate group.

Compounds of formula (XXII) where $R^1$, $R^2$, $R^3$ $R^4$ $R^5$, $R^6$, $R^7$, $R^8$ and X are as disclosed above, $R^9$ is as disclosed above or a nitrogen-protecting group (Pg) and n is 0 may also be prepared from compounds of formula (XXX) and (XXVI) in accordance with the Scheme XIV below.

Scheme XIV

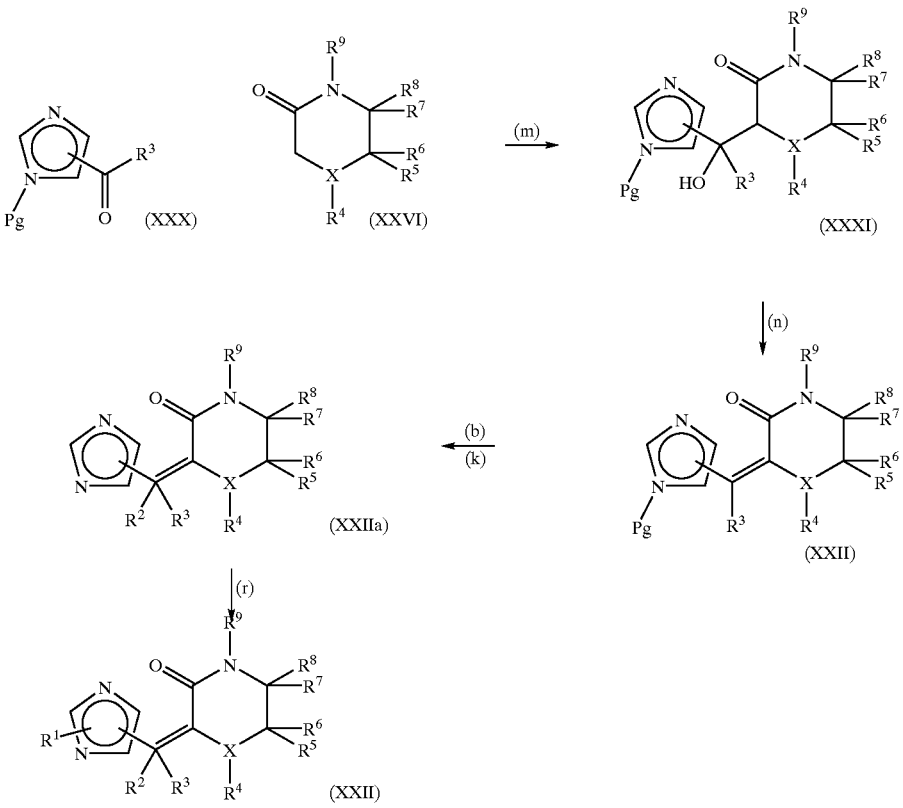

Compounds of formula (XXXI) may be prepared from compounds of formula (XXVI) and formula (XXX), wherein $R^3$ is as described above and Pg is a suitable nitrogen-protecting group under the conditions of process step (m) as described above.

Compounds of formula (XXXII) may be prepared from compounds of formula (XXXI) under the conditions of process step (n) as described above.

Compounds of formula (XXIIa) where $R^2$, $R^3$ $R^4$ $R^5$, $R^6$, $R^7$, $R^8$ and X are as disclosed above, $R^9$ is as disclosed above or a nitrogen-protecting group (Pg), n is 0 and $R^1$ is hydrogen may be prepared from compounds of formula (XXXII) under the conditions of process step (b), followed by process step (k), both as described above.

Compounds of formula (XXII) where $R^1$ is not hydrogen may be obtained from compounds of formula (XXIIa) under the conditions of process step (r), a coupling reaction. Suitable conditions, include those described in process steps (h) or (p) regarding alkylation reactions as well as arylation reactions well known to one skilled in the art. Typical alkylation conditions may include:

1.5 eq of base (eg $Cs_2CO_3$) and 1.25 eq of alkylating agent, (eg $R^1Br$), in DMF at 70° C. for 3 hours.

Suitable arylation conditions may include:

2 eq of $R^1$—$B(OH)_2$, 1.5 eq of Cu(II)acetate catalyst, 2 eq of pyridine in DCM, for 2 days, under a stream of compressed air. (P.Y.S. Lam et al, *Tetrahedron Lett.*, 39; 2941, 1998)

Compounds of formula (I), where $R^1$, $R^2$, $R^3$, $R^5$, $R^6$, $R^7$, $R^8$, $R^9$ and $R^{10}$ are as described above, $R^4$ is hydrogen and X is nitrogen, with the proviso one of $R^9$ and $R^{10}$ is not hydrogen and $R^1$ is attached to an imidazole N atom, may be prepared from compounds of formula (XXIX) in accordance with the reaction Scheme XV below.

Scheme XV

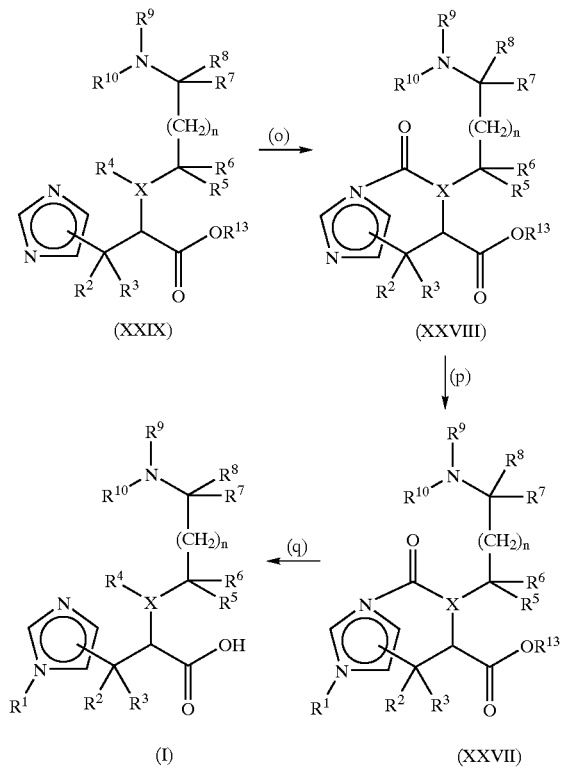

(XXIX)        (XXVIII)

(I)           (XXVII)

Compounds of formula (XXVIII) may be prepared from compounds of formula (XXIX) where $R^4$ is hydrogen and one of $R^9$ or $R^{10}$ is not hydrogen by process step (o), a carbonylation reaction. The reaction may be performed under standard conditions, such as described in *Tetrahedron* 1996, 52, 5363. Appropriate conditions include reacting 1 eq of (XXIX) with 1 eq of carbonyldiimidazole in N,N-dimethylformamide at 60° C. for 17 hours.

Compounds of formula (XXVII) may be prepared from compounds of formula (XXVIII) by process step (p), an alkylation reaction. This may be conducted under standard conditions, e.g. reacting (XXVIII) with an alkylating agent such as an alkyl halide, optionally in the presence of a catalyst, in a suitable solvent. Suitable conditions include treating 1 eq of (XXVIII) with 2 eq of $R^1$—Cl in acetonitrile at reflux for 18 hours.

Compounds of formula (I) may be prepared from compounds of formula (XXVII) under the conditions of process step (q), a hydrolytic deprotection reaction. The starting material is treated with an aqueous acid, preferably hydrochloric or sulfuric acid.

Compounds of formula (XXIX) may be prepared by the routes disclosed in this document, wherein $R^1$ is instead hydrogen.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

The present invention provides for the compounds of the present invention for use as a medicament.

The invention further provides for the use of a TAFIa inhibitor for the treatment or prevention of a condition selected from thrombosis, atherosclerosis, adhesions, dermal scarring, cancer, fibrotic conditions, inflammatory diseases and those conditions which benefit from maintaining or enhancing bradykinin levels in the body. The present invention also provides for the use of a TAFIa inhibitor in the preparation of a medicament for treating or preventing the conditions listed above.

Preferably, the TAFIa inhibitor is a compound of formula (I) as described herein. Accordingly the present invention provides for the use of a compound of the present invention in the preparation of a medicament for the treatment or prevention of a condition selected from thrombosis, atherosclerosis, adhesions, dermal scarring, cancer, fibrotic conditions, inflammatory diseases and those conditions which benefit from maintaining or enhancing bradykinin levels in the body.

Additionally the invention provides a method of treating or preventing thrombosis, atherosclerosis, adhesions, dermal scarring, cancer, fibrotic conditions, inflammatory diseases and those conditions which benefit from maintaining or enhancing bradykinin levels in the body which comprises administering a therapeutically effective amount of a TAFIa inhiitor and pharmaceutically acceptable salts, solvates and prodrugs thereof to a patient in need of such treatment.

Preferably, the TAFIa inhibitor is a compound of the present invention (e.g., a compound of formula (I) as described above). Accordingly, the present invention provides a method of treating or preventing thrombosis, atherosclerosis, adhesions, dermal scarring, cancer, fibrotic conditions, inflammatory diseases and those conditions which benefit from maintaining or enhancing bradykinin levels in the body which comprises administering a therapeutically effective amount of a compound of the present invention to a patient in need of such treatment.

Thrombotic conditions are amongst the most common cause of death in the developed world. There are large numbers of anti-thrombotic agents available to treat these conditions. Most agents work by reducing thrombus formation. All these agents are associated with varying degrees of adverse hemorrhagic side effects. Accordingly, patients being treated in this manner will require regular monitoring in order to avoid adverse bleeding events.

There is a need for an antithrombotic that is efficacious but does not cause bleeding. However this would seem impossible given the inherent contradiction between stopping clot formation to prevent thrombotic disease, and allowing clot formation so as to prevent the patient hemorrhaging.

Surprisingly, this has been solved by the compounds of the present invention which are a class of TAFIa inhibitors. Most conventional therapies act to inhibit coagulation or platelet activation. TAFIa inhibitors work by enhancing fibrinolysis and therefore the rate at which the clot is dissolved. This has the effect of shifting the equilibrium between coagulation and fibrinolysis, in favor of fibrinolysis. Most clinically relevant thrombus are sub acute, that is they form slowly over time. The effect of shifting the equilibrium in favor of fibrinolysis is that these clots are dissolved before they become clinically significant.

In the case of vascular injury, the equilibrium moves back in favor of coagulation. The body's first responses of vasoconstriction and platelet agglutination remain unimpaired by the use of TAFIa inhibitors. The body then rapidly activates the coagulation cascade. The effect of this is to temporarily shift the equilibrium towards coagulation and allow formation of a hemostatic plug using fibrin. Once the vascular injury is sealed the body will revert to its pre-injury equilibrium.

The present invention also provides for the use of TAFIa inhibitors in the preparation of a medicament for the treatment or prevention of thrombosis, particularly myocardial infarction, deep vein thrombosis, stroke, young stroke, peripheral vascular disease, angina and other forms of acute coronary syndromes, disseminated intravascular coagulation, sepsis, pulmonary embolism, embolic events secondary to cardiac arrhythmias and the prevention of cardiovascular events following intervention surgery. Preferably, the TAFIa inhibitor has a Ki of less than 20 $\mu$M, using the assay described below, and has a selectivity for TAFIa over carboxypeptidase N of >50:1, preferably >1000:1, using the assay described below. Preferably, the TAFIa inhibitors are non-peptidic.

Preferably, the TAFIa inhibitor is a compound of formula (I) as disclosed herein. Accordingly, the present invention provides for the use of a compound of the present invention in the preparation of a medicament for the treatment of a thrombotic condition selected from myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events following surgical revascularisation or intervention.

The invention also provides for a method of treating or preventing thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events following intervention surgery which comprises administering a therapeutically effective amount of a compound of the present invention to a patient in need of such treatment.

Subjects with thrombotic conditions which are suitable for treatment by the present invention include those having conditions associated with hypercoagulability. These would include though not limited to factor V mutation, antithrombin III deficiency, protein C and protein S deficiencies, polycythemia vera, heparin cofactor 11 and subjects exhibiting hyperhomocysteinaemia or homocysteinuria.

The present invention also includes as a thrombotic indication the improvement of organ function seen after transplantation, by reducing blood clotting and thus preserving function.

Cardiovascular events following intervention surgery include conditions such as restenosis or reocclusion following interventions such as percutaneous transluminal coronary angioplasty, grafting, stent in-placement, coronary bypass surgery or any other forms of surgical revascularization or intervention In the present invention, disseminated intravascular coagulation includes all conditions resulting from intravascular activation of the coagulation process. This might occur acutely through the release of procoagulant substances (eg. obstetric emergencies, snakebite, crush injury malignancy), by abnormal contact of the blood (e.g., infections, burns, extracorporeal circulation, grafts) or though generation of procoagulants in the blood (transfusion reactions, leukemia) or chronically (e.g., toxemia, malignant hypertension, and severe liver cirrhosis).

Deep vein thrombosis also encompasses what is known as 'economy class syndrome', where clots form in subjects forced to endure cramped conditions for a period of time, such as those sitting in cramped economy class seats on a plane.

The present invention also provides for the use of TAFIa inhibitors and/or TAFI inhibitors as a coating on intravascular devices such as indwelling catheters for dialysis, replacement heart valves or arterial stents and as a coating on extra corporeal blood circulation devices such as heart, lung and kidney dialysis machines, to prevent thrombosis, particularly myocardial infarction, deep vein thrombosis, stroke, young stroke, cerebral infarction, cerebral thrombosis, cerebral embolism, peripheral vascular disease, angina and other forms of acute coronary syndromes, disseminated intravascular coagulation, sepsis, pulmonary embolism, embolic events secondary to cardiac arrhythmias and the prevention of cardiovascular events such as restenosis following intervention surgery such as percutaneous transluminal coronary angioplasty, grafting, stent in-placement, coronary bypass surgery or any other forms of surgical revascularization or intervention. Particularly preferred as a coating are compounds of the present invention.

Accordingly the present invention provides for the use of TAFIa inhibitors and/or TAFI inhibitors as a coating on intravascular devices. In addition, the present invention provides for the use of a compound of the present invention as a coating on intravascular devices.

The invention includes intravascular devices, of which the intravascular portion is coated with a TAFIa inhibitor and/or a TAFI inhibitor and extra corporeal blood circulation devices such as heart, lung and kidney dialysis machines, where the portion coming into contact with the subjects blood are coated with a TAFIa inhibitor and/or a TAFI inhibitor. Particularly preferred are those intravascular or extra corporeal blood circulation devices coated with compounds of the present invention. Preferably, the TAFIa inhibitor has a Ki of less than 20 $\mu$M, using the assay described below and has a selectivity for TAFIa over carboxypeptidase N of >50:1, preferably >1000:1, using the assay described below. Preferably, the TAFIa inhibitors are non-peptidic.

Accordingly the present invention provides an intravascular device coated with a TAFIa inhibitor. In addition, the present invention provides an intravascular device coated with a compound of the present invention.

The compounds of the present invention were tested in a model of coronary artery reperfusion using a method similar to that described by W. E. Rote et al, *J. Cardiovasc. Pharmacol.*, 1994, 23, 203, and were found to be efficacious.

TAFIa inhibitors are also useful in the treatment of atherosclerosis. Atherosclerosis is a common condition in subjects suffering from peripheral vascular disease, insulin resistance and the group of conditions commonly referred to as 'Syndrome X'. Syndrome X is a term often used to group together a number of interrelated diseases. The first stage of syndrome X consists of insulin resistance, abnormal cholesterol and triglyceride levels, obesity and hypertension. Any one of these conditions may be used to diagnose the start of Syndrome X. The disease may then progress with one condition leading to the development of another in the group. For example insulin resistance is associated with high lipid levels, hypertension and obesity. The disease then cascades, with the development of each additional condition increasing the risk of developing more serious diseases. This can progress to the development of diabetes, kidney disease and heart disease. These diseases may lead to stroke, myocardial infarction and organ failure.

Conventional treatment of myocardial ischemia in clinically stable coronary artery disease is predominately designed to reduce cardiac workload and enhance blood flow. Such approaches clearly reduce myocardial ischemia thus increasing quality of life. However, these strategies have little effect on the pathogenesis of coronary atherosclerosis which is a chronic process of continuous remodeling of the vascular tree in response to varying degrees of vascular injury.

A role for thrombus formation in the pathophysiology of stable angina pectoris has recently been highlighted by several independent groups. The formation of non-occlusive thrombi not only restrict blood flow, but due to incomplete endogenous lysis may be incorporated by the arterial wall as solidified plaque material enhancing the atherosclerotic process. Long term administration of a TAFIa inhibitor prevents the formation of thrombi and therefore provides a safe and efficacious treatment which alleviates the symptoms of angina pectoris. Without thrombi present, they cannot be incorporated into the arterial wall and thus a TAFIa inhibitor impairs the progression of the disease.

The present invention also provides for the use of the compounds of the present invention in the preparation of a medicament for the treatment or prevention of atherosclerosis.

The invention also provides for a method of treating or preventing atherosclerosis which comprises administering a therapeutically effective amount of a compound of formula (I) and pharmaceutically acceptable salts and prodrugs thereof to a patient in need of treatment.

Further the invention also provides for the use of a TAFIa inhibitor in the preparation of a medicament for the treatment or prevention of atherosclerosis. Preferably, the TAFIa inhibitor has a Ki of less than 20 $\mu$M, using the assay described below and has a selectivity for TAFIa over carboxypeptidase N of >50:1, preferably >1000:1, using the assay described below. Preferably, the TAFIa inhibitors are non-peptidic.

Atherosclerosis is taken to include both primary and secondary coronary artery disease, in which atherosclerosis restricts the blood supply to the heart. Primary prevention of coronary artery disease means preventing the onset of ischemic complications such as myocardial infarction in patients with no history of coronary artery disease but who have one or more risk factors. Secondary prevention of coronary artery disease means preventing ischemic complications in patients with established coronary artery disease, such as patients who have had a previous myocardial infarction.

TAFIa inhibitors are also effective in inhibiting tumor maturation and progression. Metastasis is a complex and multifactorial process which is not yet fully understood. Accordingly, whilst not wishing to be bound by any theory, it is believed that the haemostatic system is involved at several levels of cancer pathology, including neovascularisation, shedding of cells from the primary tumor, invasion of the blood supply, adherence to the vessel wall and growth at the metastatic site. It is thought that the efficacy of TAFIa inhibitors stems from an ability to reduce fibrin deposition around solid tumors and thereby inhibit the above processes.

The present invention also provides for the use of compounds of the present invention in the preparation of a medicament for the treatment or prevention of cancer.

The invention also provides for a method of treating or preventing cancer which comprises administering a therapeutically effective amount of a compound of the present invention to a patient in need of such treatment.

In addition, the invention provides for the use of a TAFIa inhibitor in the preparation of a medicament for the treatment or prevention of cancer. Preferably, the TAFIa inhibitor has a Ki of less than 20 $\mu$M, using the assay described below and has a selectivity for TAFIa over carboxypeptidase N of >50:1, preferably >1000:1, using the assay described below. Preferably, the TAFIa inhibitors are non-peptidic.

TAFIa inhibitors are also effective in preventing the formation of adhesions in the body. Most surgical procedures and physical trauma result in bleeding into the cavity between tissues. The blood which collects at these sites then clots forming fibrin rich thrombi. These thrombi bridge the gaps between adjacent tissues and act as a foci for the accumulation of inflammatory cells and fibroblasts. Invading fibroblasts lay down a collagen rich extracellular matrix which strengthens the adhesion of the tissues producing a firm bond which may then restrict movement. Adhesions have been characterized according to their location and may result following any surgery e.g., abdominal, orthopaedic, neurological, cardiovascular and ocular. This, inappropriate, adhesion of tissues post surgery or trauma is a major issue which can lead to various outcomes e.g. "aches and pains", "twinges", local inflammation, restriction in mobility, pain, intestinal obstruction and sometimes in the most severe cases death. In the case of gynaecological surgery, infertility may result. Additionally clots forming fibrin rich thrombi are implicated in dermal scarring and restenosis.

Without being bound by any theory, it is believed that adhesion formation may be enhanced due to a deficiency in fibrinolysis resulting in enhanced and maintained clot formation. Treatment with a TAFIa inhibitor per- and/or post-surgical intervention may enhance fibrinolysis of the fibrin rich thrombi and hence inhibit thrombi formation, accretion, stabilization and therefore inhibit adhesion formation. A TAFIa inhibitor given either systemically, or locally as a topical application, may be seen to be of benefit in a range of surgical procedures. In addition, administration of a TAFIa inhibitor may be seen to treat adhesions resulting from other forms of non surgical physical trauma where this has caused internal bleeding. Examples of such trauma might include sporting injuries, or anything else resulting in a tear, cut, bruise or induaration of the body.

The present invention also provides for the use of compounds of the present invention in the preparation of a medicament for the treatment or prevention of adhesions or dermal scarring.

The invention also provides for a method of treating or preventing adhesions or dermal scarring which comprises administering a therapeutically effective amount of a compound of the present invention to a patient in need of such treatment.

In addition, the invention provides for the use of a TAFIa inhibitor in the preparation of a medicament for the treatment or prevention of adhesions or dermal scarring. Preferably said TAFIa inhibitor has a Ki of less than 20 µM, using the assay described below and has a selectivity for TAFIa over carboxypeptidase N of >50:1, preferably >1000:1, using the assay described below. Preferably, the TAFIa inhibitors are non-peptidic.

TAFIa binds to and breaks down bradykinin (Tan et al. *Biochemistry* 1995, 34, 5811). There are many conditions which are known to benefit from maintaining or enhancing levels of bradykinin. Accordingly, the present invention also provides for the use of compounds of formula (I) and pharmaceutically acceptable salts, solvates and prodrugs thereof in the preparation of a medicament for the treatment or prevention of conditions which benefit from maintaining or enhancing levels of bradykinin.

The invention also provides for a method of treating or preventing conditions which benefit from maintaining or enhancing levels of bradykinin which comprises administering a therapeutically effective amount of a compound of the present invention to a patient in need of such treatment.

Conditions known to benefit from maintaining or enhancing bradykinin levels include diseases such as hypertension, angina, heart failure, pulmonary hypertension, renal failure and organ failure.

TAFIa inhibitors are efficacious in treatment of any condition in which fibrosis is a contributing factor. Accordingly, the present invention also provides for the use of TAFIa inhibitors in the preparation of a medicament for the treatment or prevention of fibrotic disease. Preferably, the TAFIa inhibitor has a Ki of less than 20 µM, using the assay described below and has a selectivity for TAFIa over carboxypeptidase N of >50:1, preferably >1000:1, using the assay described below. Preferably, the TAFIa inhibitors are non-peptidic. Particularly preferred are compounds of formula (I) and pharmaceutically acceptable salts, solvates and prodrugs thereof.

Suitable fibrotic conditions include cystic fibrosis, pulmonary fibrotic diseases e.g., chronic obstructive pulmonary disease (COPD), adult respiratory distress syndrome (ARDS), fibromuscular dysplasia, fibrotic lung disease and fibrin deposits in the eye during opthalmic surgery.

Accordingly, the present invention provides for the use of a compound of formula (I) as disclosed herein in the preparation of a medicament for the treatment or prevention of a fibrotic condition selected from cystic fibrosis, pulmonary fibrotic diseases, chronic obstructive pulmonary disease (COPD), adult respiratory distress syndrome (ARDS), fibromuscular dysplasia, fibrotic lung disease and fibrin deposits in the eye during opthalmic surgery.

The invention also provides for a method of treating or preventing a fibrotic condition selected from cystic fibrosis, pulmonary fibrotic diseases, chronic obstructive pulmonary disease (COPD), adult respiratory distress syndrome (ARDS), fibromuscular dysplasia, fibrotic lung disease and fibrin deposits in the eye during opthalmic surgery which comprises administering a therapeutically effective amount of a compound of the present invention to a patient in need of treatment.

TAFIa inhibitors are efficacious in treatment of inflammation. Accordingly, the present invention also provides for the use of TAFIa inhibitors in the preparation of a medicament for the treatment or prevention of inflammation. Preferably, the TAFIa inhibitor has a Ki of less than 20 µM, using the assay described below and has a selectivity for TAFIa over carboxypeptidase N of >50:1, preferably >1000:1, using the assay described below. Preferably, the TAFIa inhibitors are non-peptidic. Particularly preferred are compounds of formula (I) and pharmaceutically acceptable salts, solvates and prodrugs thereof.

In particular, the invention may be used for the treatment or prevention of inflammatory diseases such as asthma, arthritis, endometriosis, inflammatory bowel diseases, psoriasis and atopic dermatitis and for neurodegenerative diseases such as Alzheimers and Parkinsons.

Accordingly, the present invention provides for the use of a compound of formula (I) and pharmaceutically acceptable salts, solvates and prodrugs thereof in the preparation of a medicament for the treatment of an inflammatory disease selected from asthma, arthritis, endometriosis, inflammatory bowel diseases, psoriasis and atopic dermatitis and neurodegenerative diseases, Alzheimers and Parkinsons.

The invention also provides for a method of treating or preventing an inflammatory disease selected from asthma, arthritis, endometriosis, inflammatory bowel diseases, psoriasis and atopic dermatitis and neurodegenerative diseases, Alzheimers and Parkinsons which comprises administering a therapeutically effective amount of a compound of formula (I) and pharmaceutically acceptable salts and prodrugs thereof to a patient in need of treatment.

It is to be appreciated that all references herein to treatment include curative, palliative and prophylactic treatment.

The compounds of the present invention have been tested using the following assay. To determine the degree of TAFIa inhibition, compounds were incubated with activated TAFI, and the amount of inhibition expressed in terms of Ki. This assay is based on that disclosed in Boffa et al, *J. Biol. Chem.*, 1998, 273, 2127.

Assay for TAFIa Inhibition i) TAFI Activation

Human TAFI (recombinant or purified) was activated by incubating 20 µl of stock solution (360 µg/ml) with 10 µl of human thrombin (10 NIH units/ml), 10 µl of rabbit thrombomodulin (30 µg/ml), 6 µl calcium chloride (50 mM) in 50 µL of 20 mM HEPES (N-[2-hydroxyethyl]piperazine-N-[2-ethanesulfonic acid]) buffer containing 150 mM sodium chloride and 0.01% TWEEN 80 (polyoxyethylene-sorbitan monooleate) pH 7.6 for 20 minutes at 22° C. At the end of the incubation period, thrombin was neutralized by the addition of 10 µL of PPACK (D-Phe-Pro-Arg chloromethyl ketone)(100 nM). TAFIa solution was stored on ice for 5 minutes and finally diluted with 175 µl of HEPES buffer.

ii) Ki Determination (TAFIa)

Calculated Ki

A number of different dilutions of the test compound in water were made up. To 20 µl of each dilution was added 150 µl of HEPES buffer and 10 µl of TAFIa, which was then pre-incubated for 15 minutes at 24° C. To each dilution was then added 20 µl furylacryloyl-alanyl-lysine (FAAL) at a standard concentration. Substrate turn over was measured by reading the absorbance of the reaction mixture at 330 nm every 15 seconds for 30 minutes. Reaction was performed at 24° C. and samples were mixed for 3 seconds prior to each absorbance reading.

A graph of % inhibition against test compound concentration was then plotted; from which was calculated the $IC_{50}$ value. The Ki value may then be calculated using the Cheng-Prusoff equation.

Two controls, positive and negative, were used to check the accuracy of the results in each case. For the first control, the assay was performed as above, but with 20 µl of water rather than a dilution of the test compound. This showed minimal inhibition. For the second control, the assay was performed as above, but with an effective amount of a non specific carboxypeptidase inhibitor rather than a dilution of the test compound. This showed maximal inhibition.

Should the two controls not demonstrate minimal and maximal inhibition respectively then the results were discounted and the test compound reanalyzed.

Using the above assay the compounds of the present invention were found to be potent and selective inhibitors of TAFIa. All compounds had a Ki value less than 20 μM. The specific Ki value of certain compounds are detailed below:

(±)-6-Amino-2-[(1-n-propyl-1H-imidazol-4-yl)methyl] hexanoic acid (Example 3) Ki=310 nM (+)-(2S)-5-Amino-2-[(1-n-propyl-1H-imidazol-4-yl) methyl]pentanoic acid (Example 7) Ki=13 nM (2S)-2-[(2-Aminoethyl)amino]-3-(1H-imidazol-4-yl) propanoic acid (Example 11) Ki=344 nM (2S)-2-[(2-Aminoethyl)amino]-3-[1-(1,3-thiazol-5-ylmethyl)-1H-imidazol-4-yl]propanoic acid (Example 45) Ki=197 nM The selectivity of the compounds of the present invention for TAFIa over carboxypeptidase N has also been determined. This was done by calculating the Ki of the compounds of the present invention for carboxypeptidase N, then comparing it to the Ki for TAFIa. The Ki was calculated using the assay for the calculation of TAFIa Ki, but substituting 10 μl of human carboxypeptidase N for 10 μl of TAFIa.

The compounds of the present invention exhibit a strong selectivity for TAFIa over carboxypeptidase N of the order of >50:1.

The compounds of the present invention are TAFIa inhibitors, whose utility is based upon preventing the reaction between a developing thrombus and TAFIa.

It has been found that the compounds of the present invention are also capable of binding to a TAFI molecule, at the site implicated in the reaction between TAFIa and the developing clot. The use of TAFIa inhibitors as described above in terms of scope and utility, includes such TAFIa inhibitors which bind to TAFI.

The compounds of the formula (I) can also be administered together with other antithrombotics, including antiplatelet, anticoagulants and profibrinolytics. Suitable antithrombotics include: aspirin, Plavix™, ticlopidine, warfarin (coumarin™), unfractionated heparin, hirudin (Lepirudin™), streptokinase, urokinase, recombinant tissue plasminogen activator (tPA), dipyridamole, Reopro™, Aggrastat™, and Integrilin™. The compounds of the formula (I) can also be administered together with antihypertensives and with agents to treat dyslipidaemia such as statins eg Lipitor™.

Further suitable drug classes for coadministration include Factor X inhibitors and antiarrhythmics such as amiodarone or digoxin.

The present invention provides for the use of a TAFIa inhibitor in the preparation of a medicament in combination with an antithrombotic for the treatment of thrombosis.

The present invention provides for the use of a compound of formula (I) as described above in the preparation of a medicament in combination with an antithrombotic for the treatment of thrombosis.

In a preferred embodiment, the antithrombotic is an profibrinolytic.

In a more preferred embodiment, the antithrombotic is recombinant tissue plasminogen activator (tPA).

The present invention provides a method of treating or preventing thrombosis, which comprises administering a therapeutically effective amount of a TAFIa inhibitor in combination with an antifibrinolytic to a patient in need of such treatment.

The present invention also provides for a method of treating or preventing thrombosis, which comprises administering a therapeutically effective amount of a compound of the present invention in combination with an profibrinolytic to a patient in need of such treatment.

In a preferred embodiment the antithrombotic is an profibrinolytic.

In a more preferred embodiment the antithrombotic is recombinant tissue plasminogen activator (tPA).

The present invention provides for a kit comprising:

a) a composition comprising a compound of the present invention and a pharmaceutically acceptable diluent or carrier;

b) a composition comprising an antithrombotic and a pharmaceutically acceptable diluent or carrier; and c) a container;

The components of this kit may be administered separately, simultaneously or sequentially.

The ability of a TAFIa inhibitor used in conjunction with an antithrombotic to lyse thrombi was investigated using surgical procedures similar to those outlined in *J. Cardiovasc. Pharmacol.*, 1994 February; 23(2)194–202 and 203–211.

The study was designed with 4 groups (8 dogs/group):

(i) aspirin pre-treatment/vehicle infusion;

(ii) no pre-treatment/vehicle infusion;

(iii) no pre-treatment/TAFIa inhibitor; and (iv) aspirin pre-treatment/TAFIa inhibitor.

Method

Aspirin pre-treatment was 325 mg daily for 3 days. TAFIa inhibitor (compound of Ex 7) was given as a loading dose followed by a continuous infusion with the aim of achieving a steady state free plasma concentration of 4000 nM (220× $IC_{50}$ for TAFIa, in vitro). Thirty minutes after initiating vehicle or compound infusion a continuous electrical current was delivered to the lumen of the left circumflex (LCX) coronary artery to cause endothelial damage and stimulate the production of a thrombus. Thrombi were allowed to mature for 1 hour prior to attempting to lyse the thrombus and cause vessel reperfusion with t-PA. A total of 4 bolus injections of t-PA (each 0.45 mg/kg i.v.) were given sequentially at 15 minute intervals. Blood flow through the coronary artery was then monitored for a further 2 hours so as to assess vessel patency. Time to vessel occlusion, and reperfusion were measured and the quantity and quality of blood flow analysed post-vessel re-perfusion. In addition, the effect of treatment on surgical bleeding, activated clotting time, cutaneous bleeding and platelet aggregation was also assessed.

Results

Data is described in FIG. 1. From FIG. 1, it can be seen that:

1) TPA alone is superior to the combination of tPA and aspirin.

2) The combination of a TAFIa inhibitor and tPA is far superior to tPA alone.

3) The improvement in coronary blood flow caused by TAFIa inhibitor was maintained for the whole of the reperfusion period (165 minutes) with significantly greater flow compared to respective controls. Notably, TAFIa inhibitor significantly increased the proportion of animals in which flow was >75% of baseline at the end of the protocol. At the end of the experiment only 2/8 dogs in the no pre-treatment/vehicle group and 1/8 dogs in the aspirin pre-treatment/vehicle group were patent. In contrast, the injured vessels were patent in 8/8 dogs in the TAFIa inhibitor treatment group.

4) There was no effect of any of the treatments on surgical bleeding, cutaneous bleeding time, activated clotting time or ADP induced platelet aggregation either pre- or post t-PA treatment.

Combination (iv) is not considered here.

The present invention also provides for a composition comprising a compound of the present invention and a pharmaceutically acceptable excipient, diluent or carrier.

The compounds of the present invention can be administered alone but will generally be administered in admixture with a suitable pharmaceutical excipient, diluent or carrier selected with regard to the intended route of administration and standard pharmaceutical practice. For example, the compounds of the present invention can be administered orally, buccally or sublingually in the form of tablets, capsules, ovules, elixirs, solutions or suspensions, which may contain flavoring or coloring agents, for immediate-, delayed-, modified-, sustained-, pulsed- or controlled-release applications.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavoring agents, coloring matter or dyes, with emulsifying and/or suspending agents and with diluents such as water, ethanol, propylene glycol and glycerin, and combinations thereof.

The compounds of the present invention may also be administered in the form of a liquid or suspension filled soft or hard gelatin capsule. Such capsules are generally made of gelatin, glycerin, water and sorbitol. Hard capsules are distinguished from soft capsules by containing less water and thus having a correspondingly stronger shell. Additional excipients suitable for use in such capsules include propylene glycol, ethanol, water, glycerol and edible oils.

The compounds of present invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The compounds of present invention can also be administered intranasally or by inhalation and are conveniently delivered in the form of a dry powder inhaler or an aerosol spray presentation from a pressurized container, pump, spray, atomizer or nebulizer, with or without the use of a suitable propellant, e.g. dichlorodifluoro-methane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurized aerosol, the dosage unit may be determined by providing a valve to deliver a metered amount. The pressurized container, pump, spray, atomizer or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the present invention and a suitable powder base such as lactose or starch.

Alternatively, the compounds of the present invention can be administered in the form of a suppository or pessary, or they may be applied topically in the form of a gel, hydrogel, lotion, solution, cream, ointment or dusting powder. The compounds of the present invention may also be dermally or transdermally administered, for example, by the use of a skin patch. They may also be administered by the pulmonary or rectal routes.

The compounds of the present invention may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application, the compounds of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds of the present invention can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g., as a carrier, diluent or solubilizer. Alpha-, beta- and gamma-cyclodextrins are most commonly used and suitable examples are described in PCT publications WO-A-91/11172, WO-A-94/02518 and WO-A-98/55148.

The present invention is further illustrated by the following, non-limiting examples.

EXAMPLES

Melting points were determined on a Gallenkamp melting point apparatus using glass capillary tubes and are uncorrected. Unless otherwise indicated all reactions were carried out under a nitrogen atmosphere, using commercially available anhydrous solvents. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40–63 μm silica gel (Merck silica gel 60). Ion exchange chromatography was performed using with the specified ion exchange resin which had been pre-washed with deionized water. Proton NMR spectra were measured on a Varian Inova 300, Varian Inova 400, or Varian Mercury 400 spectrometer in the solvents specified. In the NMR spectra, only exchangeable protons which appeared distinct from the solvent peaks are reported. Low resolution mass spectra were recorded on either a Fisons Trio 1000, using thermospray positive ionization, or a Finnigan Navigator, using electrospray positive or negative ionization. High resolution mass spectra were recorded on a Bruker Apex II FT-MS using electrospray positive ionization. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in deionized water.

| Abbreviations and Definitions | |
|---|---|
| Arbocel ™ | Filtration agent, from J. Rettenmaier & Sohne, Germany |
| Amberlyst ® 15 | Ion exchange resin, available from Aldrich Chemical Company |
| atm | Pressure in atmospheres (1 atm = 760 Torr) |
| Biotage ™ | Chromatography performed using Flash 75 silica gel cartridge, from Biotage, UK |
| BOC | tert-Butyloxycarbonyl group |
| br | Broad |
| c | Concentration used for optical rotation measurements in g per 100 ml (1 mg/ml is c 0.10) |
| cat | Catalytic |
| d | Doublet |
| dd | Doublet of doublets |
| Degussa ® 101 Company | 10 wt % palladium on activated carbon, Degussa type E101 available from Aldrich Chemical Company |
| DOWEX ® | Ion exchange resin, from Aldrich Chemical Company |
| ee | Enantiomeric excess |
| HRMS | High Resolution Mass Spectrocopy (electrospray ionisation positive scan) |
| Hyflo ™ | Hyflo super cel ®, from Aldrich Chemical Company |
| liq | liquid |
| LRMS | Low Resolution Mass Spectroscopy (electrospray or thermospray ionisation positive scan) |
| LRMS (ES⁻) | Low Resolution Mass Spectroscopy (electrospray ionisation negative scan) |
| m | Multiplet |
| m/z | Mass spectrum peak |
| MCI ™ gel | High porous polymer, CHP20P 75–150 μm, from Mitsubishi Chemical Corporation |
| q | Quartet |
| Rf | Retention factor on TLC |
| s | Singlet |
| Sep-Pak ® | Reverse phase C18 silica gel cartridge, Waters Corporation |
| t | Triplet |
| TLC | Thin Layer Chromatography |
| δ | Chemical shift |

Example 1

(+)-5-Amino-2-(1H-imidazol-4-ylmethyl)pentanoic acid

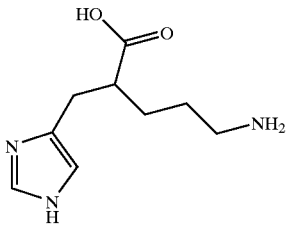

A mixture of the ester from Preparation 1 (150 mg, 0.25 mmol) in dioxane (2 ml) and aqueous sodium hydroxide (2 ml, 2N) was stirred at room temperature for 1.5 hours. Aqueous hydrochloric acid (6 ml, 6N) was carefully added, and the reaction heated under reflux for 24 hours. The cooled mixture was purified by ion exchange column chromatography (DOWEX® 50WX8-200), using an elution gradient of deionized water:0.88 ammonia (100:0 to 97:3). The product was triturated with methanol to give the title compound as a white solid, 28 mg, 57% yield.

$^1$H-NMR (CD$_3$OD, 300 MHz) δ: 1.44–1.75 (m, 4H), 2.48 (m, 1H), 2.62 (dd, 1H), 2.90 (m, 3H), 6.81 (s, 1H), 7.55 (s, 1H).

HRMS: m/z 198.1242 (MH⁺), calcd 198.1237.

Example 2

(±)-5-Amino-2-[(1-n-propyl-1H-imidazol-4-yl)methyl]pentanoic acid

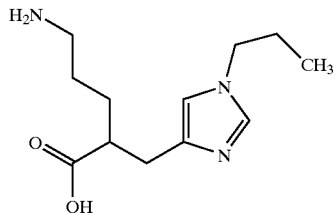

A mixture of the ester from Preparation 2 (85 mg, 0.17 mmol) in dioxane (1 ml) and aqueous sodium hydroxide (1 ml, 2N) was stirred at room temperature for 72 hours. TLC analysis showed starting material remaining, so the reaction was heated at 70° C. for 3 hours. Aqueous hydrochloric acid (2 ml, 6N) was added to the cooled solution and the reaction stirred at room temperature for 18 hours. TLC analysis showed starting material remaining, so the reaction was stirred at 70° C. for a further 2 hours. The cooled mixture was extracted with hexane, and the remaining aqueous solution was purified by ion exchange column chromatography (DOWEX® 50WX8-200) eluting with a solvent gradient of deionized water: 0.88 ammonia (100:0 to 97:3). The product was dissolved in a minimum volume of deionized water, and freeze-dried to give the title compound as a gum, 18 mg, 43% yield.

$^1$H-NMR (CD$_3$OD, 300 MHz) δ: 0.92 (t, 3H), 1.45–1.70 (m, 4H), 1.79 (m, 2H), 2.43–2.60 (m, 2H), 2.76–2.95 (m, 3H), 3.90 (t, 2H), 6.86 (s, 1H), 7.45 (s, 1H).

HRMS: m/z 240.1713 (MH⁺), calcd 240.1706.

Example 3

(±)-6-Amino-2-[(1-n-propyl-1H-imidazol-4-yl)methyl]hexanoic acid

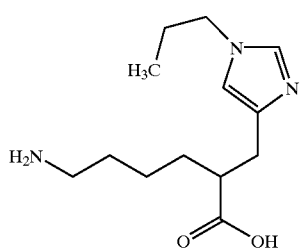

A mixture of the protected amine from Preparation 3 (17 mg, 0.05 mmol) in aqueous hydrochloric acid (2 ml, 6N) was stirred at room temperature for 3 hours. The solution was purified directly by ion exchange chromatography (DOWEX® 50WX8-200), eluting with a solvent gradient of deionized water:0.88 ammonia (100:0 to 97:3), to give the title compound, 7 mg, 55% yield.

$^1$H-NMR (CD$_3$OD, 300 MHz) δ: 0.88 (t, 3H), 1.42 (m, 3H), 1.62 (m, 3H), 1.78 (m, 2H), 2.54 (m, 2H), 2.89 (m, 3H), 3.90 (t, 2H), 6.85 (s, 1H), 7.46 (s, 1H).

HRMS: m/z 254.1870 (MH⁺), calcd 254.1863.

Example 4

(−)-(2R)-5-Amino-2-[(1-n-butyl-1H-imidazol-4-yl)methyl]pentanoic acid

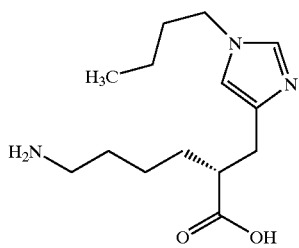

A mixture of the ester from Preparation 6 (185 mg, 0.35 mmol) in dioxane (6 ml) and aqueous sodium hydroxide (6 ml, 2N) was stirred at 50° C. for 3 hours. Aqueous hydrochloric acid (12 ml, 6N) was carefully added, and the reaction stirred at 70° C. for a further 18 hours. The cooled mixture was washed with ether, and the aqueous solution purified by ion exchange chromatography (DOWEX® 50WX8-200) eluting with a solvent gradient of deionized water:0.88 ammonia (100:0 to 95:5). The product was azeotroped well with ether and dried in vacuo to give the title compound as an off-white solid, 45 mg, 51% yield.

$^1$H-NMR (CD$_3$OD, 300 MHz) δ: 0.97 (t, 3H), 1.33 (m, 2H), 1.48–1.79 (m, 6H), 2.45–2.61 (m, 2H), 2.79–2.95 (m, 3H), 3.95 (t, 2H), 6.88 (s, 1H), 7.45 (s, 1H).

HRMS: m/z 254.1873 (MH$^+$), calcd 254.1863.

Example 5

(+)-(2S)-5-Amino-2-[(1-n-butyl-1H-imidazol-4-yl)methyl]pentanoic acid

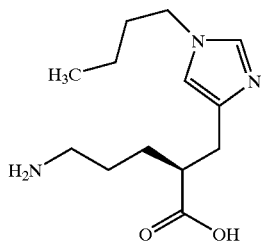

The title compound was obtained in 35% yield, from the ester from Preparation 7, following a similar procedure to that described in Example 4.

$^1$H-NMR (CD$_3$OD, 300 MHz) δ: 0.97 (t, 3H), 1.33 (m, 2H), 1.48–1.79 (m, 6H), 2.45–2.61 (m, 2H), 2.79–2.95 (m, 3H), 3.95 (t, 2H), 6.88 (s, 1H), 7.45 (s, 1H).

HRMS: m/z 254.1874 (M$^+$), calcd 254.1863.

[α]$_D$=+3.7 (c 0.14, deionized water)

[α]$_D$=−5.2 (c 0.15, methanol)

Example 6

(−)-(2R)-5-Amino-2-[(1-n-propyl-1H-imidazol-4-yl)methyl]pentanoic acid

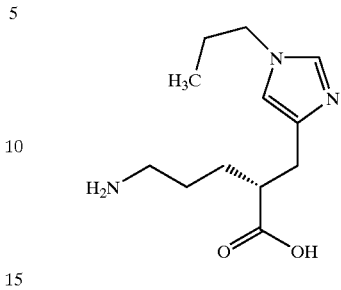

A solution of the protected amine from Preparation 9 (1.01 g, 2.97 mmol) in aqueous hydrochloric acid (15 ml, 6N) was stirred at room temperature for 18 hours. The solution was purified directly by ion exchange chromatography (DOWEX® 50WX8-200), eluting with a solvent gradient of deionized water:0.88 ammonia (100:0 to 97:3), to give the title compound, 680 mg, 94% yield.

$^1$H-NMR (CD$_3$OD, 400 MHz) δ: 0.84 (t, 3H), 1.48 (m, 1H), 1.55–1.68 (m, 3H), 1.76 (m, 2H), 2.42–2.57 (m, 2H), 2.86 (m, 3H), 3.83 (t, 2H), 6.82 (s, 1H), 7.42 (s, 1H).

HRMS: m/z 262.1533 (MNa$^+$), calcd 262.1526.

Anal. Found: C, 58.04; H, 8.93; N, 16.92. C$_{12}$H$_{21}$N$_3$O$_2$.0.5H$_2$O requires C, 58.04; H, 8.93; N, 16.92%.

[α]$_D$=−2.53 (c 0.15, deionized water)

Example 7

(+)-(2S)-5-Amino-2-[(1-n-propyl-1H-imidazol-4-yl)methyl]pentanoic acid

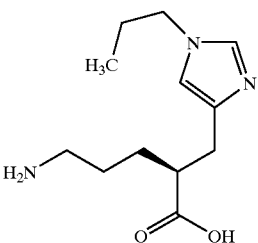

Lithium hydroxide monohydrate (1.1 g, 28 mmol) and water (28 ml) were added to a solution of the lactam from Preparation 11 (3 g, 9.33 mmol) in tetrahydrofuran (45 ml), and the reaction stirred at room temperature for 18 hours. The solution was neutralized using aqueous hydrochloric acid (6N), then further acid (15 ml, 6N) was added, and the solution stirred at room temperature for 4 hours. The mixture was purified directly by ion exchange chromatography (DOWEX® 50WX8-200), eluting with a solvent gradient of deionized water:0.88 ammonia (100:0 to 97:3), to give the title compound as a solid, 2.1 g, 94% yield. This was triturated well with acetone, the supernatant removed, and the residual solid dried in vacuo, to give the title compound as a white solid.

$^1$H-NMR (D$_2$O, 400 MHz) δ: 0.60 (t, 3H), 1.30 (m, 2H), 1.40 (m, 2H), 1.55 (m, 2H), 2.26–2.40 (m, 2H), 2.57 (dd, 1H), 2.76 (m, 2H), 3.68 (t, 2H), 6.66 (s, 1H), 7.36 (s, 1H).

HRMS: m/z 240.1699 (MH$^+$), calcd 240.1706.

Anal. Found: C, 58.90; H, 8.90; N, 17.17. C$_{12}$H$_{21}$N$_3$O$_2$.0.3H$_2$O requires C, 58.88; H, 8.92; N, 16.99%.

[α]$_D$=+2.80 (c 0.14, deionized water)

[α]$_D$=−4.9 (c 0.16, methanol)

[α]$_D$=−5.0 (c 0.10, ethanol)

Alternative Method for Example 7

A slurry of the quinidine salt from preparation 110 (19 g, 28.6 mmol) in water (95 ml) was adjusted to pH 10 using 5N sodium hydroxide solution, and the mixture extracted with dichloromethane (1×40 ml, 2×20 ml). The remaining aqueous suspension was acidified using 5N hydrochloric acid to pH 0.5, and the solution stirred at room temperature for 18 hours. The solution was purified on a Dowex® HCR-S ion-exchange resin column (40 g), using an elution gradient of water:0.88 ammonia (100:0 to 97:3). The resulting foam was slurried with acetone (20 ml), the solid filtered and dried in vacuo at 40° C. to afford the title compound as a white solid, 4.6 g, 68% yield.

$^1$H-NMR (CD$_3$OD, 400 MHz) δ: 0.87 (t, 3H), 1.50 (m, 1H), 1.58–1.72 (m, 3H), 1.78 (m, 2H), 2.44–2.59 (m, 2H), 2.90 (m, 3H), 3.88 (t, 2H), 6.84 (s 1H), 7.46 (s, 1H).

LRMS: m/z 240 (MH$^+$)

HRMS: m/z 240.1705 (MH$^+$), calcd 240.1706.

Anal. Found: C, 49.10; H, 9.34; N, 14.31. C$_{12}$H$_{21}$N$_3$O$_2$.3H$_2$O requires C, 49.13; H, 9.28; N, 14.32%.

Example 8

(−)-(2R)-5-Amino-2-(1H-imidazol-4-ylmethyl) pentanoic acid

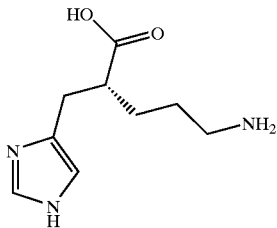

A mixture of the protected amine from Preparation 12 (85 mg, 0.14 mmol) in aqueous sodium hydroxide (1 ml, 2N) and dioxane (1 ml) was stirred at room temperature for 3 days. TLC analysis showed starting material remaining, so additional aqueous sodium hydroxide (1 ml, 2N) was added, and the reaction stirred at 50° C. for 18 hours. The mixture was cooled and treated with aqueous hydrochloric acid (5 ml, 6N). The solution was then stirred at 80° C. for 18 hours, cooled to room temperature, hexane added and the mixture stirred for an hour. The layers were separated, and the aqueous phase purified directly by ion exchange chromatography (DOWEX® 50WX8-200), eluting with a solvent gradient of deionized water:0.88 ammonia (100:0 to 97:3), to give the title compound, 20 mg, 73% yield.

$^1$H-NMR (CD$_3$OD, 300 MHz) δ: 1.40–1.68 (m, 4H), 2.45 (m, 1H), 2.62 (dd, 1H), 2.78 (m, 2H), 2.90 (m, 1H), 6.78 (s, 1H), 7.50 (s, 1H).

HRMS: m/z 198.1243 (MH$^+$), calcd 198.1237.

[α]$_D$=−6.0 (c 0.1 mg/ml, deionized water)

Example 9

(+)-(2S)-5-Amino-2-(1H-imidazol-4-ylmethyl) pentanoic acid

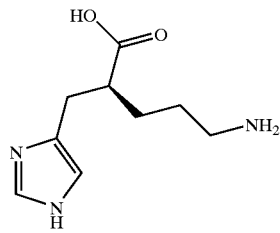

The title compound was obtained in 96% yield from the protected amine from Preparation 13, following the procedure described in Example 8.

$^1$H-NMR (CD$_3$OD, 300 MHz) δ: 1.45 (m, 1H), 1.59 (m, 3H), 2.47 (m, 1H), 2.62 (dd, 1H), 2.78 (m, 2H), 2.90 (dd, 1H), 6.80 (s, 1H), 7.50 (s, 1H).

HRMS: m/z 220.1064 (MNa$^+$), calcd 220.1056.

Example 10

(±)-5-Amino-2-[(4-n-propyl-1H-imidazol-2-yl) methyl]pentanoic acid

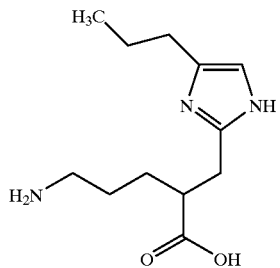

A mixture of the protected amine from Preparation 14 (108 mg, 0.23 mmol) in aqueous hydrochloric acid (1.5 ml, 6N) was stirred under reflux for 1.5 hours. The cooled solution was purified directly by ion exchange chromatography (DOWEX® 50WX8-200), eluting with a solvent gradient of deionized water:0.88 ammonia (100:0 to 96:4), to give the title compound as a white solid, 30 mg, 55% yield.

$^1$H-NMR (CD$_3$OD, 400 MHz) δ: 0.95 (t, 3H), 1.45 (m, 1H), 1.62 (m, 5H), 2.48 (t, 2H), 2.58 (m, 1H), 2.76 (dd, 1H), 2.86 (m, 2H), 2.98 (dd, 1H), 6.60 (s, 1H).

HRMS: m/z 240.1718 (MH$^+$), calcd 240.1707.

Anal. Found: C, 54.04; H, 8.97; N, 15.68. C$_{12}$H$_{21}$N$_3$O$_2$.1.5H$_2$O requires C, 54.12; H, 9.08; N, 15.78%.

Example 11

(2S)-2-[(2-Aminoethyl)amino]-3-(1H-imidazol-4-yl)
propanoic acid

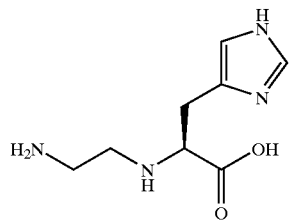

Trifluoroacetic acid (17 ml) was added dropwise to a stirred solution of the product from Preparation 16 (2.58 g, 8.2 mmol) in methanol:water (27 ml:14 ml). The reaction was slightly exothermic with evolution of carbon dioxide gas. The mixture was stirred at room temperature for 4 hours and the solvent was removed by evaporation under reduced pressure to give a colorless oil which was dried in vacuo overnight. The resultant oil was treated with aqueous sodium hydroxide solution (1N) until solution was at pH=8. A further portion of aqueous sodium hydroxide solution (1N, 30 ml) was added and the solution was stirred at room temperature for 72 hours. The solution was concentrated under reduced pressure to 10 ml and purified by ion exchange chromatography (DOWEX® 50WX8-200) eluting with a solvent gradient of deionized water:0.88 ammonia solution (100:0 to 97:3). The solvent was removed by evaporation under reduced pressure to afford a yellow oil which was dissolved in deionized water (15 ml) and freeze-dried overnight to afford a foam. This material was dissolved in deionized water:methanol (95:5) and further purified using MCI™ gel (55 g) chromatography, eluting with a solvent gradient of deionized water:methanol (95:5) to afford the title compound, 1.13 g, 69% yield.

$^1$H-NMR (D$_2$O, 300 MHz) δ: 2.61–2.87 (m, 4H), 2.92 (m, 2H), 3.25 (t, 1H), 6.81 (s, 1H), 7.59 (s, 1H).

LRMS: m/z 199.2 (MH$^+$)

Anal. Found: C, 43.36; H, 7.51; N, 25.12. C$_8$H$_{14}$N$_4$O$_2$.1.3H$_2$O requires C, 43.35; H, 7.54; N, 25.28%.

[α]$_D$=+1.74 (c 0.12, deionized water)

Example 12

(2R)-2-[(2-Aminoethyl)amino]-3-(1H-imidazol-4-yl)
propanoic acid

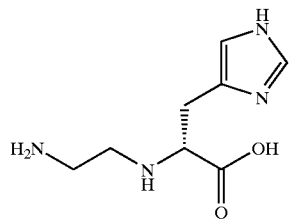

The title compound was prepared from the product of Preparation 17 using the procedure described for Example 11.

$^1$H-NMR (D$_2$O, 300 MHz) δ: 2.57–2.82 (m, 4H), 2.89 (m, 2H), 3.22 (t, 1H), 6.77 (s, 1H), 7.55 (s, 1H).

[α]$_D$=−1.0 (c 0.10, deionized water)

Example 13

(±)-2-[(2-Aminoethyl)amino]-3-(1H-imidazol-2-yl)
propanoic acid

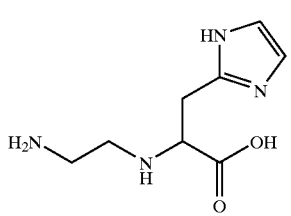

Trifluoroacetic acid (0.5 ml) was added dropwise to a stirred solution the product from Preparation 18 (105 mg, 0.34 mmol) in methanol:water (2 ml:1 ml) and the mixture was stirred at room temperature for 4 hours. The solvent was then removed by evaporation under reduced pressure and the residue was treated with aqueous sodium hydroxide solution (1N) until solution was at pH=7. A further portion of aqueous sodium hydroxide solution (1N, 5 ml) was added and the solution was stirred at room temperature for 72 hours. The reaction solution was then submitted to ion exchange chromatography (DOWEX® 50WX8-200) eluting with deionized water:0.88 ammonia (97:3). The solvent was removed by evaporation under reduced pressure to afford a white solid residue. This material was dissolved in deionized water:methanol (95:5) and was further purified using MCI™ gel chromatography, eluting with deionized water:methanol (95:5) to afford the title compound, 4 mg, 6% yield.

$^1$H-NMR (CD$_3$OD, 300 MHz) δ: 2.74–2.98 (m, 4H), 3.13 (m, 1H), 3.35 (m, 2H), 6.95 (s, 2H).

Example 14

(2S)-2-[(2-Aminoethyl)amino]-3-(1H-imidazol-2-yl)
propanoic acid

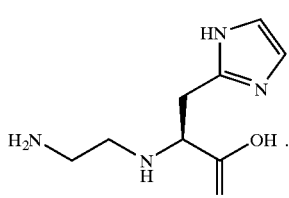

The product from Preparation 19 (200 mg, 0.45 mmol) was treated with aqueous hydrochloric acid (6N, 4 ml) and heated at reflux for 3 hours. The solvent was then removed by evaporation under reduced pressure and the residue was purified by ion exchange chromatography (DOWEX® 50WX8-200) eluting with an elution gradient of deionized water:0.88 ammonia (100:0 to 97:3). The isolated material was then freeze-dried to afford the title compound as a foam, 62 mg, 69% yield.

$^1$H-NMR (CD$_3$OD, 300 MHz) δ: 2.71–2.98 (m, 4H), 3.13 (m, 1H), 3.34 (m, 2H), 6.92 (s, 2H).

HRMS: m/z 199.1184 (MH$^+$), calcd 199.1190.

Example 15

(2S)-2-{[(1R or S)-1-(Aminomethyl)propyl]amino}-3-(1H-imidazol-4-yl)propanoic acid

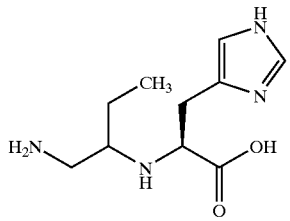

Trifluoroacetic acid was added dropwise to a stirred solution of the product from Preparation 21 (91 mg, 0.26 mmol) in dichloromethane (1 ml) and the mixture was stirred at room temperature for 17 hours under a nitrogen atmosphere. The solvent was then removed by evaporation under reduced pressure and the residue was azeotroped with toluene. The resultant material was dissolved in aqueous sodium hydroxide solution (5 ml, 2N) and stirred at room temperature for 72 hours. Solution was then purified by ion exchange chromatography (DOWEX® 50WX8-200), eluting with a solvent gradient of deionized water:0.88 ammonia (100:0 to 95:5), to afford the title compound, 37.3 mg, 62% yield.

$^1$H-NMR (CD$_3$OD, 400 MHz) δ: 0.81 (t, 3H), 1.37 (m, 1H), 1.50 (m, 1H), 2.62 (m, 1H), 2.67 (m, 1H), 2.78 (m, 1H), 2.90 (dd, 1H), 2.98 (dd, 1H), 3.33 (dd, 1H), 6.87 (s, 1H), 7.57 (s, 1H).

HRMS: m/z 227.1511 (MH$^+$), calcd 227.1503.

Example 16

(2S)-2-{[(1S or R)-1-(Aminomethyl)propyl]amino}-3-(1H-imidazol-4-yl)propanoic acid

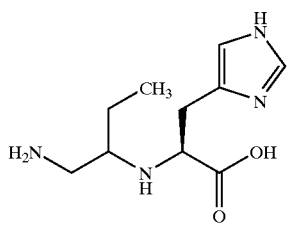

Trifluoroacetic acid was added dropwise to a stirred solution the product from Preparation 22 (167 mg, 0.49 mmol) in dichloromethane (1 ml) and the mixture was stirred at room temperature for 17 hours under a nitrogen atmosphere. Solvent was removed by evaporation under reduced pressure and residue azeotroped with toluene. The resultant material was dissolved in aqueous sodium hydroxide solution (5 ml, 2N) and stirred at room temperature for 72 hours. Solution was then purified by ion exchange chromatography (DOWEX® 50WX8-200) eluting with a solvent gradient of deionized water:0.88 ammonia (100:0 to 95:5) to afford the title compound, 38.7 mg, 35% yield.

$^1$H-NMR (CD$_3$OD, 400 MHz) δ: 0.73 (t, 3H), 1.35 (m, 2H), 2.43 (m, 1H), 2.53 (t, 1H), 2.70 (m, 1H), 2.95 (dd, 1H), 3.10 (dd, 1H), 3.40 (dd, 1H), 6.90 (s, 1H), 7.60 (s, 1H).

HRMS: m/z 227.1500 (MH$^+$), calcd 227.1502.

Example 17

(2S)-2-{[(1RS)-1-(Aminomethyl)-2-methylpropyl]amino}-3-(1H-imidazol-4-yl)propanoic acid

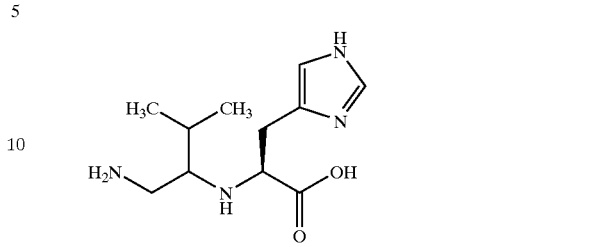

Trifluoroacetic acid (2 ml) was added to a stirred solution of the product from Preparation 23 (100 mg, 0.28 mmol) in dichloromethane (1 ml) and the mixture was stirred at room temperature for 17 hours. The solvent was then removed by evaporation under reduced pressure and the residue azeotroped with toluene. The residue was then dissolved in aqueous sodium hydroxide solution (2M, 2 ml) and stirred at room temperature for 72 hours. The solution was then purified by ion exchange chromatography (DOWEX® 50WX8-200) eluting with a solvent gradient of deionized water:0.88 ammonia (100:0 to 97:3). The isolated material (35 mg) was further purified by chromatography on reverse phase silica gel (C18 Sep-Pak®), eluting with deionized water, and then freeze-dried to afford the title compound (mixture of diastereoisomers), 20 mg, 30% yield.

$^1$H-NMR (CD$_3$OD, 300 MHz), mixture of diastereoisomers, δ: 0.67–0.90 (4×d, 6H), 2.40–3.40 (m, 7H), 6.85–6.95 (2×s, 1H), 7.72–7.62 (2×s, 1H).

HRMS: m/z 241.1661 (MH$^+$), calcd 241.1659.

TLC: methanol:ethyl acetate:0.88 ammonia:acetic acid::water (60:12:4:4:8) Rf=0.52 and 0.44.

Example 18

(2S)-2-{[(1RS)-2-Amino-1-benzylethyl]amino}-3-(1H-imidazol-4-yl)propanoic acid

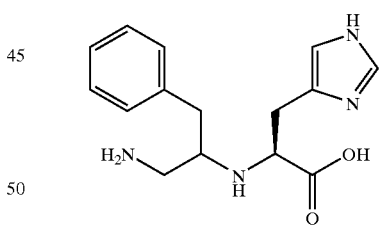

Trifluoroacetic acid (2 ml) was added to a stirred solution of the product from Preparation 24 (100 mg, 0.25 mmol) in dichloromethane (1 ml) and stirred at room temperature for 17 hours. The solvent was then removed by evaporation under reduced pressure and the residue azeotroped with toluene. The residue was dissolved in aqueous sodium hydroxide solution (2N, 2 ml) and stirred at room temperature for 17 hours. The solution was then purified by ion exchange chromatography (DOWEX® 50WX8-200) eluting with a solvent gradient of deionized water:0.88 ammonia (100:0 to 97:3) and isolated material was freeze-dried to afford the title compound, 41 mg, 58% yield.

$^1$H-NMR (CD$_3$OD, 300 MHz) δ: 2.48–2.72 (m, 2H), 2.77–3.10 (m, 3H), 3.25–3.47 (2×m, 1H), 3.31 (d, 2H), 6.80

(2×s, 1H), 6.91 (d, 1H), 7.10–7.30 (m, 4H), 7.55–7.63 (2×s, 1H).

HRMS : m/z 289.1662 (MH⁺), calcd 289.1659.

Example 19

(2S)-3-(1H-Imidazol-4-yl)-2-[(3RS)-pyrrolidinylamino)]propanoic acid

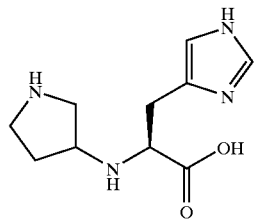

Aqueous sodium hydroxide solution (1.7 ml, 5N) was added dropwise to a stirred solution of the product from Preparation 20 (200 mg, 0.8 mmol) in deionized water (20 ml) and the solution was stirred at room temperature overnight. The solution was then purified by ion exchange chromatography (DOWEX® 50WX8-200) eluting with a solvent gradient of deionized water:0.88 ammonia (100:0 to 95:5) to afford the title compound as a pink foam, 90 mg, 50% yield.

¹H-NMR (D₂O, 300 MHz), mixture of diastereoisomers, δ: 1.67 (m, 1H), 2.05 (m, 1H), 2.70 (m, 2H), 2.90 (m, 1H), 3.05–3.38 (m, 5H), 6.69 (s, 1H), 7.59 (s, 1H).

LRMS: m/z 225.3 (MH⁺)

[α]$_D$=+1.57 (c 0.076, deionized water)

Example 20

(2S)-2-{[(1R,2S)-2-Amino-1-methylpropyl]amino}-3-(1H-imidazol-4-yl)propanoic acid

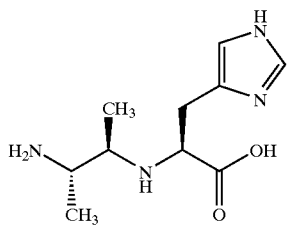

Aqueous sodium hydroxide solution (2 ml, 2N) was added to a stirred solution of the product from Preparation 26 (260 mg, 7.64 mmol) in dioxane (2 ml) and the mixture was stirred for 2.5 hours at room temperature. Aqueous hydrochloric acid (50% by volume, 4 ml) was added and the mixture was stirred at room temperature for 17 hours. The solution was then purified by ion exchange chromatography (DOWEX® 50WX8-200) eluting with a solvent gradient of deionized water:0.88 ammonia (100:0 to 97:3) to afford a white solid which was dissolved in deionized water and further purified by chromatography on reverse phase silica gel (C18 Sep-Pak®), eluting with deionized water, to afford the title compound, 15 mg, 9% yield.

¹H-NMR (CD₃OD, 300 MHz) δ: 0.93 (d, 3H), 1.17 (d, 3H), 2.62–2.80 (m, 2H), 3.08 (m, 1H), 3.20 (m, 1H), 3.37 (m, 1H), 6.92 (s, 1H), 7.61 (s, 1H).

HRMS: m/z 227.1506 (MH⁺), calcd 227.1502.

Example 21

(2S)-2-[(2-Aminoethyl)(methyl)amino]-3-(1H-imidazol-4-yl)propanoic acid

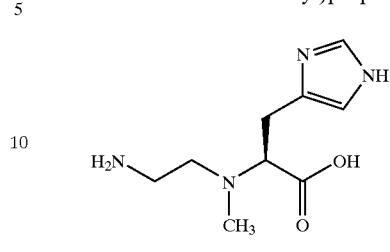

Trifluoroacetic acid (10 ml) was added to a stirred solution of the product from Preparation 27 (900 mg, 2.8 mmol) in methanol:deionized water (10 ml:8 ml) and the mixture was stirred for 2 hours. The solvent was removed by evaporation under reduced pressure to afford a light brown oil which was dissolved in excess aqueous sodium hydroxide solution (1N) and stirred for 17 hours. The solution was concentrated under reduced pressure and purified by ion exchange chromatography (DOWEX® 50WX8-200) eluting with a solvent gradient of deionized water:0.88 ammonia (100:0 to 96:4) to afford the title compound as a white foam, 381 mg, 60% yield.

¹H-NMR (D₂O, 300 MHz) δ: 2.25 (s, 3H), 2.50 (m, 1H), 2.60–3.37 (m, 6H), 6.78 (s, 1H), 7.58 (s, 1H).

Example 22

(2S)-3-(1H-Imidazol-4-yl)-2-(1-piperazinyl)propanoic acid

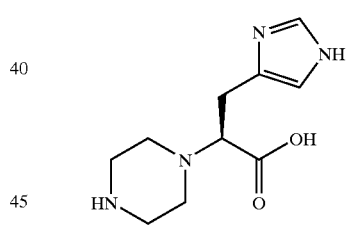

Aqueous sodium hydroxide solution (5N, 170 μl) was added to a stirred solution of the product from Preparation 28 (50 mg, 0.012 mmol) in water (a few drops) and the solution was stirred at room temperature for 18 hours. The solution was then submitted to ion exchange chromatography (DOWEX® 50WX8-200), eluting with a solvent gradient of deionized water:0.88 ammonia (100:0 to 95:5), and the solvent then removed by evaporation under reduced pressure. The residue was suspended in diethyl ether and then re-evaporated to afford the title compound as a white solid, 17 mg, 73% yield.

¹H-NMR (D₂O, 300 MHz) δ: 2.62–2.98 (m, 6H), 3.05–3.30 (m, 5H), 6.80 (s, 1H), 7.60 (s, 1H).

HRMS: m/z 225.1338 (MH⁺), calcd 225.1346.

[α]$_D$=+14.84 (c 0.062, deionized water)

TLC: methanol:ethyl acetate:0.88 ammonia:acetic acid:water (60:12:4:4:8) Rf=0.20.

Example 23

(2S)-2-(1,4-Diazepan-1-yl)-3-(1H-imidazol-4-yl)propanoic acid

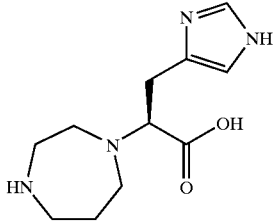

Homopiperazine (1.86 g, 18.6 mmol) was added to a stirred solution of the product from Preparation 61 (350 mg, 1.86 mmol) in acetonitrile (40 ml) and the solution was stirred for 2 hours at room temperature then heated at reflux for 18 hours. The solvent was removed under reduced pressure and the residue was dissolved in dichloromethane and washed with water (3×20ml). The organic phase was concentrated under reduced pressure and the resultant oil was dissolved in deionized water and purified by ion exchange chromatography (DOWEX® 50WX8-200) eluting with a solvent gradient of deionized water:0.88 ammonia (100:0 to 95:5) to afford the title compound as a beige solid, 300 mg, 68% yield.

$^1$H-NMR (D$_2$O, 300 MHz) δ: 1.83 (m, 2H), 2.70–3.23 (m, 10H), 3.40 (t, 1H), 6.80 (s, 1H), 7.60 (s, 1H).

LRMS: m/z 239.2 (MH$^+$)

Anal. Found: C, 50.79; H, 7.85; N, 21.31. C$_{11}$H$_{18}$N$_4$O$_2$.1.25H$_2$O requires C, 50.66; H, 7.92; N, 21.48%.

[α]$_D$=+2.47 (c 0.24, deionized water)

Example 24

(2S)-2-[(2-Aminoethyl)amino]-3-(1-ethyl-1H-imidazol-4-yl)propanoic acid

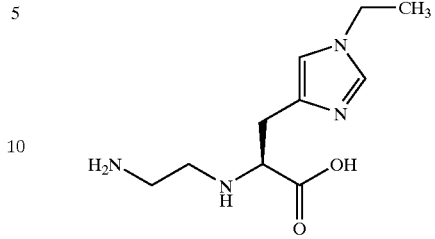

Concentrated hydrochloric acid (5 ml) was added to a stirred solution of the product from Preparation 30 (118 mg, 0.32 mmol) in water (5 ml) and the mixture was heated at reflux for 17 hours. The mixture was allowed to cool to room temperature and the solvent was removed by evaporation under reduced pressure. The residue was purified by ion exchange chromatography (DOWEX® 50WX8-200) eluting with deionized water:0.88 ammonia (97:3). The isolated material was freeze-dried to afford the title compound, 34 mg, 47% yield.

$^1$H-NMR (CD$_3$OD, 300 MHz) δ: 1.40 (t, 3H), 2.75–3.02 (m, 6H), 3.33 (m, 1H), 3.98 (q, 2H), 6.95 (s, 1H), 7.53 (s, 1H).

HRMS : m/z 227.1492 (MH$^+$), calcd 227.1503.

Examples 25–40

The compounds of the following tabulated Examples of the general formula:

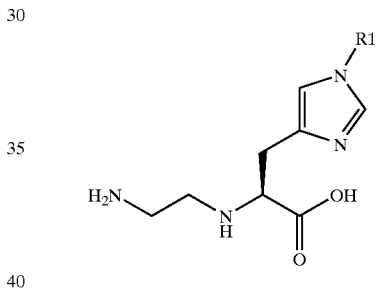

were prepared by a similar method to that of Example 24 using the corresponding products from Preparations 31–46.

| Example No. | R1 | Yield (%) | Analytical Data |
|---|---|---|---|
| 25[1] | H$_3$C-CH$_2$- | 55 | $^1$H-NMR(CD$_3$OD, 300 MHz) δ: 0.90 (t, 3H), 1.78(q, 2H), 2.77–3.01(m, 6H), 3.31(m, 1H), 3.90(t, 2H), 6.90 (s, 1H), 7.52(s, 1H). LRMS: m/z 241.1(MH$^+$) |
| 26[1] | H$_3$C-CH$_2$-CH$_2$- | 82 | $^1$H-NMR(CD$_3$OD, 300 MHz) δ: 0.70 (t, 3H), 1.05(q, 2H), 1.57(m, 2H), 2.57–2.73(m, 4H), 2.85(m, 2H), 3.08 (t, 1H), 3.78(t, 2H), 6.78(s, 1H), 7.42 (s, 1H). HRMS: m/z 255.1824(MH$^+$), calcd 255.1816. Anal. Found: C, 55.79; H, 8.65; N, 21.96. C$_{12}$H$_{22}$N$_4$O$_2$.0.22H$_2$O requires C, 55.80; H, 8.76; N, 21.69%. |

| Example No. | R1 | Yield (%) | Analytical Data |
|---|---|---|---|
| 27[1] | 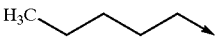 | 38 | $^1$H-NMR(CD$_3$OD, 300 MHz) δ: 0.90 (t, 3H), 1.20–1.40(m, 4H), 1.77(m, 2H), 2.78–3.05(m, 6H), 3.30(m, 1H), 3.93(t, 2H), 6.93(s, 1H), 7.57(s, 1H). HRMS: m/z 269.1978(MH$^+$), calcd 269.1972. Anal. Found: C, 54.21; H, 8.83; N, 19.32. C$_{13}$H$_{24}$N$_4$O$_2$.1.2H$_2$O requires C, 53.85; H, 9.18; N, 19.32%. |
| 28[2] | 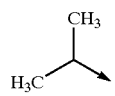 | 96 | $^1$H-NMR(CD$_3$OD, 300 MHz) δ:1.45 (d, 6H), 2.72–3.03(m, 6H), 3.33(m, 1H), 4.33(m, 1H), 7.00(s, 1H), 7.58 (s, 1H). HRMS: m/z 241.1662(MH$^+$), calcd 241.1659. |
| 29[2] | 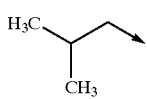 | 54 | $^1$H-NMR(CD$_3$OD, 300 MHz) δ: 0.90 (d, 6H), 2.01(m, 1H), 2.77–3.03 (m, 6H), 3.33(m, 1H), 3.77(d, 2H), 6.90 (s, 1H), 7.50(s, 1H). HRMS: m/z 255.1825(MH$^+$), calcd 255.1816. |
| 30[1] | 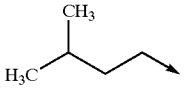 | 65 | $^1$H-NMR(CD$_3$OD, 300 MHz) δ: 0.93 (d, 6H), 1.55(m, 1H), 1.67(m, 2H), 2.73–3.05(m, 6H), 3.33(m, 1H), 3.97 (t, 2H), 6.93(s, 1H), 7.53(s, 1H). HRMS: m/z 269.1980(MH$^+$), calcd 269.1972. Anal. Found: C, 51.94; H, 8.99; N, 18.53. C$_{13}$H$_{24}$N$_4$O$_2$.1.80H$_2$O requires C, 51.60; H, 9.26; N, 18.52%. |
| 31[1,3] | 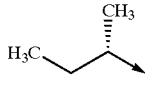 | 3 | $^1$H-NMR(D$_2$O, 400 MHz) δ: 0.66(t, 3H), 1.34(d, 3H), 1.66(m, 2H), 2.66–2.84(m, 4H), 2.95(m, 2H), 3.29(t, 1H), 4.05(m, 1H), 6.94(s, 1H), 7.61 (s, 1H). HRMS: m/z 255.1827(MH$^+$), calcd 255.1816. |
| 32[1,4] | 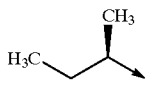 | 27 | $^1$H-NMR(D$_2$O, 400 MHz) δ: 0.66(t, 3H), 1.35(d, 3H), 1.66(m, 2H), 2.68–2.82(m, 4H), 2.94(m, 2H), 3.29(t, 1H), 4.05(m, 1H), 6.94(s, 1H), 7.60 (s, 1H). HRMS: m/z 255.1825(MH$^+$), calcd 255.1816. |
| 33 | 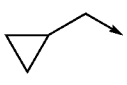 | 10 | $^1$H-NMR(CD$_3$OD, 300 MHz) δ: 0.37 (m, 2H), 0.60(m, 2H), 1.20(m, 1H), 2.75–3.03(m, 6H), 3.33(m, 1H), 3.80 (d, 2H), 7.00(s, 1H), 7.58(s, 1H). HRMS: m/z 253.1661(MH$^+$), calcd 253.1659. |
| 34[1] |  | 53 | $^1$H-NMR(CD$_3$OD, 300 MHz) δ:1.70–2.10(m, 6H), 2.60–3.10(m, 7H), 3.35 (m, 1H), 3.95(d, 2H), 6.90(s, 1H), 7.50(s, 1H). HRMS: m/z 267.1822(MH$^+$), calcd 267.1816. Anal. Found: C, 53.74; H, 8.43; N, 19.30. C$_{13}$H$_{22}$N$_4$O$_2$.1.3H$_2$O requires C, 53.92; H, 8.50; N, 19.34%. |
| 35 | 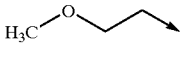 | 2.5 | $^1$H-NMR(CD$_3$OD, 300 MHz) δ: 2.75–2.93(m, 5H), 2.98(dd, 1H), 3.33 (s+m, 4H), 3.62(t, 2H), 4.10(t, 2H), 6.95(s, 1H), 7.53(s, 1H). HRMS: m/z 257.1607(MH$^+$), calcd 257.1608. |

-continued

| Example No. | R1 | Yield (%) | Analytical Data |
|---|---|---|---|
| 36[1] | 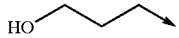 | 55 | $^1$H-NMR(D$_2$O, 300 MHZ) δ: 1.90(m, 2H), 2.64–2.82(m, 4H), 2.97(m, 2H), 3.28(t, 1H), 3.44(t, 2H), 3.98(t, 2H), 6.88(s, 1H), 7.57(s, 1H). HRMS: m/z 257.1618(MH$^+$), calcd 257.1608. Anal. Found: C, 47.43; H, 7.81; N, 19.98. C$_{11}$H$_{20}$N$_4$O$_3$.1.3 H$_2$O requires C, 47.23; H, 8.14; N, 20.03%. |
| 37[2] | 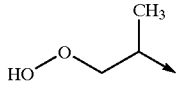 | 28 | $^1$H-NMR(CD$_3$OD, 400 MHz) δ: 1.43 (d, 3H), 2.82(m, 3H), 2.90(m, 2H), 3.00(dd, 1H), 3.30(s, 3H), 3.35(m, 1H), 3.55(d, 2H), 4.38(q, 1H), 7.00 (s, 1H), 7.58(s, 1H). HRMS: m/z 271.1770(MH$^+$), calcd 271.1765. |
| 38[1] | 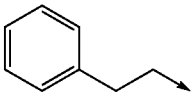 | 42 | $^1$H-NMR(CD$_3$OD, 400 MHz) δ: 2.61–3.13(m, 8H), 3.31(m, 1H), 4.16(t, 2H), 6.90(s, 1H), 7.11(m, 2H), 7.13–7.40(m, 4H). HRMS: m/z 303.1823 (MH$^+$), calcd 303.1816. Anal. Found: C, 58.13; H, 7.51; N, 17.06. C$_{16}$H$_{22}$N$_4$O$_2$.1.6H$_2$O requires C, 58.02; H, 7.67; N, 16.92%. |
| 39 | 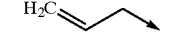 | 64 | $^1$H-NMR(CD$_3$OD, 400 MHz) δ: 2.78–3.01(m, 5H), 3.34(m, 2H), 4.58(d, 2H), 5.19(d, 1H), 5.23(d, 1H), 5.99 (m, 1H), 6.92(s, 1H), 7.54(s, 1H). HRMS: m/z 239.1510 (MH$^+$), calcd 239.1503. Anal. Found: C, 50.64; H, 7.56; N, 21.03. C$_{11}$H$_{18}$N$_4$O$_2$.1.3H$_2$O requires C, 50.48; H, 7.93; N, 21.41%. |
| 40 | 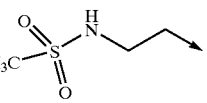 | 14 | $^1$H-NMR(CD$_3$OD, 400 MHz) δ: 2.78–3.00(m, 9H), 3.35(m, 1H), 3.39(t, 2H), 4.06(t, 2H), 6.97(s, 1H), 7.58 (s, 1H). HRMS m/z 320.1391(MH$^+$), calcd 320.1387. |

Footnotes:
[1]Concentrated sulfuric acid (4M) used instead of concentrated hydrochloric acid (6M).
[2]Sulfuric acid (2M) used instead of concentrated hydrochloric acid (6M).
[3]The isolated product was further purified using a 5 μm Hypersil Hypercarb ™ column, using an elution gradient of water:trifluoroacetic acid:acetonitrile (100:0.1:0 to 50:0.05:50), and then re-subjected to ion-exchange chromatography (as in Example 24).
[4]The isolated product was further purified as described in note (3) but using an elution gradient of water:trifluoroacetic acid:methanol (100:0.1:0 to 50:0.05:50).

Example 41

(2S)-2-[(2-Aminoethyl)amino]-3-[1-(carboxymethyl)-1H-imidazol-4-yl]propanoic acid

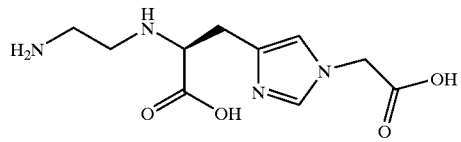

The product from Preparation 47 (145 mg, 0.296 mmol) was dissolved in concentrated sulfuric acid (4 ml) and the solution heated under reflux for 18 hours. The cooled mixture was purified directly by ion exchange chromatography (DOWEX® 50WX8-200), eluting with 0.88 ammonia:water (3:97). The resulting oil was triturated with methanol, to give a solid which was freeze-dried to afford the title compound as a white foam, 61 mg, 77% yield.

$^1$H-NMR (D$_2$O, 400 MHz) δ: 2.80 (m, 2H), 2.88 (m, 2H), 2.98 (m, 2H), 3.40 (m, 1H), 4.52 (s, 2H), 6.92 (s, 1H), 7.81 (s, 1H).
HRMS: m/z 257.1255 (MH$^+$), calcd 257.1245.
Anal. Found: C, 42.66; H, 6.63; N, 20.29. C$_{10}$H$_{16}$N$_4$O$_4$.1.3H$_2$O requires C, 42.95; H, 6.70; N, 20.03%.

Example 42

(2S)-3-[(1-n-propyl-1H-imidazol-4-yl)methyl]-2-piperidinone

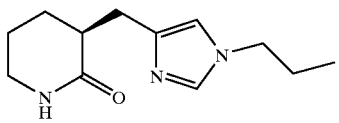

The compound from Preparation 11 (500 mg, 1.6 mmol) in dichloromethane (15 ml) was treated with trifluoroacetic acid (3 ml) and the resultant solution was stirred at room temperature for 2 hours. The reaction mixture was then concentrated under reduced pressure and the residue neutralized with saturated aqueous sodium bicarbonate solution. The resultant mixture was then concentrated to dryness under reduced pressure and the residue purified by column chromatography on silica gel using an elution gradient of dichloromethane:methanol:0.88 ammonia (99.8:0:0.2 to 94.8:5:0.2) to give the title compound as an oil, 250 mg, 73% yield.

$^1$H-NMR (CDCl$_3$, 400 MHz) δ: 0.87 (t, 3H), 1.39–1.84 (m, 5H), 1.90 (m, 1H), 2.60 (m, 1H), 2.74 (dd, 1H), 3.13 (dd, 1H), 3.21 (m, 2H), 3.77 (t, 2H), 5.61 (br s, 1H), 6.65 (s, 1H), 7.31 (s, 1H).

LRMS: m/z 222 (MH$^+$)

Anal. Found: C, 61.44; H, 8.85; N, 17.86. C$_{12}$H$_{19}$N$_3$O.0.75H$_2$O requires C, 61.38; H, 8.80; N, 17.89%.

$[α]_D$=−51.6 (c 0.095, methanol)

Example 43

(2S)-2-[(2-Aminoethyl)amino]-3-(1-methyl-1H-imidazol-4-yl)propanoic acid

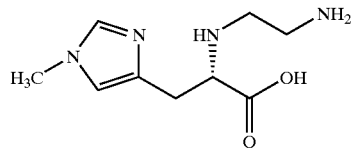

2M Sodium hydroxide solution (0.61 ml, 1.22 mmol) was added to a solution of the protected amino acid from preparation 90 (200 mg, 0.61 mmol) in dioxan (2 ml), and the reaction stirred at room temperature for 18 hours. Concentrated hydrochloric acid (2 ml) was carefully added, and the solution stirred for a further 24 hours, then concentrated under reduced pressure. The residue was dissolved in water, and purified by column chromatography on Amberlyst® 15 ion-exchange resin, eluting with 5% aqueous ammonia solution. The product was obtained after freeze-drying as a gum, 80 mg, 55% yield.

$^1$H-NMR (D$_2$O, 400 MHz) δ: 2.61–2.79 (m, 4H), 2.90 (m, 2H), 3.22 (m, 1H), 3.54 (s, 3H), 6.79 (s, 1H), 7.42 (s, 1H).

LRMS (ES$^-$): m/z 211 (M−H)$^-$ $[α]_D$=−5.83 (c 0.12, methanol) Anal Found: C, 45.63; H, 7.68; N, 23.15. C$_9$H$_{16}$N$_4$O$_2$.1.45H$_2$O requires C, 45.35; H, 7.99; N, 23.50%.

Examples 44 to 47

The following examples of general structure:

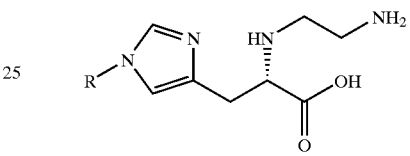

were prepared from the appropriate protected amino acids (Preparations 91–94), following a similar procedure to that described in Example 43.

| Example No. | R1 | Yield (%) | Analytical Data |
|---|---|---|---|
| 44[1] | ![F3C-CH2CH2CH2-] | 48 white solid | $^1$H-NMR(D$_2$O, 400 MHz) δ: 1.99(m, 2H), 2.06(m, 2H), 2.68–2.83 (m, 4H), 2.98(t, 2H), 3.32(t, 1H), 3.98(t, 2H), 6.90(s, 1H), 7.58(s, 1H). LRMS: m/z 309 (MH$^+$) $[α]_D$ = −0.75(c 0.16, methanol) Anal. Found: C, 45.25; H, 6.31; N, 17.53. C$_{12}$H$_{19}$F$_3$N$_4$O$_2$.0.5H$_2$O requires C, 45.42; H, 6.35; N, 17.66%. |
| 45[2] | ![thiazole-CH2-] | 49 white solid | $^1$H-NMR(D$_2$O, 400 MHz) δ: 2.63–2.81 (m, 4H), 2.95(m, 2H), 3.24(m, 1H), 5.21(s, 2H), 6.85(s, 1H), 7.41(s, 1H), 7.62(s, 1H), 8.84(s, 1H). LRMS(ES$^-$): m/z 294(M-H)$^-$ $[α]_D$ = −5.00(c 0.10, methanol) Anal. Found: C, 46.27; H, 5.81; N, 21.91. C$_{12}$H$_{17}$N$_5$O$_2$S.1.0H$_2$O requires C, 45.94; H, 6.12; N, 22.32%. |
| 46 | ![pyridyl-CH2CH2-] | 52 solid | $^1$H-NMR(D$_2$O, 400 MHz) δ: 2.28(dd, 1H), 2.68(m, 3H), 2.89(t, 2H), 3.08 (t, 2H), 3.18(t, 1H), 4.21(t, 2H), 6.70 (s, 1H), 6.99(d, 1H), 7.12(s, 1H), 7.18(dd, 1H), 7.60(dd, 1H), 8.30 (d, 1H). LRMS: m/z 326(MNa$^+$) $[α]_D$ = −4.17(c 0.12, methanol) Anal. Found: C, 56.28; H, 7.15; N, 21.68. C$_{15}$H$_{21}$N$_5$O$_2$.1.0H$_2$O requiresC, 56.06 H, 7.21; N, 21.79%. |

-continued

| Example No. | R1 | Yield (%) | Analytical Data |
|---|---|---|---|
| 47 | 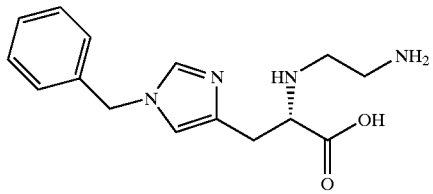 | 65 beige solid | ¹H-NMR(D₂O, 400 MHz) δ: 2.70–2.90 (m, 4H), 2.95(m, 2H), 3.35(t, 1H), 7.22(s, 1H), 7.32(m, 1H), 7.41(m, 4H), 7.92(s, 1H). LRMS: m/z 297 (MNa⁺) [α]$_D$ = +8.45 (c 0.09, methanol) Anal. Found: C, 55.68; H, 6.95; N, 18.29. C$_{14}$H$_{18}$N$_4$O$_2$.1.5H$_2$O requiresC, 55.80; H, 7.02; N, 18.59%. |

¹Water was used as the column eluant
²Product was purified on DOWEX® 50WX8-200 ion-exchange resin, using water:0.88 ammonia (95:5) as eluant.

Example 48

(2S)-2-[(2-Aminoethyl)amino]-3-(1-benzyl-1H-imidazol-4-yl)propanoic acid

A solution of the compound from preparation 95 (288 mg, 0.57 mmol) in 4M sulphuric acid (10 ml), was heated at 115° C. for 36 hours. The cooled solution was neutralized using 1M sodium hydroxide solution, then passed through an Amberlyst® 15 ion exchange column, eluting with 5% aqueous ammonia. The product was obtained as a gum after freeze-drying, 70 mg, 39% yield.

¹H-NMR (D₂O, 400MHz) δ: 2.40 (m, 1H), 2.48 (m, 1H), 2.58 (m, 4H), 3.14 (t, 1H), 5.00 (s, 2H), 6.77 (s, 1H), 7.14 (d, 2H), 7.22 (m, 3H), 7.50 (s 1H).

LRMS: m/z 289 (MH⁺)

[α]$_D$=+1.00 (c 0.14, methanol)

Anal. Found: C, 56.96; H, 7.17; N, 17.63. C$_{15}$H$_{20}$N$_4$O$_2$.1.5H$_2$O requires C, 57.13; H, 7.35; N, 17.77%.

Example 49

(±)-5-Amino-2-[(1-isopentyl-1H-imidazol-4-yl) methyl]pentanoic acid

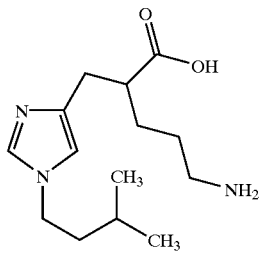

A solution of sodium hydroxide (192 mg, 4.80 mmol) in water (6 ml) was added to a solution of the compound from preparation 105 (420 mg, 1.20 mmol) in tetrahydrofuran (10 ml), and the reaction stirred vigorously for 72 hours. Concentrated hydrochloric acid (6 ml) was carefully added, and the mixture stirred at room temperature for 3 hours, then concentrated under reduced pressure. The residue was dissolved in water (50 ml), and the solution purified by column chromatography on Amberlyst® 15 ion-exchange resin, using an elution gradient of water:0.88 ammonia (100:0 to 98:2) to afford the title compound, 120 mg, 35% yield.

¹H-NMR (D₂O, 400 MHz) δ: 0.72 (d, 6H), 1.23–1.40 (m, 3H), 1.46 (m, 4H), 2.30–2.43 (m, 2H), 2.59 (dd, 1H), 2.79 (m, 2H), 3.80 (t, 2H), 6.76 (s, 1H), 7.42 (s, 1H).

LRMS (ES⁻): m/z 266 (M−H)⁻

Anal. Found: C, 58.60; H, 9.62; N, 14.56. C$_{14}$H$_{25}$N$_3$O$_2$.1.0H$_2$O requires C, 58.92; H, 9.54; N, 14.72%.

Example 50

(±)-2-[(1-Isopentyl-1H-imidazol-4-yl)methyl]-5-(methylamino)pentanoic acid

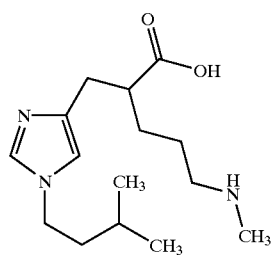

A solution of the compound from preparation 106 (170 mg, 0.65 mmol) in dioxan (1 ml) and concentrated hydrochloric acid (2 ml) was heated at reflux for 18 hours. The cooled mixture was concentrated under reduced pressure at room temperature, and the residue dissolved in water (50 ml). The solution was purified by column chromatography on Amberlyst® 15 ion-exchange resin, using an elution gradient of water:0.88 ammonia (100:0 to 98:2). Freeze drying afforded the title compound as a brown solid, 120 mg, 66% yield.

¹H-NMR (D₂O, 400 MHz) δ: 0.75 (d, 6H), 1.25–1.42 (m, 3H), 1.50 (m, 4H), 2.34–2.44 (m, 2H), 2.55 (s, 3H), 2.62 (dd, 1H), 2.86 (m, 2H), 3.82 (t, 2H), 6.78 (s, 1H), 7.43 (s, 1H).

LRMS: m/z 282.2 (MH⁺)

Anal. Found: C, 58.56; H, 9.73; N, 13.61. C$_{15}$H$_{27}$N$_3$O$_2$.1.45H$_2$O requires C, 58.59; H, 9.80; N, 13.66%.

Example 51

(±)-5-Amino-2-[(1-phenyl-1H-imidazol-4-yl)methyl]pentanoic acid

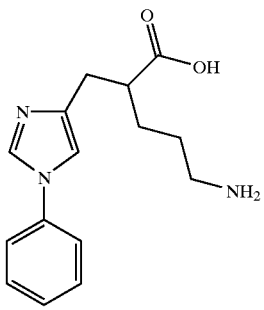

A solution of lithium hydroxide (2 ml, 1M, 2 mmol) was added to a solution of the compound from preparation 108 (240 mg, 0.68 mmol) in tetrahydrofuran (2 ml), and the reaction stirred at room temperature for 5 hours. Concentrated hydrochloric acid (2 ml) was added carefully, and the reaction stirred at room temperature for 18 hours. The solution was evaporated under reduced pressure, the residue dissolved in water, and the solution purified by column chromatography on Amberlyst® 15 ion-exchange resin using an elution gradient of water:0.88 ammonia (100:0 to 95:5) to afford the title compound as a white foam, 88 mg, 45% yield.

$^1$H-NMR (D$_2$O, 400 MHz) δ: 1.43 (m, 2H), 1.54 (m, 2H), 2.42–2.59 (m, 2H), 2.74 (dd, 1H), 2.83 (m, 2H), 7.18 (s, 1H), 7.32 (m, 1H), 7.40 (m, 4H), 7.88 (s, 1H).

LRMS: m/z 296 (MNa$^+$)

Anal. Found: C, 62.21; H, 7.01; N, 14.55. C$_{15}$H$_{19}$N$_3$O$_2$.1.0H$_2$O requires C, 61.84; H, 7.27; N, 14.42%.

Preparation of Intermediates:

Preparation 1

(±)-Ethyl 2-[(1-{[2-(trimethylsilyl)ethoxy]methyl}-1H-imidazol-4-yl)methyl]-5-(tritylamino)pentanoate

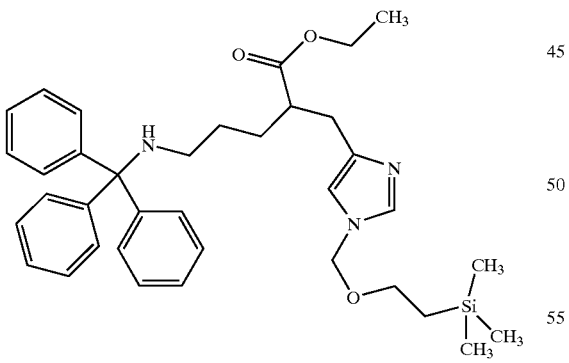

A mixture of the alkenes from Preparation 49 (460 mg, 0.77 mmol) and 10% palladium on charcoal (100 mg) in ethanol (25 ml) was hydrogenated at 1.5 atm and room temperature for 72 hours. The reaction mixture was filtered through Arbocel™, washing through with ethanol (200 ml), and the filtrate concentrated under reduced pressure. The residual oil was purified by column chromatography on silica gel using ethyl acetate:pentane (50:50) as eluant, to give the title compound, 150 mg, 33% yield.

$^1$H-NMR (CDCl$_3$, 400 MHz) δ: −0.02 (s, 9H), 0.95 (t, 2H), 1.18 (t, 3H), 1.46 (m, 2H), 1.45–1.70 (m, 2H), 2.09 (m, 2H), 2.64–2.79 (m, 2H), 2.90 (dd, 1H), 3.42 (t, 2H), 4.09 (q, 2H), 5.18 (s, 2H), 6.75 (s, 1H), 7.17 (m, 3H), 7.22 (m, 7H), 7.42 (d, 6H).

Preparation 2

(±)-Ethyl 2-[(1-n-propyl-1H-imidazol-4-yl)methyl]-5-(tritylamino)pentanoate

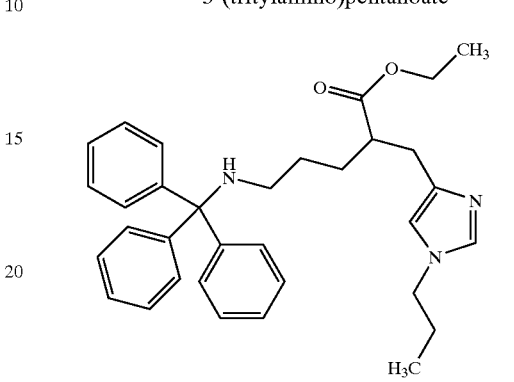

Sodium borohydride (7.2 g, 190 mmol) was added portionwise over 2 hours to a solution of alkenes from Preparation 50 (3.2 g, 6.3 mmol) and copper (I) chloride (928 mg, 9.5 mmol) in methanol (120 ml), so as to maintain the reaction temperature at about 45° C., and the reaction stirred at this temperature for 2 hours, (two additional portions of copper (I) chloride (310 mg, 3.1 mmol) were added after approx 40 and 80 minutes). The reaction mixture was filtered through Arbocel™ and the filtrate concentrated under reduced pressure. The residue was partitioned between ethyl acetate and water, the layers separated, and the aqueous phase extracted with ethyl acetate (2×). The combined organic extracts were dried (Na$_2$SO$_4$) and concentrated under reduced pressure. The crude product was purified by column chromatography on silica gel using an elution gradient of ethyl acetate:pentane (50:50 to 100:0) to give the title compound, 2 g, 62% yield.

$^1$H-NMR (CDCl$_3$, 300 MHz) δ: 0.88 (t, 3H), 1.19 (t, 3H), 1.55 (m, 4H), 1.76 (m, 2H), 2.08 (m, 2H), 2.62–2.80 (m, 2H), 2.86 (dd, 1H), 3.79 (t, 2H), 4.07 (q, 2H), 6.60 (s, 1H), 7.18 (m, 3H), 7.24 (m, 7H), 7.43 (d, 6H).

LRMS: m/z 510 (MH$^+$)

Preparation 3

(±)-6-[(tert-Butoxycarbonyl)amino]-2-[(1-n-propyl-1H-imidazol-4-yl)methyl]hexanoic acid

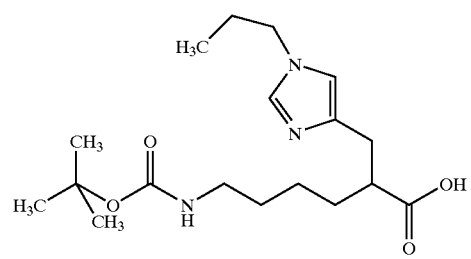

A solution of the compound from Preparation 4 (32 mg, 0.07 mmol) in tetrahydrofuran (2 ml) and ethanol (50 μl)

was added to a cooled (−78° C.) solution of sodium (20 mg, 0.87 mmol) in 0.88 ammonia (3 ml), and the solution stirred for 15 minutes, until the blue color disappeared. The reaction was allowed to warm to room temperature, the ammonia evaporated off and then the remaining solution was concentrated under reduced pressure. The crude product was purified by ion exchange chromatography on DOWEX® (50WX8-200) resin, eluting with a solvent gradient of water:0.88 ammonia (100:0 to 97:3), to give the title compound, 17 mg, 69% yield.

$^1$H-NMR (CD$_3$OD, 300 MHz) δ: 0.90 (t, 3H), 1.42 (m, 13H), 1.61 (m, 2H), 1.80 (m, 2H), 2.57–2.68 (m, 2H), 2.80–2.95 (m, 2H), 3.00 (m, 1H), 3.95 (t, 2H), 6.98 (s, 1H), 7.76 (s, 1H).

LRMS: m/z 354.3 (MH$^+$)

Preparation 4

Sodium 6-[benzyl(tert-butoxycarbonyl)amino]-2-[(1-n-propyl-1H-imidazol-4-yl)methyl]hexanoate

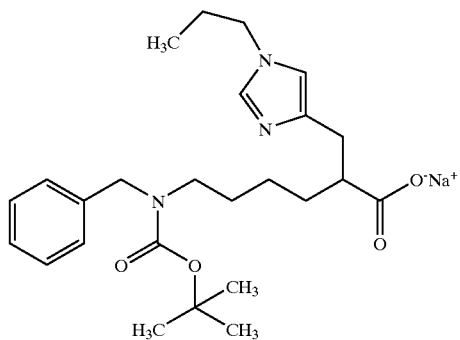

Aqueous sodium hydroxide solution (2 ml, 2N) was added to a solution of the ester from Preparation 5 (50 mg, 0.106 mmol) in dioxane (2 ml), and the reaction stirred at room temperature for 18 hours. The mixture was concentrated under reduced pressure and the residue purified by column chromatography on silica gel eluting with dichloromethane:methanol:0.88 ammonia (90:10:1), to give the title compound, 32 mg, 65% yield.

$^1$H-NMR (CD$_3$OD, 300 MHz) δ: 0.88 (t, 3H), 1.15–1.57 (m, 15H), 1.80 (m, 2H), 2.60 (m, 2H), 2.82 (m, 1H), 3.17 (m, 2H), 3.94 (t, 2H), 4.42 (s, 2H), 6.96 (s, 1H), 7.22 (m, 3H), 7.32 (m, 2H), 7.78 (br s, 1H).

LRMS: m/z 444.7 (MH$^+$)

Preparation 5

(±)-Ethyl 6-[benzyl(tert-butoxycarbonyl)amino]-2-[(1-n-propyl-1H-imidazol-4-yl)methyl]hexanoate

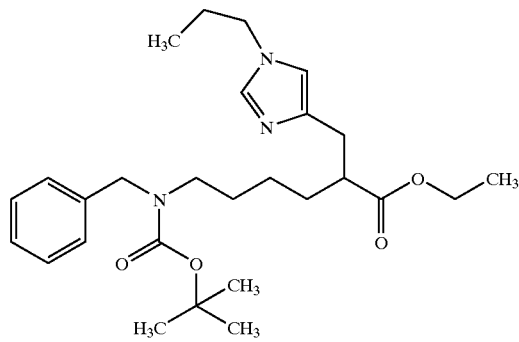

A mixture of the alkenes from Preparation 51 (620 mg, 1.32 mmol) and 10% palladium on charcoal (70 mg) in methanol (50 ml) was hydrogenated at 1 atm and room temperature for 4 hours. The reaction mixture was filtered through Arbocel™, and the filtrate concentrated under reduced pressure to give the title compound in quantitative yield as a clear gum, which was used without further purification.

$^1$H-NMR (CDCl$_3$, 300 MHz) δ: 0.90 (t, 3H), 1.18 (t, 3H), 1.24 (m, 2H), 1.38–1.66 (m, 13H), 1.78 (m, 2H), 2.61–2.80 (m, 2H), 2.86 (dd, 1H), 3.04–3.22 (m, 2H), 3.80 (t, 2H), 4.06 (q, 2H), 4.40 (br s, 2H), 6.61 (s, 1H), 7.18–7.37 (m, 6H).

LRMS: m/z 472.4 (MH$^+$)

Preparation 6 and Preparation 7

Ethyl (2R)-2-[(1-n-butyl-1H-imidazol-4-yl)methyl]-5-(tritylamino)pentanoate (6)

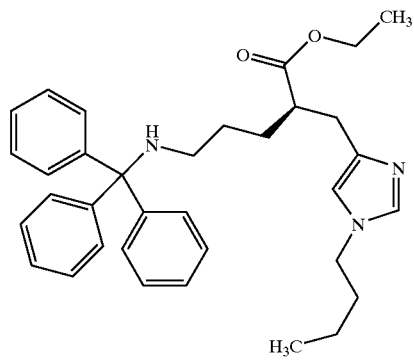

Ethyl (2S)-2-[(1-n-butyl-1H-imidazol-4-yl)methyl]-5-(tritylamino)pentanoate (7)

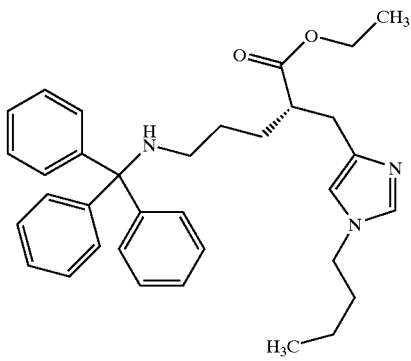

The racemic compound from Preparation 8 was resolved by HPLC using a Chiralcel® OD 250 column (20 mm), and hexane:ethanol:diethylamine (85:15:0.45) as eluant at a rate of 10 ml/minute, to afford the title compound of Preparation 6, 98.3% ee,
Retention time: 13.36 minutes,
$^1$H-NMR (CDCl$_3$, 300 MHz) δ: 0.92 (t, 3H), 1.20 (t, 3H), 1.28 (m, 2H), 1.45–1.78 (m, 6H), 2.10 (m, 2H), 2.62–2.79 (m, 2H), 2.88 (dd, 1H), 3.81 (t, 2H), 4.08 (q, 2H), 6.60 (s, 1H), 7.18 (m, 3H), 7.24 (m, 7H), 7.43 (d, 6H).
and the title compound of Preparation 7, 94.2%ee,
Retention time: 14.91 minutes.
$^1$H-NMR (CDCl$_3$, 300 MHz) δ: 0.92 (t, 3H), 1.20 (t, 3H), 1.28 (m, 2H), 1.45–1.78 (m, 6H), 2.10 (m, 2H), 2.62–2.79 (m, 2H), 2.88 (dd, 1H), 3.81 (t, 2H), 4.08 (q, 2H), 6.60 (s, 1H), 7.18 (m, 3H), 7.24 (m, 7H), 7.43 (d, 6H).

Preparation 8

(±)-Ethyl 2-[(1-n-butyl-1H-imidazol-4-yl)methyl]-5-(tritylamino)pentanoate

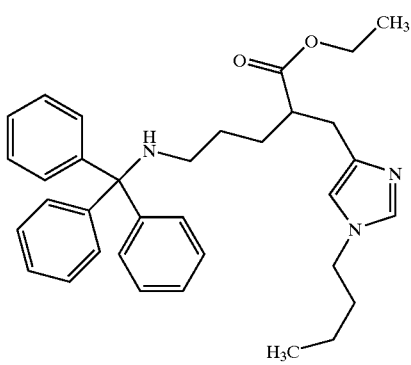

Sodium borohydride (871 mg, 23 mmol) was added portionwise over an hour to a solution of the alkene from Preparation 52 (400 mg, 0.76 mmol) and copper (I) chloride (112 mg, 1.15 mmol) in methanol (15 ml). TLC analysis showed starting material remaining, so additional copper (I) chloride (75 mg, 0.76 mmol) and sodium borohydride (290 mg, 7.7 mmol) were added, and the reaction stirred at room temperature for a further 2 hours. The reaction mixture was filtered through Arbocel™, the filtrate concentrated under reduced pressure and the residue partitioned between ethyl acetate and brine. The layers were separated, the aqueous phase extracted with ethyl acetate (2×), and the combined organic extracts dried (Na$_2$SO$_4$) and concentrated under reduced pressure, to give the title compound, 185 mg, 47% yield.

$^1$H-NMR (CDCl$_3$, 400 MHz) δ: 0.92 (t, 3H), 1.19 (t, 3H), 1.27 (m, 2H), 1.48–1.77 (m, 6H), 2.10 (m, 2H), 2.62–2.79 (m, 2H), 2.88 (dd, 1H), 3.82 (t, 2H), 4.08 (q, 2H), 6.60 (s, 1H), 7.17 (m, 3H), 7.24 (m, 7H), 7.43 (d, 6H).

Preparation 9

Lithium (2R)-5-[(tert-butoxycarbonyl)amino]-2-[(1-n-propyl-1H-imidazol-4-yl)methyl]pentanoate

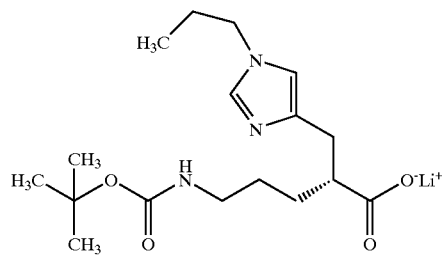

Water (2 ml) and lithium hydroxide monohydrate (81 mg, 1.93 mmol) were added to a solution of the lactam from Preparation 10 (207 mg, 0.64 mmol) in tetrahydrofuran (3.5 ml), and the solution stirred at room temperature for 23 hours. The mixture was concentrated under reduced pressure and the residue purified by column chromatography on silica gel using dichloromethane:methanol:0.88 ammonia (90:10:0 to 90:10:1) to give the title compound, 200 mg, 92% yield.

$^1$H-NMR (CD$_3$OD, 300 MHz) δ: 0.90 (t, 3H), 1.42 (s, 9H), 1.45–1.62 (m, 4H), 1.80 (m, 2H), 2.57–2.70 (m, 2H), 2.85 (m, 1H), 3.02 (m, 2H), 3.95 (t, 2H), 6.97 (s, 1H), 7.76 (s, 1H).

LMRS (ES$^-$): m/z 338 (M–H)$^-$

Preparation 10 and Preparation 11

(−)-tert-Butyl (3R)-2-oxo-3-[(1-n-propyl-1H-imidazol-4-yl)methyl]-1-piperidinecarboxylate (10)

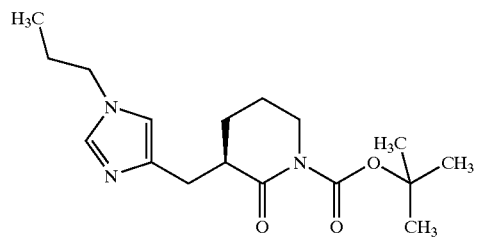

(+)-tert-Butyl (3S)-2-oxo-3-[(1-n-propyl-1H-imidazol-4-yl)methyl]-1-piperidinecarboxylate (11)

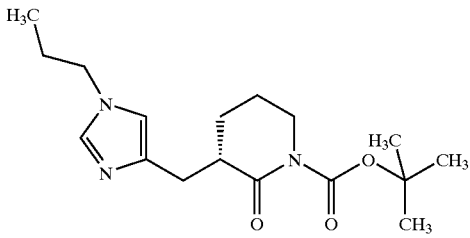

A mixture of the alkene from Preparation 53 (6.6 g, 20.6 mmol) and palladium black (700 mg) in ethanol (120 ml) was hydrogenated at 4 atm and 60° C. for 18 hours. The cooled mixture was filtered through Arbocel™, washing through with ethyl acetate, and the filtrate concentrated under reduced pressure. The crude product was purified by column chromatography on silica gel, eluting with dichloromethane:methanol (97:3), to afford the racemate of the title compounds as a yellow oil, 4.3 g, 65% yield.

This racemic compound was resolved by HPLC using a Chiralcel® OG 250 column (20 mm), and hexane:isopropanol (70:30) as eluant at a rate of 10 ml/minute, to give the title compound of Preparation 10, 1.56 g, 99.5% ee, Retention time: 10.10 minutes, $^1$H-NMR (CDCl$_3$, 300 MHz) δ: 0.92 (t, 3H), 1.54 (s, 9H), 1.63 (m, 2H), 1.80 (m, 3H), 2.00 (m, 1H), 2.65–2.88 (m, 2H), 3.18 (m, 1H), 3.58 (m, 1H), 3.70–3.90 (m, 3H), 6.72 (s, 1H), 7.38 (s, 1H).

LMRS: m/z 322.5 (MH$^+$)

[α]$_D$=−34.34 (c 0.12, dichloromethane)

and the title compound of Preparation 11, 1.56 g, 98.9% ee,

Retention time: 15.23 minutes, $^1$H-NMR (CDCl$_3$, 300 MHz) δ: 0.92 (t, 3H), 1.54 (s, 9H), 1.80 (m, 4H), 2.00 (m, 2H), 2.63–2.85 (m, 2H), 3.19 (m, 1H), 3.58 (m, 1H), 3.90–3.98 (m, 3H), 6.72 (s, 1H), 7.37 (s, 1H).

LMRS: m/z 322.3 (MH$^+$)

[α]$_D$=+27.7 (c 0.22, dichloromethane)

Preparation 12 and Preparation 13

Ethyl (2R)-2-[(1-{[2-(trimethylsilyl)ethoxy]methyl}-1H-imidazol-4-yl)methyl]-5-(tritylamino)pentanoate (12)

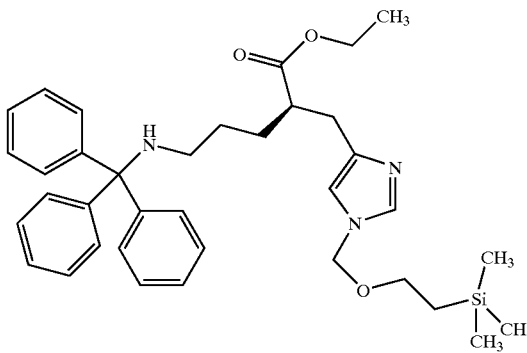

Ethyl (2S)-2-[(1-{[2-(trimethylsilyl)ethoxy]methyl}-1H-imidazol-4-yl)methyl]-5-(tritylamino)pentanoate (13)

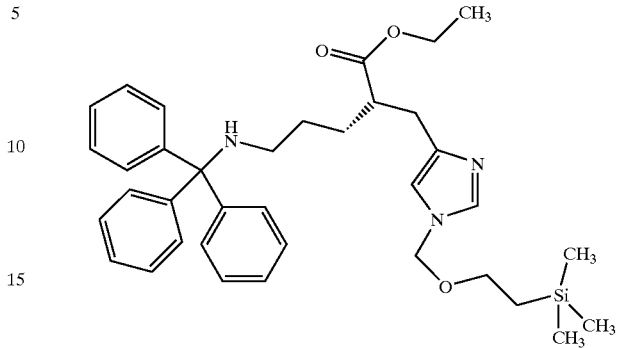

The compound from Preparation 1 was resolved by HPLC using a Chiralcel® OD 250 column (20 mm), and hexane:isopropanol:diethylamine (90:10:0.5) as eluant at 10 ml/minute, to give, the title compound of Preparation 12, in 25% yield, 99.4% ee, Retention time: 16.90 minutes.

$^1$H-NMR (CDCl$_3$, 400 MHz) δ: −0.02 (s, 9H), 0.95 (t, 2H), 1.20 (t, 3H), 1.44–1.66 (m, 4H), 2.09 (m, 2H), 2.64–2.80 (m, 2H), 2.90 (dd, 1H), 3.42 (t, 2H), 4.09 (q, 2H), 5.18 (s, 2H), 6.75 (s, 1H), 7.17 (m, 3H), 7.22 (m, 7H), 7.42 (d, 6H).

LMRS: m/z 598.7 (MH$^+$)

and the title compound of Preparation 13, in 36% yield, 96.5% ee,

Retention time: 22.27 minutes.

$^1$H-NMR (CDCl$_3$, 400 MHz) δ: −0.02 (s, 9H), 0.95 (t, 2H), 1.20 (t, 3H), 1.44–1.66 (m, 4H), 2.09 (m, 2H), 2.64–2.80 (m, 2H), 2.90 (dd, 1H), 3.42 (t, 2H), 4.09 (q, 2H), 5.18 (s, 2H), 6.75 (s, 1H), 7.17 (m, 3H), 7.22 (m, 7H), 7.42 (d, 6H).

Preparation 14

Lithium 5-[(tert-butoxycarbonyl)amino]-2-[(4-propyl-1-{[2-(trimethylsilyl)ethoxy]methyl}-1H-imidazol-2-yl)methyl]pentanoate

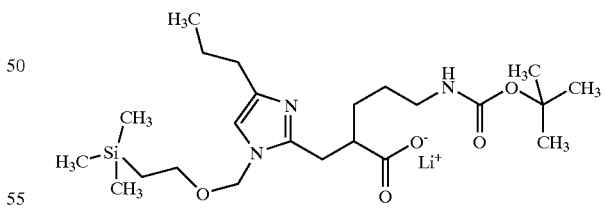

Lithium hydroxide monohydrate (42 mg, 0.99 mmol) was added to a solution of the lactam from Preparation 15 (150 mg, 0.33 mmol) in tetrahydrofuran (1 ml) and water (1.5 ml), and the reaction stirred for 4 hours at room temperature. The mixture was concentrated under reduced pressure and the residue purified by column chromatography on silica gel eluting with dichloromethane:methanol (90:10) as eluant to give the title compound, 108 mg, 70% yield.

$^1$H-NMR (CD$_3$OD, 300 MHz) δ: 0.00 (s, 9H), 0.96 (m, 5H), 1.42 (s, 9H), 1.54 (m, 3H), 1.63 (m, 3H), 2.58 (t, 2H), 2.80 (m, 1H), 2.88–2.98 (m, 1H), 3.02 (m, 2H), 3.16 (dd, 1H), 3.60 (t, 2H), 5.34 (d, 1H), 5.50 (d, 1H), 7.07 (s, 1H).

LMRS: m/z 470.3 (MH⁺)

Preparation 15 tert-Butyl 2-oxo-3-[(4-n-propyl-1-{[2-(trimethylsilyl)ethoxy]methyl}-1H-imidazol-2-yl)methyl]-1-piperidinecarboxylate

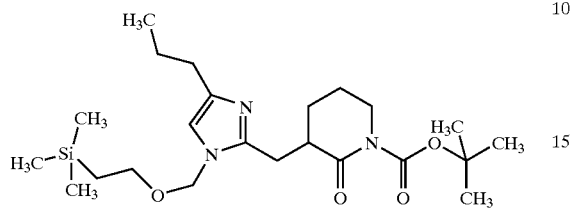

The title compound was obtained in 75% yield from the alkene of Preparation 54, following a similar procedure to that described in Preparation 10/11.

¹H-NMR (CDCl₃, 300 MHz) δ: −0.02 (s, 9H), 0.82–0.98 (m, 5H), 1.50 (s, 9H), 1.60 (m, 3H), 1.81 (m, 2H), 2.05 (m, 1H), 2.46 (t, 2H), 2.74 (dd, 1H), 3.03 (m, 1H), 3.35 (dd, 1H), 3.46 (t, 2H), 3.58 (m, 1H), 3.82 (m, 1H), 5.15 (d, 1H), 5.30 (d, 1H), 6.59 (s, 1H).

LMRS: m/z 452.4 (MH⁺)

Preparation 16

Methyl (2S)-2-({2-[(tert-butoxycarbonyl)amino]ethyl}amino)-3-(1H-imidazol-4-yl)propanoate

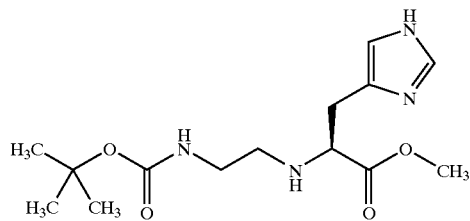

L-Histidine methyl ester (7.93 g, 32.8 mmol) and sodium acetate (10.75 g, 131 mmol) were added to a stirred solution of tert-butyl N-(2-oxoethyl)carbamate (5.22 g, 32.8 mmol) in methanol (100 ml). 4 Å molecular sieves and sodium cyanoborohydride (4.12 g, 65.6 mmol) were added and the mixture was stirred at room temperature for 17 hours. Aqueous hydrochloric acid (2N, 4 ml) was added and the mixture was then basified with saturated aqueous sodium carbonate solution to pH=10. The mixture was filtered to remove solid which was washed with methanol. Methanol was removed by evaporation under reduced pressure and the residual aqueous solution was extracted with ethyl acetate (2×300 ml). The combined organic extracts were then dried (MgSO₄), filtered, and concentrated under reduced pressure. The resultant residue was purified by column chromatography on silica gel, eluting with a solvent gradient of dichloromethane:methanol (96:4 to 92:8), to afford the title compound as a colorless oil, 8.07 g, 79% yield.

¹H-NMR (CDCl₃, 300 MHz) δ: 1.42 (s, 9H), 2.65 (m, 1H), 2.90 (m, 2H), 3.07 (m, 1H), 3.19 (m, 1H), 3.30 (m, 1H), 3.58 (m, 1H), 3.73 (s, 3H), 5.22 (br s, 1H), 6.97 (s, 1H), 7.02 (br s, 2H), 7.91 (s, 1H).

LMRS: m/z 313.1 (MH⁺)

Preparation 17

Methyl (2R)-2-({2-[(tert-butoxycarbonyl)amino]ethyl}amino)-3-(1H-imidazol-4-yl)propanoate

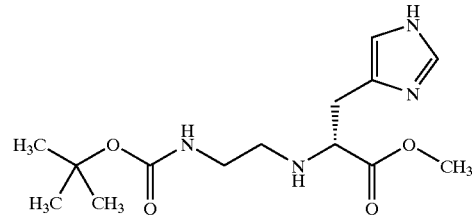

The title compound was prepared from D-histidine methyl ester according to the procedure described in Preparation 16.

¹H-NMR (CDCl₃, 300 MHz) δ: 1.41 (s, 9H), 2.57 (m, 1H), 2.80 (m, 2H), 3.00 (m, 1H), 3.14 (m, 1H), 3.23 (m, 1H), 3.50 (m, 1H), 3.68 (s, 3H), 6.77 (s, 1H), 7.50 (s, 1H).

LMRS: m/z 313 (MH⁺)

Preparation 18

(±)-Methyl 2-({2-[(tert-butoxycarbonyl)amino]ethyl}amino)-3-(1H-imidazol-2-yl)propanoate

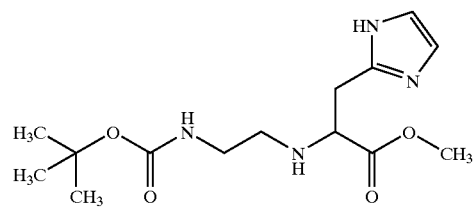

A solution of the amine from Preparation 55 (183 mg, 10.8 mmol) was dissolved in methanol (7 ml) and of tert-butyl N-(2-oxoethyl)carbamate (172 mg, 10.8 mmol) was added. Sodium acetate (354 mg, 43.2 mmol), 4 Å molecular sieves and then sodium cyanoborohydride (135 mg, 21.6 mmol) were added, and the resultant mixture was stirred at room temperature for 18 hours. Aqueous hydrochloric acid (2N, 1 ml) was then added and the reaction mixture was stirred thoroughly and then basified with saturated aqueous sodium carbonate solution to pH=10. The resultant mixture was then filtered to remove solid and the filtrate was extracted with ethyl acetate (2×). The combined organic extracts were dried (MgSO₄), filtered, and then concentrated under reduced pressure. The residue was purified by column chromatography on silica gel eluting with a solvent gradient of methanol:dichloromethane (1:99 to 5:95) to give the title compound, 105 mg, 31% yield.

¹H-NMR (CD₃OD, 400 MHz) δ: 1.42 (s, 9H), 2.58 (m, 1H), 2.74 (m, 1H), 3.11 (m, 4H), 3.67 (m, 1H), 3.70 (s, 3H), 7.10 (s, 2H).

Preparation 19

Methyl (2S)-2-({2-[(tert-butoxycarbonyl)amino]ethyl}amino)-3-(1-{[2-(trimethylsilyl)ethoxy]methyl}-1H-imidazol-2-yl)propanoate

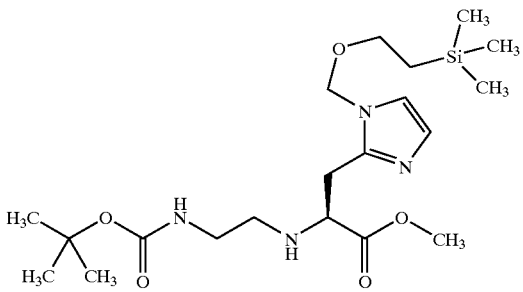

A solution of the amine from Preparation 56 (120 mg, 0.40 mmol) was dissolved in methanol (3.5 ml) and of tert-butyl N-(2-oxoethyl)carbamate (51 mg, 0.33 mmol) was added. Sodium acetate (131 mg, 1.60 mmol), 4 Å molecular sieves and then sodium cyanoborohydride (50 mg, 0.80 mmol) were added, and the resultant mixture was stirred at room temperature for 18 hours. Aqueous hydrochloric acid (1N, 1 ml) was then added and the reaction mixture was stirred thoroughly and then basified with saturated aqueous sodium carbonate solution to pH=10. The resultant mixture was extracted with ethyl acetate (2×) and the combined organic extracts were then dried (MgSO$_4$), filtered, and concentrated under reduced pressure. The residue was purified by column chromatography on silica gel eluting with ethyl acetate:methanol:0.88 ammonia (55:5:0.5) to give the title compound, 30 mg, 21% yield.

$^1$H-NMR (CDCl$_3$, 300 MHz) δ: −0.02 (s, 9H), 0.90 (t, 2H), 1.29 (s, 9H), 2.63 (m, 1H), 2.84 (m, 1H), 3.02 (dd, 1H), 3.13 (dd, 1H), 3.19 (m, 1H), 3.48 (t, 2H), 3.74 (s, 3H), 3.84 (m, 1H), 5.21 (dd, 2H), 5.77 (br s, 1H), 6.90 (s, 1H), 6.97 (s, 1H).

LMRS: m/z 443.3 (MH$^+$)

Preparation 20

Methyl (2S)-3-(1H-imidazol-5-yl)-2-[(3RS)-pyrrolidinylamino]propanoate

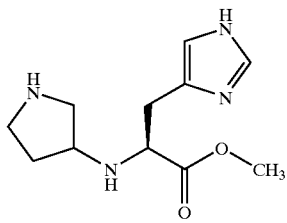

A solution of the product from Preparation 25 (0.4 g, 1.22 mmol) in acetic acid (30 ml) was hydrogenated over palladium catalyst (10% on carbon, 50 mg) at 50° C. and 3.5 atm for 72 hours. The solution was filtered over Arbocel™/Hyflo™ and the filtrate was concentrated under reduced pressure. The resultant oil was dissolved in dichloromethane and extracted with saturated aqueous sodium bicarbonate solution (3×20 ml). The aqueous phase was concentrated under-reduced pressure and the resultant white solid was triturated with hot ethyl acetate (2×50 ml) then with hot methanol (2×50 ml). The methanol extracts were combined and evaporated under reduced pressure. The resultant residue was dissolved in dichloromethane:methanol:0.88 ammonia (80:20:2) and purified by column chromatography on silica gel, eluting with dichloromethane:methanol:0.88 ammonia (80:20:5), to afford the title compound as an orange oil, 200 mg, 70% yield.

$^1$H-NMR (300 MHz, D$_2$O), mixture of diastereoisomers, δ: 1.70 (m, 1H), 2.02 (m, 1H), 2.93 (m, 3H), 3.10–3.47 (m, 4H), 3.58 (2×s, 2×1½H), 3.61 (m, 1H), 6.98 (2×s, 2×½H), 8.00 (2×s, 2×1½H).

HRMS: m/z 239.1514 (MH$^+$), calcd 239.1503.

Preparations 21 and 22

Methyl (2S)-2-[((1R or S)-1-{[(tert-butoxycarbonyl)amino]methyl}propyl)amino]-3-(1H-imidazol-4-yl)propanoate (21)

Methyl (2S)-2-[((1S or R)-1-{[(tert-butoxycarbonyl)amino]methyl}propyl)amino]-3-(1H-imidazol-4-yl)propanoate (22)

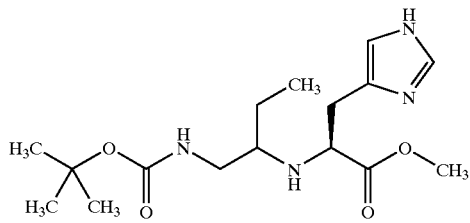

L-Histidine methyl ester dihydrochloride (945 mg, 3.9 mmol) and sodium acetate (1.28 g, 15.6 mmol) were added to a stirred solution of the product from Preparation 77 (730 mg, 3.9 mmol) in methanol (50 ml). 4 Å molecular sieves and sodium cyanoborohydride (491 mg, 7.8 mmol) were added and the mixture was stirred at room temperature for 17 hours. The mixture was filtered and the filtrate was concentrated to 10 ml under reduced pressure. Aqueous hydrochloric acid (2N, 2 ml) was added and the mixture was stirred for two minutes. Saturated aqueous sodium hydrogen carbonate solution was added and the mixture was extracted with ethyl acetate (3×150 ml). The combined organic extracts were dried (Na$_2$SO$_4$), filtered, and concentrated under reduced pressure. The residue was purified by column chromatography on silica gel (Biotage™ column), eluting with a solvent gradient of dichloromethane:methanol (95:5 to 90:10), to afford the following title compounds (21 and 22).

Preparation 21, 178 mg, 13% yield:
$^1$H-NMR (CDCl$_3$, 400 MHz) δ: 0.90 (t, 3H), 1.40 (m, 2H), 1.43 (s, 9H), 2.30 (br m, 1H), 2.82 (dd, 1H), 2.97 (dd, 1H), 3.02 (m, 1H), 3.20 (br m, 1H), 3.65 (m, 1H), 3.72 (s, 3H), 5.21 (br s, 1H), 6.80 (s, 1H), 7.57 (s, 1H).

LMRS: m/z 341.2 (MH$^+$)

TLC: dichloromethane:methanol (90:10) Rf=0.48.

Preparation 22, 271 mg, 20% yield:
$^1$H-NMR (CDCl$_3$, 400 MHz) δ: 0.82 (t, 3H), 1.23–1.42 (m, 2H), 1.45 (s, 9H), 2.50 (br m, 1H), 2.80 (dd, 1H), 3.00 (dd, 1H), 3.03–3.18 (m, 2H), 3.60 (m, 1H), 3.73 (s, 3H), 5.30 (br s 1H), 6.82 (s, 1H), 7.53 (s, 1H)

LMRS: m/z 341.3 (MH$^+$)

TLC: dichloromethane:methanol (90:10) Rf=0.41.

Preparations 23–26

The compounds of the following tabulated Preparations of the general formula:

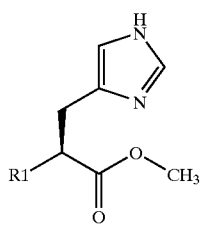

were prepared by a similar method to that of Preparation using L-histidine methyl ester dihydrochloride and the appropriate aldehyde/ketone starting materials (products from Preparations 78–80 or commercially-available 1-benzyl-3-pyrrolidinone).

Preparation 27

Methyl (2S)-2-[{2-[(tert-butoxycarbonyl)amino]ethyl}(methyl)amino]-3-(1H-imidazol-4-yl)propanoate

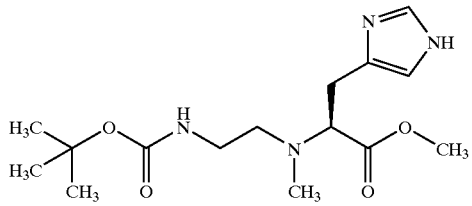

| Prep. No. | R$^1$ | Yield (%) | Analytical Data |
|---|---|---|---|
| 3 | | 48 | $^1$H-NMR(CDCl$_3$, 300 MHz), mixture of diastereoisomers, δ: 0.78–0.98(4 × d, 6H), 1.43(2 × s, 9H), 1.69(m, 1H), 2.37(m, 1H), 2.78–3.28(m, 4H), 3.66(m, 1H), 3.73(2 × s, 3H), 5.20(br s, 1H), 6.82(2 × s, 1H), 7.58(2 × s, 1 H). TLC:ethyl acetate:methanol (90:10)Rf = 0.27. |
| 24 | | 45 | $^1$H-NMR(CDCl$_3$, 300 MHz), mixture of diastereoisomers, δ: 1.45(2 × s, 9H), 2.50–3.30 (m, 7H), 3.45–3.70 (2 × m, 1H), 3.63–3.73 (2 × s, 3H), 5.07(br m, 1H)6.65–6.78(2 × s, 1H), 7.10–7.58 (m + 2 × s, 6H). LRMS: m/z 402.6(MH$^+$) |
| 25 | | 37 | $^1$H-NMR (CDCl$_3$, 300 MHz), mixture of diastereoisomers, δ: 1.53(m, 1H), 2.00(m, ½ H) 2.13 (m, ½ H), 2.30–2.60(m, 2H), 2.63–2.81(m, 2H), 2.90(m, 1H), 2.99 (m, 1H), 3.30(m, 1H), 3.45(m, 1H), 3.59(m, 2H), 3.67(s, 1½ H), 3.73(s, 1½ H) 6.80(s, 1H), 7.28 (m, 5H), 7.41(s, ½ H), 7.47 (s, ½ H). LRMS: m/z 329.4 (MH$^+$) Anal. Found: C, 65.69; H, 7.41; N, 16.95. C$_{18}$H$_{24}$N$_4$O$_2$ requires C, 65.83; H, 7.37; N, 17.06%. |
| 26 | | 67 | $^1$H-NMR(CDCl$_3$, 300 MHz), mixture of diastereoisomers, δ: 0.87–1.13(m, 6H), 1.45(2 × s, 9H), 2.68(m, 1H), 2.87(m, 1H), 3.02(m, 1H), 3.62(br m, 1H), 3.70 (s, 3H), 4.45(br s, 2H), 4.88(br m, 1H), 6.85(br s, 1H), 7.60 (br s, 1H). HRMS: m/z 341.2180 (MH$^+$), calcd 341.2184. |

A solution of methyl (2S)-3-(4-imidazolidinyl)-2-(methylamino)propanoate (1 g, 4.55 mmol), of tert-butyl N-(2-oxoethyl)carbamate (833 mg, 5.23 mmol), sodium acetate (1.494 g, 18.22 mmol) and sodium cyanoborohydride (572 mg, 9.10 mmol) in methanol (30 ml) was stirred at 0° C. under a nitrogen atmosphere. The mixture was allowed to warm to room temperature then aqueous hydrochloric acid (5 ml, 1N) was added, followed by saturated aqueous sodium hydrogen carbonate solution. The solution was filtered and the aqueous phase was extracted with ethyl acetate. The combined organic extracts were washed with brine, dried (MgSO$_4$), filtered, and then concentrated under reduced pressure. The residue was purified by column chromatography on silica gel, eluting with dichloromethane:methanol (100:5), to afford the title compound, 900 mg, 61% yield.

$^1$H-NMR (CDCl$_3$, 300 MHz) δ: 1.43 (s, 9H), 2.32 (s, 3H), 2.60 (m, 1H), 2.78 (m, 1H), 2.90 (m, 1H), 3.02 (m, 1H), 3.19 (m, 2H), 3.60 (m, 1H), 3.70 (s, 3H), 5.30 (br m, 1H), 6.80 (s, 1H), 7.55 (s, 1H).

LMRS: m/z 327.1 (MH$^+$)

Preparation 28

Methyl (2S)-3-(1H-imidazol-4-yl)-2-(1-piperazinyl)propanoate

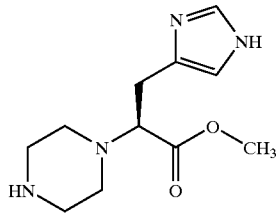

The product from Preparation 29 (200 mg, 0.315 mmol) was added to a suspension of 4-hydroxybenzoic acid (0.22 g, 1.5 mmol) in hydrogen bromide solution (45% in acetic acid, 5 ml) at 0° C. and the mixture was stirred at room temperature for 72 hours. Deionized water (20 ml) was added to afford a suspension which was extracted with ethyl acetate (3×20 ml). The residual aqueous solution was then concentrated under reduced pressure. The resultant orange foam was crystallized from methanol:ethyl acetate to afford the tri-hydrobromide salt of the title compound as a colorless solid, 82 mg, 54% yield. M.p. 211–213° C.

$^1$H-NMR (D$_2$O, 300 MHz) δ: 2.80 (m, 2H), 2.97 (m, 2H), 3.15 (m, 6H), 3.65 (s, 3H), 3.73 (t, 1H), 7.23 (s, 1H), 8.53 (s, 1H).

LMRS: m/z 239.2 (MH$^+$)

Anal. Found: C, 27.37; H, 4.45; N, 11.36. C$_{11}$H$_{18}$N$_4$O$_2$.3HBr requires C, 27.47; H, 4.40; N, 11.65%.

$[α]_D$=−32.92 (c 0.11, methanol)

Preparation 29

Methyl (2S)-2-{4-[(4-methylphenyl)sulfonyl]-1-piperazinyl}-3-(1-trityl-1H-imidazol-4-yl)propanoate

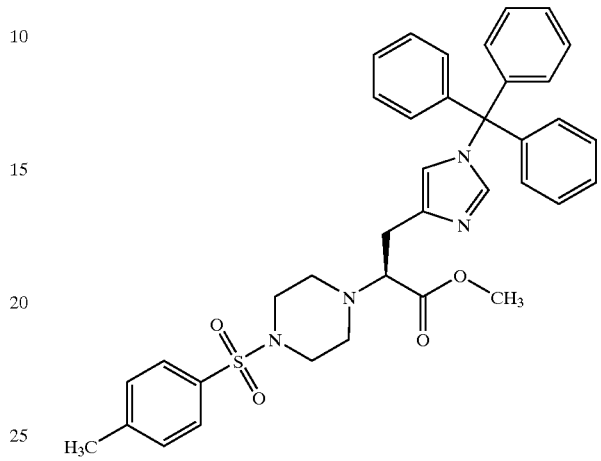

A suspension of methyl (2S)-2-amino-3-(1-trityl-1H-imidazol-4-yl)propanoate (1 g, 2.4 mmol) in diisopropylethylamine (5 ml), was stirred at room temperature for 20 minutes. N,N-Bis(2-chloroethyl)-4-methylbenzenesulfonamide (720 mg, 2.4 mmol) was added and the mixture was stirred at reflux for 3 hours. The mixture was allowed to cool and diluted with acetonitrile. The resultant solution was concentrated under reduced pressure and the residue was suspended in aqueous sodium carbonate solution and extracted with dichloromethane (3×20 ml). The combined organic extracts were washed with brine (3×20 ml), dried (Na$_2$SO$_4$), filtered, and then concentrated under reduced pressure. The residue was purified by column chromatography on silica gel, eluting with a solvent gradient of dichloromethane:methanol (99:1). The isolated material was dissolved in ether and the resultant solution concentrated under reduced pressure to afford the title compound as a colorless foam, 300 mg, 19% yield.

$^1$H-NMR (CDCl$_3$, 300 MHz) δ: 2.42 (s, 3H), 2.63 (m, 2H), 2.72 (m, 2H), 2.78 (dd, 1H), 2.97 (m, 5H), 3.57 (s, 3H), 3.60 (m, 1H), 6.50 (s, 1H), 7.07 (m, 6H), 7.50 (m, 12H). 7.62 (2×s, 2H).

LMRS: m/z 635.3 (MH$^+$)

Anal. Found: C, 69.51; H, 6.06; N, 8.69. C$_{37}$H$_{38}$N$_4$O$_4$S.0.25H$_2$O requires C, 69.51; H, 6.07; N, 8.59%.

$[α]_D$=−3.73 (c 0.10, dichloromethane)

Preparation 30

(7S)-6-{2-[(tert-Butoxycarbonyl)amino]ethyl}-2-ethyl-7-(methoxycarbonyl)-5-oxo-5,6,7,8-tetrahydroimidazo[1,5-c]pyrimidin-2-ium iodide

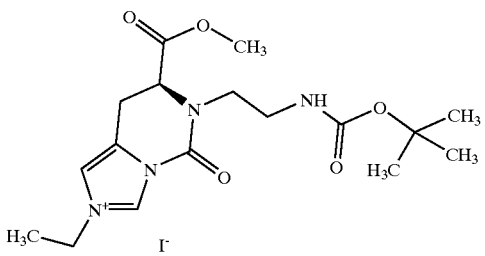

Ethyl iodide (99 μl, 1.243 mmol) was added to a stirred solution of the product from Preparation 48 (200 mg, 0.592 mmol) in acetonitrile (5 ml) and the mixture was heated at reflux for 17 hours under a nitrogen atmosphere. The mixture was allowed to cool to room temperature and the solvent was removed by evaporation under reduced pressure. The residue was purified by column chromatography on silica gel eluting with dichloromethane:methanol (90:10) to afford the title compound as a white foam, 118 mg, 40% yield.

$^1$H-NMR (D$_2$O, 300 MHz) δ: 1.27 (s, 9H), 1.42 (t, 3H), 3.22–3.47 (m, 4H), 3.58 (m, 1H), 3.65 (s, 3H), 3.95 (m, 1H), 4.20 (q, 2H), 4.75 (m, 1H), 7.40 (s, 1H).

LMRS: 366.9 (M$^+$)

TLC: dichloromethane:methanol:0.88 ammonia (90:10:1) Rf=0.26.

Preparations 31–46

The compounds of the following tabulated Preparations of general formula:

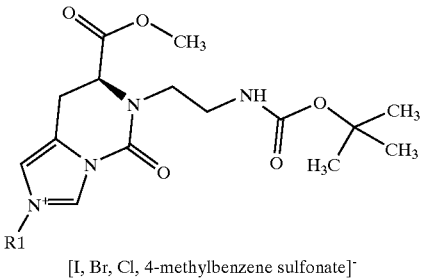

[I, Br, Cl, 4-methylbenzene sulfonate]$^-$ were prepared by a similar method to that of Preparation 30 using the product of Preparation 48 and the appropriate alkylating agent.

| Prep. No. | Alkylating agent | R$^1$ | Yield (%) | Analytical Data |
|---|---|---|---|---|
| 31 | n-Propyl bromide (3eq) | H$_3$C∼∼∼ | 44 | $^1$H-NMR(D$_2$O, 400 MHz) δ: 0.75(t, 3H), 1.20(s, 9H), 1.75 (q, 2H), 3.20–3.40(m, 4H), 3.50 (m, 1H), 3.60(s, 3H), 3.90(m, 1H), 4.07(t, 2H), 4.65(m, 1H), 7.30(s, 1H). |
| 32 | n-Butyl bromide (3eq) | H$_3$C∼∼∼∼ | 46 | $^1$H-NMR(D$_2$O, 300 MHz) δ: 0.82(t, 3H), 1.22(q, 2H), 1.30 (s, 9H), 1.80(m, 2H), 3.27–3.47(m, 4H), 3.58(m, 1H), 3.67(s, 3H), 3.97(m, 1H), 4.17(t, 2H), 4.77(m, 1H), 7.40(s, 1H). LRMS: m/z 395.3 (M$^+$) |
| 33 | n-Pentyl bromide (5eq) | H$_3$C∼∼∼∼∼ | 55 | $^1$H-NMR(D$_2$O, 300 MHz) δ: 0.72(t, 3H), 1.03–1.13(m, 4H), 1.22(s, 9H), 1.75(m, 2H), 3.17–3.40 (m, 4H), 3.50 (m, 1H), 3.60(s, 3H), 3.90 (m, 1H), 4.12(t, 2H), 4.68(m, 1H), 7.33(s, 1H). LRMS: 409.4 (M$^+$) |
| 34 | 2-Bromo-propane (5eq) | (CH$_3$)$_2$CH– | 9 | $^1$H-NMR(D$_2$O, 300 MHz) δ: 1.28(s, 9H), 1.47(d, 6H), 3.20–3.40(m, 5H), 3.57(m, 1H), 3.67(s, 3H), 3.95(m, 1H), 4.75(m, 1H), 7.45(s, 1H). LRMS: m/z 381.2(M$^+$) |
| 35 | 1-Iodo-2-methyl-propane (5eq) | (CH$_3$)$_2$CHCH$_2$– | 32 | $^1$H-NMR(D$_2$O, 400 MHz) δ: 0.82(d, 6H), 1.27(s, 9H), 2.07(m, 1H), 3.25–3.45(m, 4H), 3.57(m, 1H), 3.64(s, 3H), 3.93(m, 1H), 4.00(d, 2H), 4.75(m, 1H), 7.37(s, 1H). LRMS: m/z 394.9(M$^+$) |

-continued

| Prep. No. | Alkylating agent | R¹ | Yield (%) | Analytical Data |
|---|---|---|---|---|
| 36 | 1-Bromo-3-methyl-butane (5eq) | (isopentyl group: H₃C-CH(CH₃)-CH₂-CH₂-) | 51 | ¹H-NMR(D₂O, 300 MHz) δ: 0.83(d, 6H), 1.28(s, 9H), 1.45(m, 1H), 1.70(m, 2H), 3.25–3.47(m, 4H), 3.57(m, 1H), 3.65(s, 3H), 3.95(m, 1H), 4.20(t, 2H), 4.73(m, 1H), 7.39(s, 1H). LRMS: m/z 409.0(M⁺) |
| 37 | (1R)-1-methyl-propyl 4-methyl-benzene sufonate (1.1eq)¹ | (R)-sec-butyl | 19 | ¹H-NMR(D₂O, 300 MHz) δ: 0.77(t, 3H), 1.28(s, 9H), 1.45(d, 3H), 1.79(m, 2H), 2.30(s, 3H), 3.22–3.42(m, 4H), 3.50–3.62(m, 1H), 3.67(s, 3H), 3.97(m, 1H), 4.40(m, 1H), 4.76(m, 1H), 7.28(d, 2H), 7.45(s, 1H), 7.60(d, 2H). LRMS: m/z 395.9(M⁺) |
| 38 | (1S)-1-methyl-propyl 4-methyl benzene sulfonate (1.1eq)² | (S)-sec-butyl | 20 | ¹H-NMR(D₂O, 300 MHz) δ: 0.77(t, 3H), 1.28(s, 9H), 1.45(d, 3H), 1.79(m, 2H), 2.30(s, 3H), 3.22–3.42(m, 4H), 3.50–3.62(m, 1H), 3.67(s, 3H), 3.97(m, 1H), 4.40(m, 1H), 4.76(m, 1H), 7.28(d, 2H), 7.45(s, 1H), 7.60(d, 2H). LRMS: m/z 395.1(M⁺) |
| 39 | (Brom-methyl)cyclo-propane (5eq) | cyclopropylmethyl | 57 | ¹H-NMR(D₂O, 300 MHz) δ: 0.40(m, 2H), 0.67(m, 2H), 1.25(s + m, 10H), 3.18–3.50(m, 4H), 3.58(m, 1H), 3.67(s, 3H), 3.95(m, 1H), 4.02(d, 2H), 4.77(m, 1H), 7.43(s, 1H). LRMS: m/z 393.0 (M⁺) |
| 40 | (Bromo-methyl)cyclo-butane (5eq) | cyclobutylmethyl | 35 | ¹H-NMR(D₂O, 300 MHz) δ: 1.27(s, 9H), 1.62–2.07(m, 6H), 2.73(m, 1H), 3.20–3.45(m, 4H), 3.53(m, 1H), 3.65(s, 3H), 3.95(m, 1H), 4.17(d, 2H), 4.72(m, 1H), 7.33(s, 1H). LRMS: m/z 407.9(M⁺) |
| 41 | 1-Bromo-2-methoxy-ethane (3eq) | H₃C-O-CH₂-CH₂- | 73 | ¹H-NMR(D₂O, 400 MHz) δ: 1.27(s, 9H), 3.20–3.50(m, 8H), 3.57(m, 1H), 3.67(m, 2H), 3.77(m, 2H), 3.95(m, 1H), 4.37(m, 2H), 4.75(m, 1H), 7.40(s, 1H). |
| 42 | 1-Bromo propan-3-ol (3eq) | HO-CH₂-CH₂-CH₂- | 73 | ¹H-NMR(D₂O, 300 MHz) δ: 1.30(s, 9H), 2.05(m, 2H), 3.25–3.48(m, 4H), 3.58(m, 3H), 3.67(s, 3H), 3.97(m, 1H), 4.30(t, 2H), 4.78(m, 1H), 7.41(s, 1H). LRMS: m/z 397.3(M⁺) |
| 43 | (±)-3-Methoxy-1-methylethyl 4-methyl-benzene sulfonate (2eq)³ | HO-O-CH(CH₃)-CH₂- | 30 | ¹H-NMR(D₂O, 400 MHz) δ: 1.27(s, 9H), 1.43(d, 3H), 2.27(s, 3H), 3.20–3.45(m, 7H), 3.57–3.72(s + m, 5H), 3.95(br m, 1H), 4.60–4.80(m, 3H), 7.28(d, 2H), 7.47(s, 1H), 7.59(d, 2H). |
| 44 | (2-Bromo-ethyl)benzene | phenethyl | 33 | ¹H-NMR(D₂O, 300 MHz) δ: 1.27(s, 9H), 3.06–3.40(m, 6H), 3.52(m, 1H), 3.71(s, 3H), 3.90(m, 1H), 4.47(m, 2H), 4.84(m, 1H), 7.03(m, 2H), 7.26(m, 4H). LRMS: m/z 443.3(M⁺) |

-continued

| Prep. No. | Alkylating agent | R¹ | Yield (%) | Analytical Data |
|---|---|---|---|---|
| 45 | Allyl bromide (5eq) | 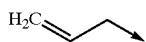 | 76 | ¹H-NMR(D₂O), 300 MHz) δ: 1.22(s, 9H), 3.20–3.38(m, 4H), 3.44–3.57(m, 1H), 3.60 (s, 3H), 3.88(m, 1H), 4.70(m, 3H), 5.29(d, 1H), 5.35(d, 1H), 5.81–5.98(m, 1H), 7.30 (s, 1H). LRMS: m/z 379.2(M⁺) |
| 46 | N-(2-bromo-ethyl) Methane sulfonamide (1.5eq)⁴ | 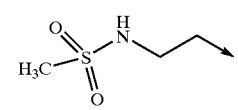 | 29 | ¹H-NMR(D₂O), 300 MHz) δ: 1.30(s, 9H), 2.95(s, 3H), 3.24–3.56(m, 7H), 3.64(s, 3H), 3.98(m, 1H), 4.32(t, 2H), 4.77(m, 1H), 7.42(s, 1H). LRMS: m/z 460.7(M⁺) |

Footnotes:
¹See, J. Org. Chem., 1983, 48, 4527.
²See, J. Org. Chem., 1974, 39, 1515.
³Product of Preparation 81.
⁴See, JACS, 1951, 73, 3100

Preparation 47

(7S)-6-{2-[(tert-butoxycarbonyl)amino]ethyl}-7-(methoxycarbonyl)-2-[2-(methylamino)-2-oxoethyl]-5-oxo-5,6,7,8-tetrahydroimidazo[1,5-c]pyrimidin-2-ium bromide

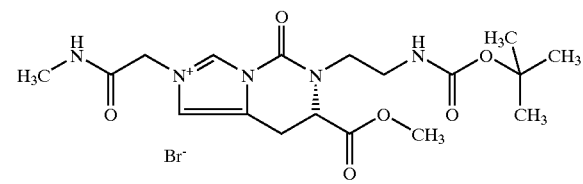

A mixture of the product from Preparation 48 (300 mg, 0.89 mmol) and 2-bromo-N-methylacetamide (Heterocycles 1995, 41, 2427) (270 mg, 1.78 mmol) in acetonitrile (7 ml) was heated at 80° C. for 72 hours. The cooled reaction was concentrated under reduced pressure and the residue purified by column chromatography on silica gel using an elution gradient of dichloromethane: methanol (95:5 to 90:10). The product was triturated with ether to afford the title compound as a white solid, 380 mg, 87% yield.

¹H-NMR (D₂O, 300 MHz) δ: 1.30 (s, 9H), 2.71 (s, 3H), 3.23–3.47 (m, 5H), 3.60 (m, 1H), 3.68 (s, 3H), 3.97 (m, 1H), 4.77 (m, 1H), 5.00 (br s, 2H), 7.38 (s, 1H).

LMRS: m/z 410.4 (M⁺)

Preparation 48

Methyl (7S)-6-{2-[(tert-butoxycarbonyl)amino]ethyl}-5-oxo-5,6,7,8-tetrahydroimidazo[1,5-c]pyrimidine-7-carboxylate

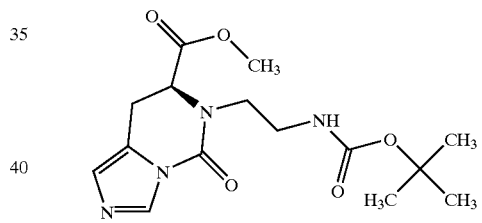

Carbonyldiimidazole (156 mg, 0.959 mmol) was added to a stirred solution of the product from Preparation 16 (300 mg, 0.959 mmol) in N,N-dimethylformamide (5 ml) and the mixture was heated at 60–70° C. for 17 hours. The solvent was removed by evaporation under reduced pressure, the residue was dissolved in saturated aqueous sodium hydrogen carbonate solution and extracted with dichloromethane. The combined organic extracts were dried (MgSO₄), filtered and then concentrated under reduced pressure. The residue was purified by column chromatography on silica gel, eluting with dichloromethane:methanol (95:5), to afford the title compound as a colorless oil, 210 mg, 67% yield.

¹H-NMR (D₂O, 300 MHz) δ: 1.40 (s, 9H), 3.20–3.60 (m, 5H), 3.70 (s, 3H), 4.08 (m, 1H), 4.33 (m, 1H), 4.82 (br m, 1H), 6.80 (s, 1H), 8.13 (s, 1H).

LMRS: m/z 339 (MH⁺)

$[\alpha]_D$=+39.2 (c 0.12, dichloromethane)

TLC: ethyl acetate:methanol (95:5) Rf=0.79

Preparation 49

Ethyl (2E and 2Z)-3-(1-{[2-(trimethylsilyl)ethoxy]methyl}-1H-imidazol-4-yl)-2-[3-(tritylamino)propyl]-2-propenoate

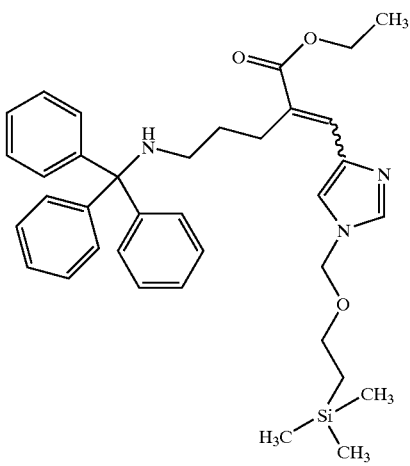

The geometric isomers of the title compound were obtained in 32% and 38% yield respectively, from the compound from Preparation 60, and the aldehyde from Preparation 68, following a similar procedure to that described in Preparation 52.

Isomer 1, $^1$H-NMR (CDCl$_3$, 300 MHz) δ: −0.02 (s, 9H), 0.90 (t, 2H), 1.28 (t, 3H), 1.78 (m, 2H), 2.18 (t, 2H), 2.40 (br s, 1H), 2.97 (t, 2H), 3.44 (t, 2H), 4.19 (q, 2H), 5.20 (s, 2H), 7.15–7.32 (m, 12H), 7.43 (d, 6H).

LMRS: m/z 596.5 (MH$^+$)

and isomer 2, $^1$H-NMR (CDCl$_3$, 300 MHz) δ: −0.01 (s, 9H), 0.90 (t, 2H), 1.28 (t, 3H), 1.72 (m, 2H), 2.19 (t, 2H), 2.46 (t, 2H), 3.47 (t, 2H), 4.22 (q, 2H), 5.22 (s, 2H), 6.70 (s, 1H), 7.18 (m, 3H), 7.24 (m, 6H), 7.45 (d, 6H), 7.55 (s, 1H), 7.79 (s, 1H).

LMRS: m/z 596.3 (MH$^+$)

Preparation 50

Ethyl (2E and 2Z)-3-(1-n-propyl-1H-imidazol-4-yl)-2-[3-(tritylamino)propyl]-2-propenoate

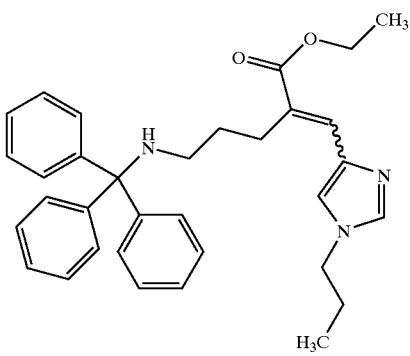

A solution of the compound from Preparation 60 (5.9 g, 11.3 mmol) in tetrahydrofuran (100 ml) was added to an ice-cooled solution of sodium hydride (457 mg, 60% dispersion in mineral oil, 11.3 mmol) in tetrahydrofuran (100 ml), and the mixture stirred for 45 minutes. A solution of the aldehyde from Preparation 66 (1.56 g, 11.3 mmol) in tetrahydrofuran (100 ml) was then added. The reaction was then allowed to warm to room temperature and stirred for 18 hours. The mixture was diluted with aqueous ammonium chloride solution, the layers separated, and the aqueous phase extracted with ethyl acetate (3×). The combined organic extracts were dried (MgSO$_4$), filtered and concentrated under reduced pressure. The residue was purified by column chromatography on silica gel, eluting with a solvent gradient of ethyl acetate:pentane (40:60 to 60:40), to give the two geometric isomers of the title compound, 1.87 g, 33% yield (isomer 1):

$^1$H-NMR (CDCl$_3$, 300 MHz) δ: 0.92 (t, 3H), 1.27 (t, 3H), 1.78 (m, 4H), 2.18 (t, 2H), 2.52 (br s, 1H), 2.96 (t, 2H), 3.82 (t, 2H), 4.18 (q, 2H), 7.10–7.28 (m, 12H), 7.42 (d, 6H).

LMRS: m/z 508.2 (MH$^+$)

and 2.40 g, 42% yield (isomer 2):

$^1$H-NMR (CDCl$_3$, 300 MHz) δ: 0.95 (t, 3H), 1.27 (t, 3H), 1.72 (m, 2H), 1.82 (m, 2H), 2.18 (t, 2H), 2.45 (t, 2H), 3.86 (t, 2H), 4.22 (q, 2H), 6.75 (s, 1H), 7.18 (m, 3H), 7.28 (m, 7H), 7.44 (d, 6H), 7.76 (s, 1H).

LMRS: m/z 508.4 (MH$^+$)

Preparation 51

Ethyl (2E and 2Z)-2-{4-[benzyl(tert-butoxycarbonyl)amino]butyl}-3-(1-n-propyl-1H-imidazol-4-yl)-2-propenoate

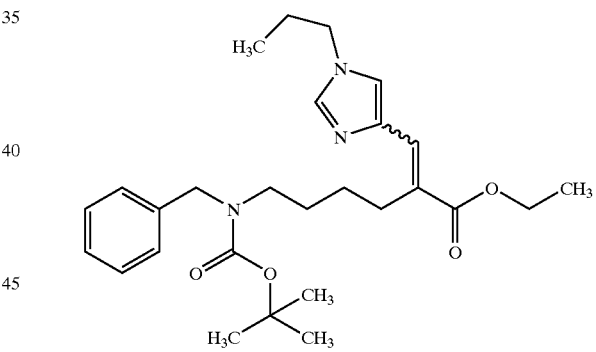

The geometric isomers of the title compound were obtained in 24% and 21% yield respectively, from the compound of Preparation 59, and the aldehyde from Preparation 66, following the procedure described in Preparation 52.

Isomer 1, $^1$H-NMR (CDCl$_3$, 300 MHz) δ: 0.96 (t, 3H), 1.27 (t, 3H), 1.37–1.58 (m, 13H), 1.80 (m, 2H), 2.80 (m, 2H), 3.20 (m, 2H), 3.88 (t, 2H), 4.20 (q, 2H), 4.40 (s, 2H), 7.04 (s, 1H), 7.22 (m, 5H), 7.42 (s, 1H), 7.52 (s, 1H).

LMRS: m/z 470.3 (MH$^+$)

Isomer 2, $^1$H-NMR (CDCl$_3$, 300 MHz) δ: 0.94 (t, 3H), 1.28 (t, 3H), 1.38–1.58 (m, 13H), 1.80 (m, 2H), 2.38 (m, 2H), 3.18 (m, 2H), 3.85 (t, 2H), 4.22 (q, 2H), 4.40 (br s, 2H), 6.70 (s, 1H), 7.23 (m, 5H), 7.40 (s, 1H), 7.75 (s, 1H).

LMRS: m/z 470.3 (MH$^+$)

Preparation 52

Ethyl (2E and 2Z)-3-(1-n-butyl-1H-imidazol-4-yl)-2-[3-(tritylamino)propyl]-2-propenoate

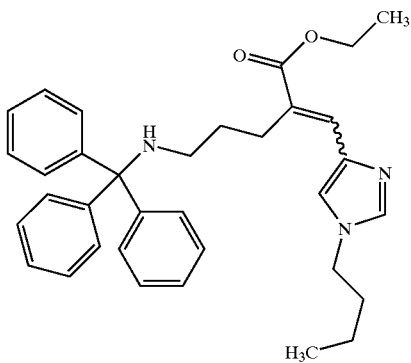

A solution of the compound from Preparation 60 (1 g, 2.6 mmol) in tetrahydrofuran (20 ml) was added to an ice-cooled solution of sodium hydride (106 mg, 60% dispersion in mineral oil, 2.6 mmol) in tetrahydrofuran (20 ml), and the solution stirred for 45 minutes. The aldehyde from Preparation 67 (400 mg, 2.6 mmol) in tetrahydrofuran (10 ml) was then added, and the reaction stirred at room temperature for 18 hours. The reaction was quenched by the addition of aqueous ammonium chloride solution and the mixture extracted with ethyl acetate (2×). The combined organic extracts were dried ($Na_2SO_4$), filtered, and concentrated under reduced pressure. The residue was dissolved in toluene, adsorbed onto silica, and purified by column chromatography on silica gel, eluting with a solvent gradient of ethyl acetate:pentane (20:80 to 40:60), to give the two geometric isomers of the title compound, 390 mg, 29% yield (isomer 1):

$^1$H-NMR (CDCl$_3$, 300 MHz) δ: 0.94 (t, 3H), 1.28 (m, 5H), 1.76 (m, 4H), 2.18 (t, 2H), 2.55 (br s, 1H), 2.97 (t, 2H), 3.84 (t, 2H), 4.17 (q, 2H), 7.09–7.30 (m, 12H), 7.42 (d, 6H).

LMRS: m/z 522 (MH$^+$)

and 400 mg, 30% yield (isomer 2):

$^1$H-NMR (CDCl$_3$, 300 MHz) δ: 0.94 (t, 3H), 1.30 (m, 5H), 1.76 (m, 4H), 2.19 (t, 2H), 2.45 (t, 2H), 3.92 (t, 2H), 4.22 (q, 2H), 6.76 (s, 1H), 7.18 (m, 3H), 7.24 (m, 7H), 7.46 (d, 6H), 7.75 (s, 1H).

LMRS: m/z 523.1 (M+2H)$^+$

Preparation 53 tert-Butyl (3E)-2-oxo-3-[(1-n-propyl-1H-imidazol-4-yl)methylene]-1-piperidinecarboxylate

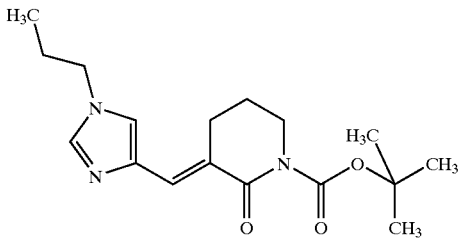

A solution of lithium bis(trimethylsilyl)amide in tetrahydrofuran (43.5 ml, 1M, 43.5 mmol) was added dropwise to a cooled (−78° C.) solution of tert-butyl 2-oxo-1-piperidinecarboxylate (*J. Org. Chem.*, 1983, 48, 2424) (8.7 g, 43.5 mmol) in tetrahydrofuran (120 ml) and, once addition was complete, the solution was allowed to warm to 0° C., and stirred for an hour. The solution was re-cooled to −78° C., a solution of the aldehyde from Preparation 66 (4 g, 28.9 mmol) in tetrahydrofuran (40 ml) was added, and the reaction was then allowed to warm to room temperature. The reaction mixture was stirred for 18 hours and then partitioned between water and ethyl acetate. The phases were separated and the organic phase was dried (MgSO$_4$), filtered, and concentrated under reduced pressure. The residue was purified by column chromatography on silica gel, eluting with dichloromethane:methanol (95:5), to give the title compound as a single geometric isomer, 4 g, 43% yield.

$^1$H-NMR (CDCl$_3$, 300 MHz) δ: 0.89 (t, 3H), 1.50 (s, 9H), 1.78 (m, 2H), 1.86 (m, 2H), 3.00 (m, 2H), 3.70 (t, 2H), 3.85 (t, 2H), 7.07 (s, 1H), 7.46 (s, 1H), 7.62 (s, 1H).

LMRS: m/z 320.3 (MH$^+$)

Alternative Method of Synthesis for Title Compound in Preparation 53

The compound from Preparation 99 (76.5 g, 227 mmol) was dissolved in dichloromethane (300 ml), the solution was cooled to 0° C., and triethylamine (57 g, 560 mmol) was added. Methanesulphonyl chloride (23.7 g, 207 mmol) in dichloromethane (15 ml) was then added slowly to the stirred solution over 0.5 hours whilst maintaining the reaction temperature between 0–5° C. The reaction was then allowed to warm to room temperature and was stirred for 3 hours. The reaction mixture was then quenched into water (315 ml) and the organic phase separated. The aqueous phase was then extracted with dichloromethane (1×50 ml) and the combined organic extracts were washed with water (1×100 ml), dried and concentrated under reduced pressure to afford the title compound as a solid, 58.0 g, 88% yield.

Preparation 54 tert-Butyl (3E or 3Z)-2-oxo-3-[(4-n-propyl-1-{[2-(trimethylsilyl)ethoxy]methyl}-1H-imidazol-2-yl)methylene]-1-piperidinecarboxylate or tert-Butyl (3E or 3Z)-2-oxo-3-[(5-n-propyl-1-{[2-(trimethylsilyl)ethoxy]methyl}-1H-imidazol-2-yl)methylene]-1-piperidinecarboxylate

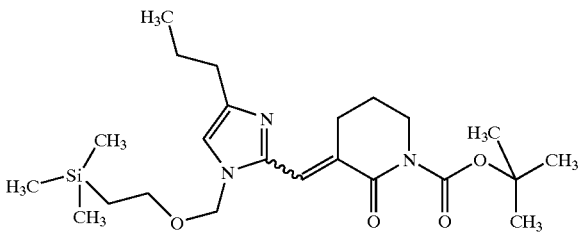

The title compound was obtained as a single stereoisomer in 10% yield from the aldehydes from Preparation 69 and 70, and tert-butyl 2-oxo-1-piperidinecarboxylate (J. Org. Chem. 1983, 48, 2424), following a similar procedure to that described in Preparation 53, except hexane:ether (50:50) was used as the column eluant.

$^1$H-NMR (CDCl$_3$, 300 MHz) δ: −0.03 (s, 9H), 0.88 (t, 2H), 0.98 (t, 3H), 1.56 (s, 9H), 1.66 (m, 2H), 1.92 (m, 2H), 2.58 (t, 2H), 3.22 (m, 2H), 3.48 (t, 2H), 3.77 (m, 2H), 5.30 (s, 2H), 6.80 (s, 1H), 7.73 (s, 1H).

LMRS: m/z 450.6 (MH$^+$)

Preparation 55

Methyl (2RS)-2-amino-3-(1H-imidazol-2-yl)propanoate

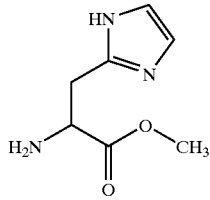

A mixture of the alkene from Preparation 57 (366 mg, 12 mmol) and 10% palladium on charcoal (50 mg) in methanol (8 ml) was hydrogenated at 3.5 atm and 50° C. for 18 hours. The cooled mixture was filtered through Arbocel™, washing through with methanol, and the filtrate concentrated under reduced pressure to afford the title compound, 200 mg, 98% yield.

$^1$H-NMR (CD$_3$OD, 400 MHz) δ: 3.65 (d, 2H), 3.80 (s, 3H), 4.60 (t, 1H), 7.55 (s, 2H).

LMRS: m/z 170.3 (MH$^+$)

Preparation 56

Methyl (2S)-2-amino-3-(1-{[2-(trimethylsilyl)ethoxy]methyl}-1H-imidazol-2-yl)propanoate

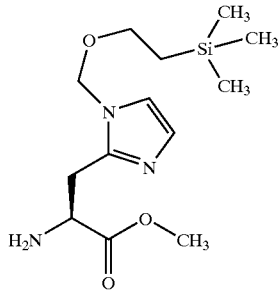

The product from Preparation 58 (950 mg, 2.40 mmol) was treated with aqueous hydrochloric acid (48 ml, 0.25N HCl, 12.0 mmol) and the resultant mixture was stirred at room temperature for 2 hours. The reaction was then basified with 0.88 ammonia to pH=9 and extracted with ethyl acetate (2×). The combined organic extracts were dried (Na$_2$SO$_4$), filtered, and then concentrated under reduced pressure. The residue was purified by column chromatography on silica gel eluting with ethyl acetate:methanol:0.88 ammonia (95:5:0.5) to give the title compound, 600 mg, 83% yield.

$^1$H-NMR (CDCl$_3$, 300 MHz) δ: −0.03 (s, 9H), 0.90 (t, 2H), 3.00 (dd, 1H), 3.20 (dd, 1H), 3.48 (t, 2H), 3.71 (s, 3H), 4.05 (m, 1H), 5.23 (dd, 2H), 6.92 (s, 1H), 6.97 (s, 1H).

LMRS: m/z 300.2 (MH$^+$)

Preparation 57

Methyl (2Z)-2-{[(benzyloxy)carbonyl]amino}-3-(1H-imidazol-2-yl)-2-propenoate

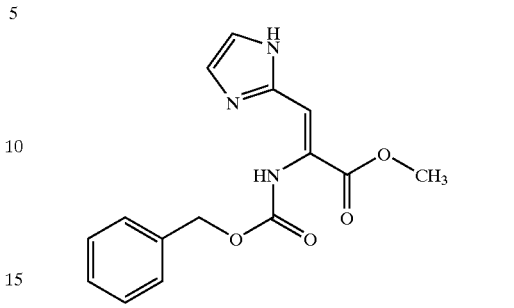

A mixture of methyl 2-{[(benzyloxy)carbonyl]amino}-3-(dimethoxyphosphoryl)-propanoate (1 g, 30 mmol) in tetrahydrofuran (7 ml) was stirred at −40° C. and tetramethylguanidine (380 mg, 33 mmol) was added. The reaction mixture was stirred at −40° C. for 20 minutes and then imidazole-2-carboxaldehyde (317 mg, 33 mmol) was added. The reaction was then allowed to warm to room temperature and was stirred at room temperature for 18 h. The solvent was then removed by evaporation under reduced pressure and the residue dissolved in ethyl acetate and washed with water and then brine. The organic phase was then dried (MgSO$_4$), filtered, and then concentrated under reduced pressure. The residue was purified by column chromatography on silica gel, eluting with a solvent gradient of ethyl acetate:pentane (30:70 to 80:20), to give the title compound, 366 mg, 40% yield.

$^1$H-NMR (CDCl$_3$, 300 MHz) δ: 3.77 (s, 3H), 5.17 (s, 2H), 6.44 (s, 1H), 7.10 (br s, 2H), 7.35 (m, 5H), 10.2 (br s, 1H).

LMRS: m/z 301.9 (MH$^+$)

Preparation 58

(2R,5R)-2-Isopropyl-3,6-dimethoxy-5-[(1-{[2-(trimethylsilyl)ethoxy]methyl}-1H-imidazol-2-yl)methyl]-2,5-dihydropyrazine

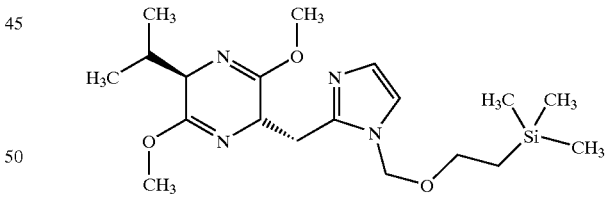

A solution of (2R)-2-isopropyl-3,6-dimethoxy-2,5-dihydropyrazine (111 mg, 0.60 mmol) in tetrahydrofuran (2.5 ml) was cooled to −78° C. and treated with n-butyl lithium (0.388 ml, 1.6M in hexanes, 0.62 mmol). The reaction was stirred at −78° C. for 45 minutes and the organic solution from Preparation 73 was added. The reaction was then allowed to warm to room temperature and was stirred for a further 18 hours. The reaction was then quenched by the addition of methanol and then the solvent was removed by evaporation under reduced pressure. The residue was diluted with water and ethyl acetate. The layers were separated and the aqueous phase was extracted with further ethyl acetate (2×). The combined organic extracts were then dried (Na$_2$SO$_4$), filtered, and then concentrated under reduced pressure. The residue was purified by column chromatography on silica gel, eluting with a solvent gradient of ethyl acetate:hexane (50:50 to 100:0), to give the title compound, 40 mg, 17% yield.

¹H-NMR (CDCl₃, 400 MHz) δ: −0.03 (s, 9H), 0.65 (d, 3H), 0.84 (t, 2H), 1.00 (d, 3H), 2.16 (m, 1H), 3.03 (dd, 1H), 3.39 (dd, 1H), 3.44 (t, 2H), 3.58 (s, 3H), 3.71 (s, 3H), 3.77 (m, 1H), 4.39 (m, 1H), 5.29 (dd, 2H), 6.90 (s, 1H), 6.95 (s, 1H).

LMRS: m/z 394.8 (MH⁺)

Preparation 59

Ethyl (2RS)-6-[benzyl(tert-butoxycarbonyl)amino]-2-(diethoxyphosphoryl)hexanoate

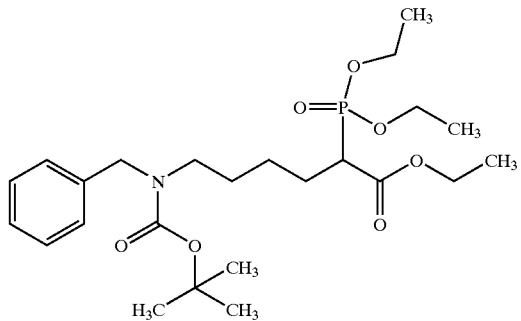

Triethyl phosphonoacetate (2.6 ml, 12.9 mmol) was added to a solution of sodium hydride (576 mg, 14.2 mmol) in tetrahydrofuran (75 ml), and the solution stirred at room temperature for 30 minutes. A solution of the iodide from Preparation 64 (5.0 g, 12.9 mmol) in tetrahydrofuran (10 ml), and 18-crown-6 (40 mg) were added, and the reaction heated under reflux for 18 hours. Aqueous ammonium chloride solution was added to the cooled reaction, and the mixture extracted with ethyl acetate (2×). The combined organic extracts were dried (MgSO₄), filtered, and concentrated under reduced pressure to give a yellow oil. The crude product was purified by column chromatography on silica gel, eluting with a solvent gradient of ethyl acetate:pentane (40:60 to 100:0), to give the title compound, 2.69 g, 49% yield.

¹H-NMR (CDCl₃, 300 MHz) δ: 1.21–1.37 (m, 9H), 1.38–1.58 (m, 13H), 1.80 (m, 1H), 1.96 (m, 1H), 2.80–2.98 (m, 1H), 3.05–3.25 (m, 2H), 4.16–4.24 (m, 6H), 4.40 (s, 2H), 7.18–7.37 (m, 5H).

Preparation 60

Ethyl (2RS)-2-(diethoxyphosphoryl)-5-(tritylamino)pentanoate

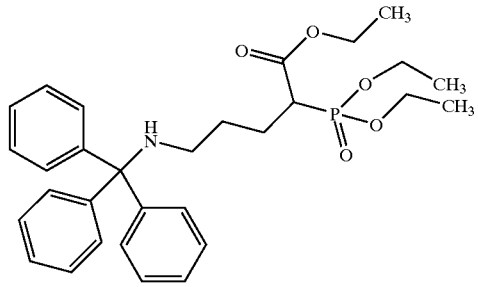

The title compound was prepared in 34% yield from the bromide from Preparation 62, following a similar procedure to that described in Preparation 59.

¹H-NMR (CDCl₃, 400 MHz) δ: 1.28 (m, 11H), 1.84–2.02 (m, 2H), 2.15 (t, 2H), 2.93 (m, 1H), 4.17 (m, 6H), 7.18 (m, 3H), 7.24 (m, 6H), 7.44 (d, 6H)

LMRS: m/z 524.4 (MH⁺)

Preparation 61

Methyl (2R)-2-chloro-3-(1H-imidazol-4-yl)propanoate

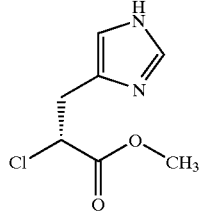

A cold solution of sodium nitrite (2.63 g, 38 mmol) in water (5 ml) was added dropwise to a stirred suspension of D-histidine (2 g, 11.5 mmol) in concentrated hydrochloric acid (30 ml) at −5° C. The mixture was stirred at 0° C. for 1 hour and then at room temperature for 17 hours. The mixture was cooled and basified with aqueous ammonium hydroxide solution (2N) until pH=4–5. The solvent was then removed by evaporation under reduced pressure to afford (2R)-2-chloro-3-(1H-imidazol-4-yl)propanoic acid.

¹H-NMR (D₂O, 300 MHz) δ: 3.25 (m, 2H), 4.45 (t, 1H), 7.12 (s, 1H), 8.15 (s, 1H).

LMRS: m/z 175.0 (MH⁺)

[α]_D=+13.51 (c 0.093, methanol)

Hydrogen chloride gas was bubbled through a stirred suspension of (2R)-2-chloro-3-(1H-imidazol-4-yl)propanoic acid in methanol (60 ml) at 0° C. for 20 minutes and the suspension was stirred at room temperature for 17 hours. The solvent was then removed by evaporation under reduced pressure and the chilled residue was suspended in cold aqueous saturated sodium bicarbonate solution (20 ml) and extracted with dichloromethane (4×20 ml). The combined organic extracts were dried (Na₂SO₄), filtered, and concentrated under reduced pressure. The residue was dissolved in diethyl ether and the resultant solution concentrated under reduced pressure to afford the title compound as an oil, 350 mg, 14% yield.

¹H-NMR (CDCl₃, 300 MHz) δ: 3.20 (dd, 1H), 3.37 (dd, 1H), 3.75 (s, 3H), 4.59 (m, 1H), 6.90 (s, 1H), 7.57 (s, 1H).

LMRS: m/z 189.0 (MH⁺)

[α]_D=+2.13 (c 0.16, methanol)

Preparation 62

N-(3-bromopropyl)-N-tritylamine

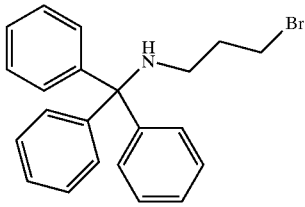

Triphenylphosphine (121 g, 0.46 mol) was added portionwise to an ice-cooled solution of the alcohol from Preparation 63 (139 g, 0.44 mol) and carbon tetrabromide (153 g, 0.46 mol) in dichloromethane (1360 ml) and, once addition was complete, the reaction was stirred at room temperature for 48 hours. The reaction was diluted with water, the layers separated, and the aqueous phase extracted with dichloromethane (2×). The combined organic extracts were dried (Na₂SO₄), filtered, and concentrated under reduced pressure. The crude product was purified by column chromatography on silica gel, eluting with a solvent gradient of hexane:ethyl acetate (99:1 to 95:5), to afford the title compound, 81.5 g, 49% yield.

¹H-NMR (CDCl₃, 300 MHz) δ: 2.02 (m, 2H), 2.28 (m, 2H), 3.58 (t, 2H), 7.19 (m, 3H), 7.27 (m, 6H), 7.46 (d, 6H).

Preparation 63

3-Hydroxy-N-trityl-1-propanamine

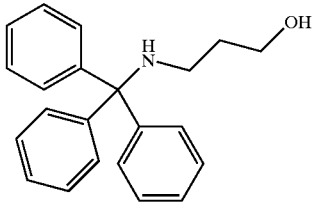

A mixture of 3-amino-1-propanol (51 ml, 0.66 mol), chlorotriphenylmethane (184 g, 0.66 mol) and triethylamine (92 ml, 0.66 mol) in dichloromethane (1000 ml) was stirred at room temperature for 18 hours. The reaction mixture was diluted with water and the layers separated. The aqueous phase was extracted with further dichloromethane (2×) and the combined organic extracts were dried (Na₂SO₄), filtered, and concentrated under reduced pressure. The residue was triturated well with diisopropyl ether, and the resulting solid was filtered and dried. This solid was then triturated with methanol, the suspension filtered, and the filtrate concentrated under reduced pressure, to give the title compound as a white solid, 139.1 g, 66% yield.

¹H-NMR (CDCl₃, 300 MHz) δ: 1.70 (m, 2H), 2.38 (t, 2H), 3.86 (t, 2H), 7.19 (m, 3H), 7.25 (m, 6H), 7.42 (d, 6H).

LMRS: m/z 318.4 (MH⁺)

Preparation 64 tert-Butyl benzyl (4-iodobutyl)carbamate

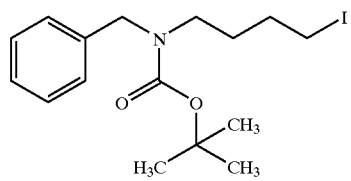

A mixture of the chloride from Preparation 65 (9.3 g, 31.3 mmol) and sodium iodide (14.9 g, 100 mmol) in acetone (200 ml) was heated under reflux for 18 hours. The cooled reaction mixture was concentrated under reduced pressure, and the residue partitioned between ether and water. The layers were separated and the aqueous phase extracted with ether. The combined organic extracts were then dried (Na₂SO₄), filtered, and concentrated under reduced pressure to afford the title compound as a yellow oil, 10.5 g, 87% yield.

¹H-NMR (CDCl₃, 300 MHz) δ: 1.40–1.65 (m, 11H), 1.79 (m, 2H), 3.19 (m, 4H), 4.42 (s, 2H), 7.20–7.38 (m, 5H).

LMRS: m/z 390 (MH⁺)

Preparation 65 tert-Butyl benzyl (4-chlorobutyl)carbamate

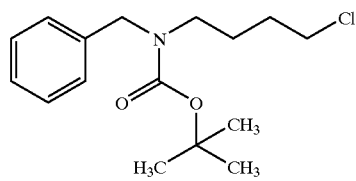

Tert-butyl benzylcarbamate (*J. Org. Chem.* 1993, 58, 56) (9.1 g, 44 mmol) was added to a solution of sodium hydride (2.14 g, 53 mmol) in tetrahydrofuran (160 ml), and the solution stirred at room temperature for 20 minutes. 1-Bromo-4-chlorobutane (5.07 ml, 44 mmol) was then added and the reaction heated under reflux for 18 hours. The cooled reaction was quenched by the addition of aqueous ammonium chloride solution, and the mixture extracted with ethyl acetate (2×). The combined organic extracts were dried (Na₂SO₄), filtered, and concentrated under reduced pressure. The crude product was purified by column chromatography on silica gel, eluting with acetate:pentane (95:5), to afford the title compound as a clear oil, 6.1 g, 47% yield.

¹H-NMR (CDCl₃, 300 MHz) δ: 1.45 (s, 9H), 1.58–1.80 (m, 4H), 3.14–3.30 (m, 2H), 3.52 (t, 2H), 4.42 (s, 2H), 7.25 (m, 5H).

LMRS: m/z 298.0 (MH⁺)

Preparation 66

1-Propyl-1H-imidazole-4-carboxaldehyde

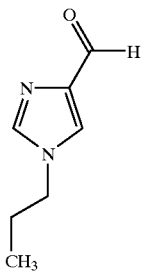

Imidazole-4-carboxaldehyde (30 g, 0.31 mol) was added portionwise to a solution of sodium hydride (13.9 g, 60% dispersion in mineral oil, 0.348 mol) in tetrahydrofuran (450 ml), and the solution stirred for 45 minutes. n-Propyl bromide (31.2 ml, 0.344 mol) was then added portionwise, followed by 18-crown-6 (150 mg), and the reaction heated under reflux for 18 hours. Aqueous ammonium chloride solution was added to the cooled reaction, and the mixture extracted with ethyl acetate (2×) and dichloromethane (2×). The combined organic extracts were dried ($MgSO_4$), filtered, and concentrated under reduced pressure. The crude product was purified by column chromatography on silica gel, eluting with ethyl acetate:pentane (40:60), to give the title compound, 20.2 g, 47% yield.

$^1$H-NMR (DMSO-$d_6$, 400 MHz) δ: 0.80 (t, 3H), 1.76 (m, 2H), 3.98 (t, 2H), 7.84 (s, 1H), 8.04 (s, 1H), 9.70 (s, 1H).

LMRS: m/z 277.3 (2M+H)$^+$

Preparation 67

1-n-Butyl-1H-imidazole-4-carboxaldehyde

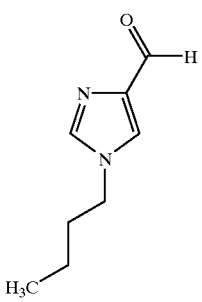

Imidazole-4-carboxaldehyde (10 g, 104 mmol) was added portionwise to a solution of sodium hydride (4.56 g, 60% dispersion in mineral oil, 114 mmol) in tetrahydrofuran (150 ml), and the solution stirred for 30 minutes. n-Butyl bromide (15.7 g, 114 mmol) was added portionwise, followed by 18-crown-6 (50 mg), and the reaction heated under reflux for 18 hours. Aqueous ammonium chloride solution was added to the cooled reaction and the mixture extracted with ethyl acetate (2×) and dichloromethane (2×). The combined organic extracts were then dried ($MgSO_4$), filtered, and concentrated under reduced pressure. The residue was purified by column chromatography on silica gel, eluting with a solvent gradient of pentane:ethyl acetate (50:50 to 25:75), to give the title compound, 4.45 g, 28% yield.

$^1$H-NMR (CDCl$_3$, 300 MHz) δ: 0.97 (t, 3H), 1.37 (m, 2H), 1.80 (m, 2H), 4.00 (t, 2H), 7.55 (s, 1H), 7.62 (s, 1H), 9.88 (s, 1H).

LMRS: m/z 153.3 (MH$^+$)

Preparation 68

1-{[2-(Trimethylsilyl)ethoxy]methyl}-1H-imidazole-4-carboxaldehyde

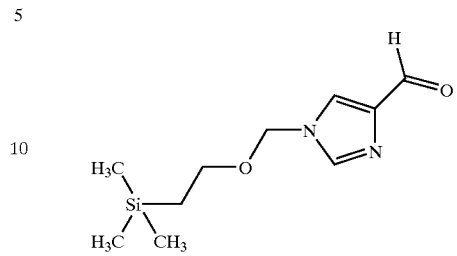

Imidazole-4-carboxaldehyde (1 g, 10.4 mmol) was added portionwise to a solution of sodium hydride (463 mg, 60% dispersion in mineral oil, 11.4 mmol) in N,N-dimethylformamide (15 ml), and the solution stirred for 30 minutes at room temperature. 2-(Trimethylsilyl)ethoxymethyl chloride (2.03 ml, 11.4 mmol) was added and the reaction stirred at room temperature for 18 hours. The reaction was quenched by the addition of aqueous ammonium chloride solution, and the mixture extracted with ethyl acetate (2×). The combined organic extracts were dried ($Na_2SO_4$), filtered, and concentrated under reduced pressure. The residue was purified by column chromatography on silica gel, eluting with methanol:ethyl acetate (3:97), to give the title compound, 1.8 g, 77% yield.

$^1$H-NMR (CDCl$_3$, 300 MHz) δ: −0.02 (s, 9H), 0.92 (t, 2H), 3.52 (t, 2H), 5.33 (s, 2H), 7.68 (s, 1H), 7.72 (s, 1H), 9.92 (s, 1H).

Preparations 69 and 70

4-Propyl-1-{[2-(trimethylsilyl)ethoxy]methyl}-1H-imidazole-2-carboxaldehyde (69)

5-Propyl-1-{[2-(trimethylsilyl)ethoxy]methyl}-1H-imidazole-2-carboxaldehyde (70)

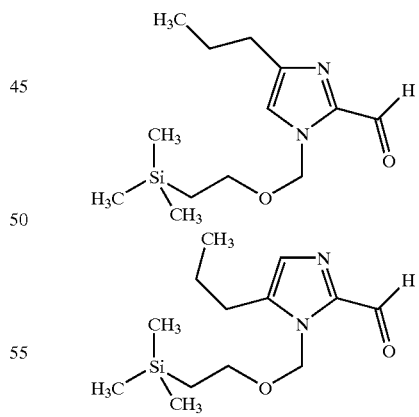

n-Butyl lithium (11.9 ml, 1.6M in hexanes, 19.14 mmol) was added dropwise to a cooled (−40° C.) solution of the imidazoles from Preparations 71 and 72 (4.6 g, 19.14 mmol) in tetrahydrofuran (75 ml) and, once addition was complete, the resulting red solution was stirred for 20 minutes. N,N-Dimethylformamide (1.36 ml, 19.14 mmol) was added dropwise over 15 minutes, and the reaction then allowed to warm to room temperature and stirred for 18 hours. The reaction was quenched by the addition of aqueous ammonium chloride, extracted with ether and the combined organic extracts were concentrated under reduced pressure. The crude product was purified by column chromatography on silica gel, eluting with hexane:ethyl acetate (75:25), to give the title compounds of Preparations 69 and 70 respectively in a 3:1 regioisomeric mixture, 3.4 g, 66% yield.

$^1$H-NMR (CDCl$_3$, 300 MHz) δ: −0.02 (s, 9H), 0.84–1.02 (m, 3H), 1.74 (m, 4H), 2.61 (m, 2H), 3.57 (m, 2H), 5.75 (s, 1.5H), 5.80 (s, 0.5H), 6.98 (s, 0.25H), 7.10 (s, 0.75H), 9.75 (s, 0.25H), 9.77 (s, 0.75H).

LMRS: m/z 269.0 (MH$^+$)

Preparations 71 and 72

4-n-Propyl-1-{[2-(trimethylsilyl)ethoxy]methyl}-1H-imidazole (71)

5-n-Propyl-1-{[2-(trimethylsilyl)ethoxy]methyl}-1H-imidazole (72)

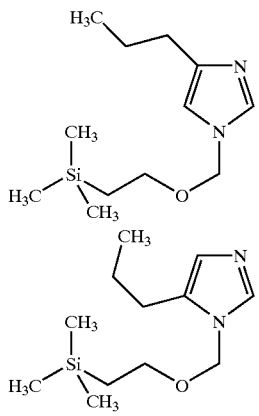

A solution of the imidazole from Preparation 76 (4.9 g, 44.6 mmol) in tetrahydrofuran (20 ml) was added dropwise to a solution of sodium hydride (1.96 g, 60% dispersion in mineral oil, 49.1 mmol) in tetrahydrofuran (20 ml) and, once addition was complete, the solution was stirred for an hour. The solution was cooled to 0° C. and 2-(trimethylsilyl)ethoxymethyl chloride (8.28 ml, 46.8 mmol) was added dropwise over 20 minutes. The reaction mixture was stirred at room temperature for 18 hours, then concentrated under reduced pressure. The residue was partitioned between ether and water, the layers separated, and the aqueous phase extracted with ether. The combined organic extracts were washed with brine, dried (MgSO$_4$), filtered, and concentrated under reduced pressure. The residual brown oil was purified by column chromatography on silica gel, eluting with dichloromethane:methanol (95:5), to afford the title compounds of Preparation 71 and 72 respectively in a regioisomeric mixture of 3:1, 7 g, 65% yield.

$^1$H-NMR (CDCl$_3$, 300 MHz) δ: 0.0 (s, 9H), 0.90 (m, 3H), 1.65 (m, 4H), 2.58 (m, 2H), 3.45 (m, 2H), 5.20 (s, 2H), 6.74 (s, 0.75H), 6.80 (s, 0.25H), 7.28 (s, 1H).

LMRS: m/z 241.1 (MH$^+$)

Preparation 73

2-(Chloromethyl)-1-{[2-(trimethylsilyl)ethoxy]methyl}-1H-imidazole

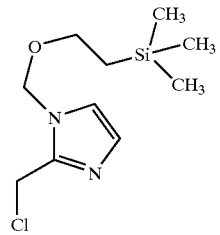

A solution of the alcohol (150 mg, 0.66 mmol) from Preparation 74 in dichloromethane (3.7 ml) was treated with triethylamine (0.138 ml, 0.99 mmol). Methanesulfonyl chloride (0.061 ml, 1.79 mmol) was then added and the reaction mixture was stirred for 1 hour. The reaction was then diluted with water and extracted with dichloromethane (2×). The combined organic extracts were dried (Na$_2$SO$_4$) and filtered. A small aliquot of the resultant solution was concentrated under reduced pressure to provide a sample of the title compound for characterisation. The remaining organic solution was concentrated to a small volume (0.5 ml) and diluted with tetrahydrofuran (5 ml). This organic solution was used directly in Preparation 58.

$^1$H-NMR (CDCl$_3$, 400 MHz) δ: 0.00 (s, 9H), 0.94 (t, 2H), 3.52 (t, 2H), 4.72 (s, 2H), 5.37 (s, 2H), 7.01 (s, 2H).

LMRS: m/z 247 (MH$^+$)

Preparation 74

(1-{[2-(Trimethylsilyl)ethoxy]methyl}-1H-imidazol-2-yl)methanol

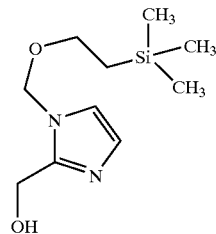

A solution of the aldehyde (2.3 g, 10.2 mmol) from Preparation 75 in methanol (30 ml) was cooled to −20° C. Sodium borohydride (462 mg, 12.2 mmol) was added portionwise to the stirred solution and the reaction was allowed to warm to room temperature over 1 hour. The reaction was quenched by the addition of aqueous ammonium chloride solution and the resultant mixture was extracted with dichloromethane (2×). The combined organic extracts were dried (Na$_2$SO$_4$), filtered, and concentrated under reduced pressure to give the title compound as a beige solid, 2.15 g, 93% yield.

$^1$H-NMR (CDCl$_3$, 400 MHz) δ: −0.03 (s, 9H), 0.90 (t, 2H), 3.52 (t, 2H), 4.71 (s, 2H), 5.35 (s, 2H), 6.94 (s, 1H), 6.97 (s, 1H).

Preparation 75

1-{[2-(Trimethylsilyl)ethoxy]methyl}-1H-imidazole-2-carboxaldehyde

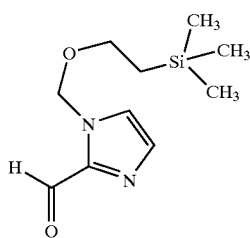

Sodium hydride (463 mg, 60% dispersion in mineral oil, 11.4 mmol) was washed with hexane under an atmosphere of dry nitrogen. N,N-Dimethylformamide (15 ml) was added, the resultant mixture was stirred at room temperature and imidazole-2-carboxaldehyde (1 g, 10.4 mmol) was added portionwise. The reaction was then stirred for 1.5 hours, 2-(trimethylsilyl)ethoxy methyl chloride (2.03 ml, 11.4 mmol) was added, and the resultant mixture was then stirred at room temperature for 18 hours. The reaction was quenched by the addition of aqueous ammonium chloride solution and the resultant mixture then extracted with ethyl acetate (2×). The combined organic extracts were dried ($Na_2SO_4$), filtered, concentrated under reduced pressure and then azeotroped with xylene to give the title compound, 2.3 g, 98% yield.

$^1$H-NMR (CDCl$_3$, 400 MHz) δ: −0.03 (s, 9H), 0.90 (t, 2H), 3.55 (t, 2H), 5.77 (s, 2H), 7.32 (s, 1H), 7.35 (s, 1H), 9.84 (s, 1H).

Preparation 76

4-Propyl-1H-imidazole

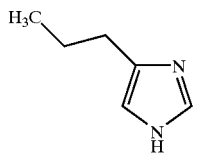

A mixture of 2-bromopentanal (15 g, 91 mmol) (Bull. Chim. Soc. Fr. 1973, 1465) and formamide (32 ml, 806 mmol) were heated at 180° C. for 8 hours, then allowed to cool. Excess formamide was removed by vacuum distillation, and the residue partitioned between aqueous sodium bicarbonate solution and ethyl acetate. The layers were separated, and the organic phase was concentrated under reduced pressure. The crude product was purified by column chromatography on silica gel, eluting with a solvent gradient of dichloromethane:methanol (93:7 to 90:10), to give the title compound, 9 g, 90% yield.

$^1$H-NMR (CDCl$_3$, 300 MHz) δ: 0.98 (t, 3H), 1.67 (m, 2H), 2.60 (t, 2H), 6.79 (s, 1H), 7.25 (s, 1H), 7.58 (s, 1H).

LMRS: m/z 221 (2M+H)$^+$

Preparation 77 tert-Butyl N-(2-oxobutyl)carbamate

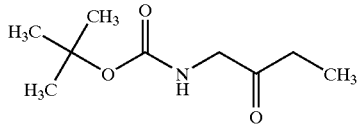

Ethyl magnesium bromide (1M solution in tetrahydrofuran, 13.7 ml, 13.7 mmol)) was added to a stirred solution of tert-butyl 2-[methoxy(methyl)amino]-2-oxoethylcarbamate (Synth. Commun. 1988, 18, 2273) (1 g, 4.58 mmol) in tetrahydrofuran (25 ml) at 0° C. then stirred at 0° C. for 15 minutes. The solution was allowed to warm to room temperature and was stirred for 45 minutes. Ethyl acetate (5 ml) was added, followed by saturated ammonium chloride solution. The aqueous phase was extracted with ethyl acetate. The combined organic extracts were washed with saturated aqueous sodium hydrogen carbonate solution and brine. The organic phase was then dried ($Na_2SO_4$), filtered, and concentrated under reduced pressure. The residue was purified by column chromatography on silica gel, eluting with a solvent gradient of hexane:ethyl acetate (85:15 to 70:30), to afford the title compound as a colorless oil, 730 mg, 84% yield.

$^1$H-NMR (CDCl$_3$, 300 MHz) δ: 1.10 (t, 3H), 1.43 (s, 9H), 2.45 (q, 2H), 4.01 (m, 2H), 5.22 (br s, 1H).

LMRS: m/z 187.9 (MH$^+$), 204.9 (MNH$_4^+$)

TLC: hexane:ethyl acetate (70:30) Rf=0.41

Preparations 78 and 79

The compounds of the following tabulated Preparations of the general formula:

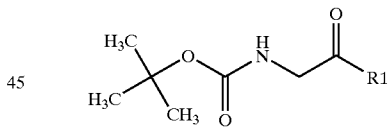

were prepared by a similar method to that of Preparation 77 using tert-butyl 2-[methoxy(methyl)amino]-2-oxoethylcarbamate (Synth. Commun. 1988, 18, 2273 and the appropriate Grignard starting materials.

| Prep. No. | R$^1$ | Yield (%) | Analytical Data |
|---|---|---|---|
| 78 | ![benzyl] | 12 | $^1$H-NMR(CDCl$_3$, 300 MHz) δ: 1.41 (s, 9H), 3.72(s, 2H), 4.05(d, 2H), 5.15(d, 1H), 7.17–7.40(m, 5H). |
| 79 | ‑CH(CH$_3$)$_2$ | 58 | $^1$H-NMR(CDCl$_3$, 300 MHz) δ: 1.15 (d, 6H), 1.43(s, 9H), 2.82(d, 1H), 4.07(d, 2H), 5.25(br s, 1H). |

Preparation 80 tert-Butyl (1S)-1-methyl-2-oxopropylcarbamate

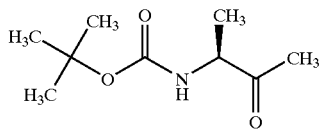

Methyl magnesium bromide (3.0M solution in diethyl ether, 4.3 ml, 12.9 mmol) was added to a stirred solution of tert-butyl (1S)-2-[methoxy(methyl)amino]-1-methyl-2-oxoethylcarbamate (Tetrahedron: Asymmetry 1996, 7, 985) (1 g, 4.3 mmol) in anhydrous tetrahydrofuran (20 ml) at −60° C. under a nitrogen atmosphere. The mixture was allowed to warm to 0° C. and to then room temperature and was stirred at room temperature for 1 hour. Aqueous saturated ammonium chloride was added and aqueous phase was extracted with diethyl ether (2×76 ml). The combined organic extracts were then washed with saturated aqueous ammonium chloride solution and brine. The organic phase was then dried (MgSO$_4$), filtered, and concentrated under reduced pressure. The residue was purified by column chromatography on silica gel, eluting with a solvent gradient of dichloromethane:methanol (99:1 to 98:2), to afford the title compound as a colorless solid, 412 mg, 51% yield.

$^1$H-NMR (CDCl$_3$, 300 MHz) δ: 1.35 (d, 3H), 1.45 (s, 9H), 2.20 (s, 3H), 4.30 (m, 1H), 5.22 (br s, 1H).

Preparation 81

(±)-2-Methoxy-1-methylethyl 4-methylbenzenesulfonate

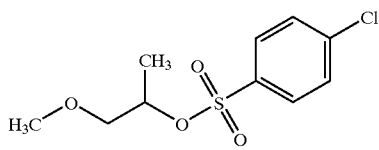

A solution of 1-methoxy-2-propanol in dichloromethane (2.3 g, 25.5 mmol) (25 ml) and pyridine (5 ml) was cooled to between −5 and 0° C. 4-Methylbenzenesulfonyl chloride (5.35 g, 28.1 mmol) was added dropwise and the mixture was stirred at 0° C. for 15 minutes. The mixture was then stirred at room temperature for 18 hours. Ice was added and the mixture was stirred for 1 hour. The organic phase was separated, washed with 10% aqueous sulfuric acid (4×) and water (1×), and then dried (MgSO$_4$) and filtered. The filtrate was purified by column chromatography on silica gel eluting with dichloromethane. The solution obtained was dried (MgSO$_4$), filtered, and concentrated under reduced pressure to afford the title compound as a colorless oil, 4.3 g, 69% yield.

$^1$H-NMR (CDCl$_3$, 400 MHz) δ: 1.27 (d, 3H), 2.43 (s, 3H), 3.23 (s, 3H), 3.37 (m, 2H), 4.70 (m, 1H), 7.32 (d, 2H), 7.80 (d, 2H).

LMRS: m/z 262.0 (MNH$_4^+$)

Preparation 82

Methyl (2S)-2-[(tert-butoxycarbonyl)amino]-3-[1-(4,4,4-trifluorobutyl)-1H-imidazol-4-yl]propanoate

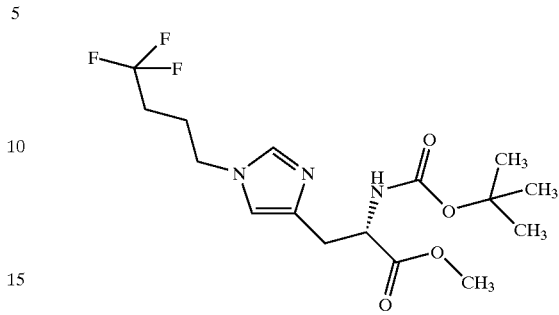

Cesium carbonate (1.95 g, 6 mmol) and 1-bromo-4,4,4-trifluorobutane (954 mg, 5 mmol) were added to a solution of methyl (2S)-2-[(tert-butoxycarbonyl)amino]-3-(1H-imidazol-4-yl)propanoate (1.08 g, 4 mmol) in N,N-dimethylformamide (5 ml), and the reaction stirred at 70° C. for 3 hours. The cooled mixture was concentrated under reduced pressure and the residue partitioned between ethyl acetate (150 ml) and water (50 ml). The layers were separated, the organic phase dried (MgSO$_4$), filtered, and concentrated under reduced pressure. The crude product was purified by column chromatography on silica gel using an elution gradient of cyclohexane:ethyl acetate (100:0 to 0:100) to afford the title compound as an oil, 840 mg, 55% yield.

$^1$H-NMR (CDCl$_3$, 400 MHz) δ: 1.41 (s, 9H), 2.01 (m, 4H), 3.01 (m, 2H), 3.68 (s, 3H), 3.98 (t, 2H), 4.57 (m, 1H), 5.84 (m, 1H), 6.66 (s, 1H), 7.38 (s, 1H).

LMRS: m/z 380.3 (MH$^+$)

[α]$_D$=−0.81 (c 0.148, methanol)

Preparation 83

Methyl (2S)-2-[(tert-butoxycarbonyl)amino]-3-[1-(1,3-thiazol-5-ylmethyl)-1H-imidazol-4-yl]propanoate

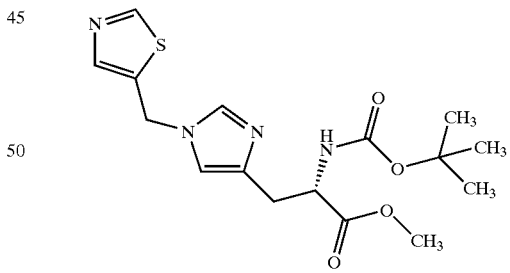

The title compound was obtained as an oil in 20% yield, from methyl (2S)-2-[(tert-butoxycarbonyl)amino]-3-(1H-imidazol-4-yl)propanoate and 5-(chloromethyl)-1,3-thiazole hydrochloride (EP 373891), following a similar procedure to that described in preparation 82, except methanol:ethyl acetate (10:90) was used as the column eluant.

$^1$H-NMR (CDCl$_3$, 400 MHz) δ: 1.41 (s, 9H), 3.03 (m, 2H), 3.65 (s, 3H), 4.55 (m, 1H), 5.22 (s, 2H), 5.86 (m, 1H), 6.78 (s, 1H), 7.01 (s, 1H), 7.50 (s, 1H), 8.80 (s, 1H).

LMRS: m/z 367.1 (MH$^+$)

Preparation 84

Methyl (2S)-2-[(tert-butoxycarbonyl)amino]-3-{1-[2-(2-pyridinyl)ethyl]-1H-imidazol-4-yl}propanoate

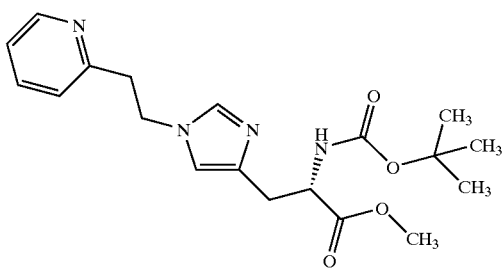

The title compound was obtained in 16% yield, from methyl (2S)-2-[(tert-butoxycarbonyl)amino]-3-(1H-imidazol-4-yl)propanoate and 2-(2-bromoethyl)pyridine hydrobromide (J. Het. Chem. 1973, 10, 39) following a similar procedure to that described in preparation 82, except methanol:ethyl acetate was used as the column eluant.

$^1$H-NMR (CDCl$_3$, 400 MHz) δ: 1.41 (s, 9H), 2.95 (m, 1H), 3.03 (m, 1H), 3.18 (t, 2H), 3.65 (s, 3H), 4.32 (t, 2H), 4.50 (m, 1H), 5.80 (m, 1H), 6.58 (s, 1H), 6.95 (d, 1H), 7.15 (m, 1H), 7.20 (s, 1H), 7.58 (m, 1H), 8.58 (d, 1H).

LMRS: m/z 375.2 (MH$^+$)

Preparation 85

Methyl (2S)-2-[(tert-butoxycarbonyl)amino]-3-(1-phenyl-1H-imidazol-4-yl)propanoate

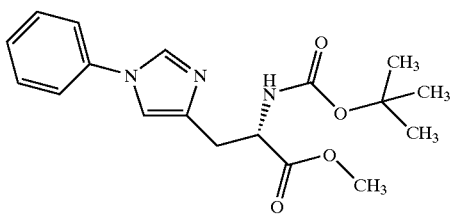

Phenylboronic acid (2.44 g, 20 mmol), copper acetate (2.72 g, 15 mmol), 4 Å molecular sieves (3 g) and pyridine (1.62 ml, 20 mmol) were added to a solution of methyl (2S)-2-[(tert-butoxycarbonyl)amino]-3-(1H-imidazol-4-yl) propanoate (2.69 g, 10 mmol) in dichloromethane (60 ml), and the reaction mixture stirred at room temperature whilst bubbling through compressed air, for 2 days. A solution of ethylenediaminetetraacetic acid (5 g, 17 mmol) in saturated sodium bicarbonate solution (200 ml) was added and the mixture stirred at room temperature for 20 minutes. The phases were separated, the aqueous layer extracted with dichloromethane (2×100 ml), and the combined organic extracts dried (MgSO$_4$), filtered, and concentrated under reduced pressure. The residue was azeotroped with toluene (300 ml), and then purified by column chromatography on silica gel using an elution gradient of pentane:ethyl acetate (100:0 to 40:60), to afford the title compound as a yellow gum, 1.87 g, 52% yield.

$^1$H-NMR (CDCl$_3$, 400 MHz) δ: 1.42 (s, 9H), 3.05–3.19 (m, 2H), 3.72 (s, 3H), 4.60 (m, 1H), 5.84 (m, 1H), 7.04 (s, 1H), 7.36 (m, 3H), 7.46 (m, 2H), 7.78 (s, 1H).

LMRS: m/z 346.1 (MH$^+$)

Anal. Found: C, 60.59; H, 6.56; N, 11.57. C$_{18}$H$_{23}$N$_3$O$_4$.0.75H$_2$O requires C, 60.24; H, 6.88; N, 11.71%.

[α]$_D$=+10.64 (c 0.126, methanol)

Preparation 86

Methyl (2S)-2-amino-3-[1-(4,4,4-trifluorobutyl)-1H-imidazol-4-yl]propanoate dihydrochloride

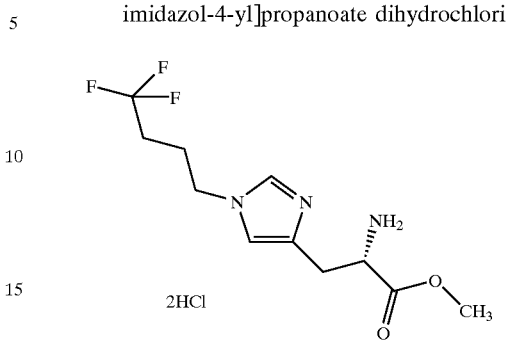

4M Hydrochloric acid in dioxan (5 ml) was added to the protected amine from preparation 82 (830 mg, 2.19 mmol), in an ice-cooled flask. The solution was allowed to warm to room temperature, and stirred for 3 hours. The mixture was concentrated under reduced pressure, the residue azeotroped with ethyl acetate (3×100 ml), then dried in vacuo, to afford the title compound as a white foam in quantitative yield.

$^1$H-NMR (D$_2$O, 400 MHz) δ: 2.00–2.19 (m, 4H), 3.28 (m, 2H), 3.70 (s, 3H), 4.17 (t, 2H), 4.37 (t, 1H), 7.40 (s, 1H), 8.62 (s, 1H).

LMRS: m/z 280.1 (MH$^+$)

[α]$_D$=+14.60 (c 0.1, methanol)

Preparation 87

Methyl (2S)-2-amino-3-[1-phenyl-1H-imidazol-4-yl] propanoate dihydrochloride

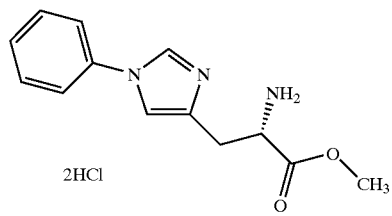

The title compound was obtained in 90% yield as a yellow solid, after trituration from diethyl ether, from the protected amine from preparation 85, following a similar procedure to that described in preparation 86.

$^1$H-NMR (D$_2$O, 400 MHz) δ: 3.40 (m, 2H), 3.77 (s, 3H), 4.42 (t, 1H), 7.50 (m, 5H), 7.77 (s, 1H), 9.00 (s, 1H).

LMRS: m/z 246 (MH$^+$)

Anal. Found: C, 47.86; H, 5.51; N, 12.61. C$_{13}$H$_{17}$N$_3$O$_2$Cl$_2$.1.0H$_2$O requires C, 47.72; H, 5.54; N, 12.84%.

[α]$_D$=+12.55 (c 0.11, methanol)

Preparation 88

Methyl (2S)-2-amino-3-[1-(1,3-thiazol-5-ylmethyl)-1H-imidazol-4-yl]propanoate dihydrochloride

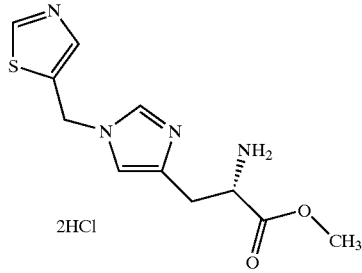

4M Hydrochloric acid in dioxan (6 ml) was added to the protected amine from preparation 83 (1.3 g, 3.5 mmol) in an ice-cooled flask. Water (5 ml) followed by concentrated hydrochloric acid were then added, and the solution stirred at room temperature for 18 hours. The mixture was concentrated under reduced pressure and azeotroped with ethanol to afford the title compound, 1.2 g, 100% yield.

$^1$H-NMR (CD$_3$OD, 400 MHz) δ: 3.30–3.46 (m, 2H), 3.81 (s, 3H), 4.43 (m, 1H), 5.62 (s, 2H), 7.63 (s, 1H), 7.95 (s, 1H), 9.10 (s, 1H), 9.18 (s, 1H).

LMRS: m/z 267.0 (MH$^+$)

$[α]_D$=+14.60 (c 0.1, methanol)

Preparation 89

Methyl (2S)-2-amino-3-{1-[2-(2-pyridinyl)ethyl]-1H-imidazol-4-yl}propanoate dihydrochloride

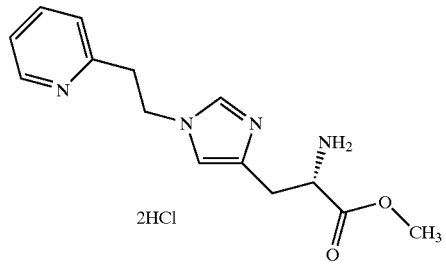

The title compound was obtained as a gum in 95% yield, from the protected amine from preparation 84, following the procedure described in preparation 88.

$^1$H-NMR (D$_2$O, 400 MHz) δ: 3.30 (m, 2H), 3.58 (m, 4H), 3.70 (s, 3H), 4.36 (m, 1H), 7.40 (s, 1H), 7.78 (d, 1H), 7.85 (dd, 1H), 8.41 (dd, 1H), 8.61 (m, 2H).

LMRS: m/z 275.1 (MH$^+$)

Preparation 90

Methyl (2S)-2-({2-[(tert-butoxycarbonyl)amino]ethyl}amino)-3-(1-methyl-1H-imidazol-4-yl)propanoate

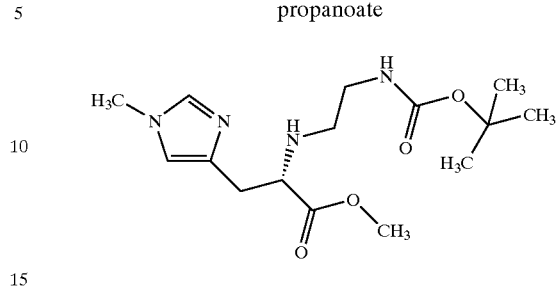

Methyl (2S)-2-amino-3-(1-methyl-1H-imidazol-4-yl)propanoate dihydrochloride (1.06 g, 4 mmol), sodium acetate (1.3 g, 16 mmol) and 4 Å molecular sieves (500 mg) were added to a solution of tert-butyl N-(2-oxoethyl)carbamate (637 mg, 4 mmol) in methanol (10 ml), and the solution stirred for 10 minutes. Sodium cyanoborohydride (1.3 g, 16 mmol) was then added, and the reaction stirred at room temperature for 72 hours. 2M Hydrochloric acid (2 ml) and water (50 ml) were added, and the solution then basified using saturated sodium bicarbonate solution. The mixture was extracted with ethyl acetate (5×100 ml), the combined organic extracts dried (MgSO$_4$), filtered, and concentrated under reduced pressure. The crude product was purified by column chromatography on silica gel using an elution gradient of ethyl acetate:methanol:diethylamine (100:0:0 to 96:2:2) to afford the title compound as a colorless oil, 220 mg, 17% yield.

$^1$H-NMR (CDCl$_3$, 400 MHz) δ: 1.41 (s, 9H), 2.62 (m, 1H), 2.77–2.86 (m, 2H), 2.98 (dd, 1H), 3.18 (m, 2H), 3.60 (m, 4H), 3.70 (s, 3H), 5.38 (m, 1H), 6.63 (s, 1H), 7.34 (s, 1H).

LMRS: m/z 327.2 (MH$^+$)

$[α]_D$=−1.48 (c 0.108, methanol)

Preparation 91

Methyl (2S)-2-({2-[(tert-butoxycarbonyl)amino]ethyl}amino)-3-[1-(4,4,4-trifluorobutyl)-1H-imidazol-4-yl]propanoate

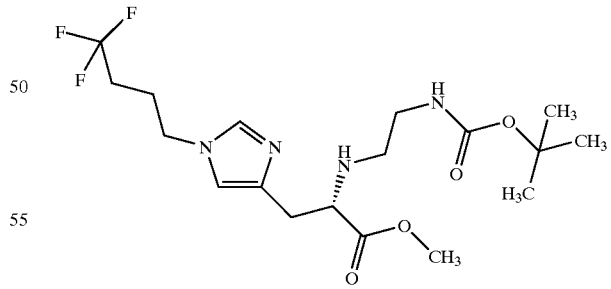

4 Å Molecular sieves (500 mg) and tert-butyl N-(2-oxoethyl)carbamate (350 mg, 2.2 mmol) were added to a solution of the amine from preparation 86 (780 mg, 2.2 mmol) in methanol (5 ml), and the mixture stirred for 20 minutes. Sodium cyanoborohydride (276 mg, 4.4 mmol) was added, and the reaction stirred at room temperature for 18 hours. 2M Hydrochloric acid (5 ml) was added, the mixture then neutralized using sodium bicarbonate solution, and filtered through Arbocel®. The filtrate was concentrated under reduced pressure and the residue partitioned between ethyl acetate (100 ml) and water (20 ml). The layers were separated and the organic layer was dried (MgSO$_4$), filtered, and concentrated under reduced pressure. The crude product was purified by column chromatography on silica gel using an elution gradient of ethyl acetate:methanol (100:0 to 90:10) to afford the title compound as a colorless oil, 300 mg, 32% yield.

$^1$H-NMR (CDCl$_3$, 400 MHz) δ: 1.42 (s, 9H), 2.02 (m, 4H), 2.62 (m, 1H), 2.78–2.92 (m, 2H), 2.98 (dd, 1H), 3.18 (m, 2H), 3.60 (t, 1H), 3.68 (s, 3H), 3.98 (t, 2H), 5.40 (m, 1H), 6.70 (s, 1H), 7.38 (s, 1H).

LMRS: m/z 423.2 (MH$^+$)

[α]$_D$=+2.0 (c 0.1, methanol)

Preparations 92 to 94

The following compounds of general structure:

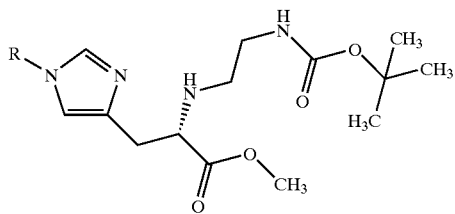

were prepared from the appropriate amines (preparations 87–89) and tert-butyl N-(2-oxoethyl)carbamate, following a similar procedure to that described in preparation 91.

Preparation 95

(7S)-2-Benzyl-6-{2-[(tert-butoxycarbonyl)amino]ethyl}-7-(methoxycarbonyl)-5-oxo-5,6,7,8-tetrahydroimidazo[1,5-c]pyrimidin-2-ium bromide

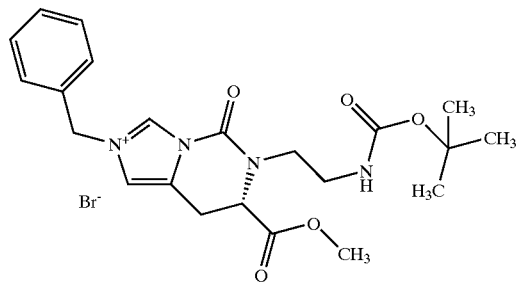

Benzyl bromide (119 μl, 1 mmol) was added to a solution of the compound from preparation 48 (270 mg, 0.8 mmol) in acetonitrile (5 ml), and the mixture heated at 60° C. for 18 hours. The cooled mixture was concentrated under reduced pressure and the residue purified by column chromatography on silica gel using an elution gradient of dichloromethane:methanol (100:0 to 90:10) to afford the title compound, 299 mg, 59% yield.

$^1$H-NMR (DMSOd$_6$, 400 MHz) δ: 1.28 (s, 9H), 3.18 (m, 3H), 3.42 (m, 2H), 3.61 (s, 3H), 3.95 (m, 1H), 4.85 (m, 1H), 5.42 (dd, 2H), 6.94 (m, 1H), 7.38–7.48 (m, 5H), 7.64 (s, 1H), 10.08 (s, 1H).

LMRS: m/z 430 (M$^+$)

[α]$_D$=+42.09 (c 0.096, methanol)

| Prep. No. | R | Yield (%) | Analytical Data |
|---|---|---|---|
| 92[1] | thiazol-5-ylmethyl | 12 oil | $^1$H-NMR(CDCl$_3$, 400 MHz) δ: 1.38(s, 9H), 2.58(m, 1H), 2.70–2.84(m, 2H), 2.92(dd, 1H), 3.10(m, 2H), 3.58(dd, 1H), 3.62(s, 3H), 5.19(s, 2H), 5.38(m, 1H), 6.75(s, 1H), 7.00 (s, 1H), 7.44(s, 1H), 8.77(s, 1H). LRMS: m/z 410.0(MH$^+$) |
| 93 | 2-(pyridin-2-yl)ethyl | 35 oil | $^1$H-NMR(CDCl$_3$, 400 MHz) δ: 1.42(s, 9H), 2.60(m, 1H), 2.75–2.84 (m, 2H), 2.94(dd, 1H), 3.18(m, 4H), 3.58(t, 1H), 3.68(s, 3H), 4.35(t, 2H), 5.41(m, 1H), 6.61(s, 1H), 6.98 (d, 1H), 7.18(m, 1H), 7.22(s, 1H), 7.58(m, 1H), 8.58(d, 1H). LRMS: m/z 418.2(MH$^+$) [α]$_D$ = +2.52 (c 0.103, methanol) |
| 94[2] | benzyl | 10 gum | $^1$H-NMR(CDCl$_3$, 400 MHz) δ: 1.41(s, 9H), 2.65(m, 1H), 2.81(m, 1H), 2.96(dd, 1H), 3.03(dd, 1H), 3.19 (m, 2H), 3.70(m, 4H), 5.38(m, 1H), 7.08(s, 1H), 7.37(m, 3H), 7.45(m, 2H), 7.78(s, 1H). LRMS: m/z 389.2(MH$^+$) |

Footnotes:

[1]The product was further purified by column chromatography on silica gel, using ethyl acetate:methanol:diethylamine(90:5:5) as eluant

[2]The product was additionally purified by column chromatography on reverse phase polystyrene gel using water:methanol (100:0 to 0:100) as eluant.

Preparation 96

1-Isopentyl-1H-imidazole-4-carboxaldehyde

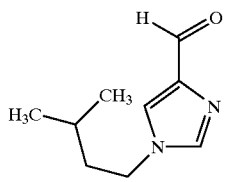

A mixture of sodium hydride (20 g, 60% dispersion in mineral oil, 0.5 mol) in tetrahydrofuran (300 ml) was cooled to 0° C., and 2-imidazolecarboxaldehyde (45 g, 0.47 mol) was added portionwise over 30 minutes. Once addition was complete, the reaction was stirred at 0° C. for 30 minutes, then allowed to warm to room temperature. 1-Bromo-3-methylbutane (60.8 ml, 0.5 mol) and 18-crown-6 (140 mg) were added, and the reaction was heated at reflux for 18 hours. The cooled reaction was quenched by the addition of water (400 ml), and the resulting mixture extracted with dichloromethane (800 ml in total). The combined organic extracts were dried ($MgSO_4$) and evaporated under reduced pressure. The residual orange oil was purified by column chromatography on silica gel using an elution gradient of ethyl acetate:pentane:methanol (40:60:0 to 100:0:0 to 98:0:2) to afford the title compound, 19.6 g.

Further purification of impure fractions using a Biotage® silica gel column, and ethyl acetate:cyclohexane (40:60) as eluant afforded a further 11.4 g of the title compound. Combination of the two batches provided 31 g of the title compound, 41% yield.

$^1$H-NMR ($CDCl_3$, 400 MHz) δ: 0.90 (d, 6H), 1.52 (m, 1H), 1.63 (dt, 2H), 3.97 (t, 2H), 7.47 (s, 1H), 7.58 (s, 1H), 9.80 (s, 1H).

LMRS: m/z 189 ($MNa^+$)

Anal. Found: C, 63.73; H, 8.43; N, 16.36. $C_9H_{14}N_2O;0.2H_2O$ requires C, 63.65;, 8.55; N, 16.50%.

Preparation 97 tert-Butyl 3-[hydroxy(1-isopentyl-1H-imidazol-4-yl)methyl]-2-oxo-1-piperidinecarboxylate

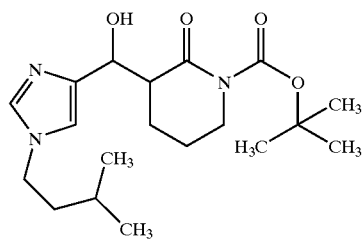

Lithium diisopropylamide (6.5 ml, 2M in heptane/tetrahydrofuran/ethylbenzene, 13 mmol) was added dropwise over 5 minutes to a cooled (−78° C.) solution of tert-butyl 2-oxo-1-piperidinecarboxylate (*J. Org. Chem.*, 1983, 48, 2424; *J. Chem. Soc.*, I, 1989, 721) (2.6 g, 13 mmol) in tetrahydrofuran (25 ml), so as to maintain a temperature below −70° C. Once addition was complete, the solution was stirred for 30 minutes, then allowed to warm to −10° C., and stirred for a further 30 minutes, before recooling to −78° C. A solution of the aldehyde from preparation 96 (1.66 g, 10 mmol) in tetrahydrofuran (5 ml) was added dropwise so as to maintain the temperature below −70° C., and once addition was complete, the reaction was stirred for 30 minutes. Saturated ammonium chloride solution (30 ml) was added, the mixture allowed to warm to room temperature and then partitioned between water and ethyl acetate. The layers were separated, the aqueous phase extracted with ethyl acetate, and the combined organic extracts dried ($MgSO_4$), filtered and concentrated under reduced pressure. The resulting yellow oil was purified by column chromatography on silica gel using an elution gradient of ethyl acetate:diethylamine:methanol (100:0:0 to 88:6:6) to afford the title compound, 1.1 g, 30% yield.

$^1$H-NMR ($CDCl_3$, 400 MHz) (mixture of diastereoisomers) δ: 0.90 (d, 6H), 1.46–1.64 (m, 13H), 1.76 (m, 3H), 2.98 (m, 1H), 3.52 (m, 1H), 3.74 (m, 1H), 3.84 (t, 2H), 4.08, 4.90 (2×m, 1H), 4.58, 5.34 (2×m, 1H), 6.85 (2×s, 1H) 7.35 (2×s, 1H).

LMRS: m/z 388 ($MNa^+$)

Preparation 98

3-[Hydroxy(1-isopentyl-1H-imidazol-4-yl)methyl]-1-methyl-2-piperidinone

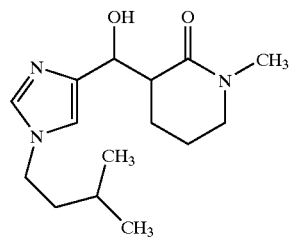

The title compound was obtained in 67% yield from the aldehyde from preparation 96 and 1-methyl-2-piperidinone, following the procedure described in preparation 97.

$^1$H-NMR ($CDCl_3$, 400 MHz) (mixture of diastereoisomers) δ: 0.88 (2×d, 6H), 1.35–1.82 (m, 7H), 2.67, 2.81 (m, 1H), 2.88, 2.94 (2×s, 3H), 3.18, 3.22 (m, 2H), 3.84 (t, 2H), 4.78 (m, 1H), 5.04 (m, 1H), 6.83 (2×s, 1H), 7.32 (2×s, 1H).

LMRS: m/z 302 ($MNa^+$)

Preparation 99 tert-Butyl 3-[hydroxy(1-propyl-1H-imidazol-4-yl)methyl]-2-oxo-1-piperidinecarboxylate

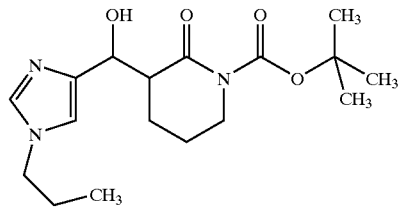

Lithium bis(trimethylsilyl)amide (244 ml, 1M in tetrahydrofuran, 244 mmol) was added dropwise over an hour to a cooled (−75° C.) solution of tert-butyl 2-oxo-1-piperidinecarboxylate (*J. Org. Chem.* 1983, 48, 2424; *J. Chem. Soc.* I, 1989, 721) (48.7 g, 244 mmol) in tetrahydrofuran (200 ml) under nitrogen, so as to maintain the temperature below −70° C. The mixture was warmed to 0° C., stirred for 90 minutes, then re-cooled to −75° C. A solution of the imidazole from preparation 66 (26.0 g, 188 mmol) in tetrahydrofuran (86 ml) was added dropwise over 30 minutes, and once addition was complete, the reaction was stirred for 2 hours at −75° C. The mixture was poured into 15% aqueous citric acid solution (650 ml), and extracted with ethyl acetate (3×250 ml). The aqueous solution was basified to pH 8 using 10% sodium hydroxide, and extracted with dichloromethane (3×250 ml). These organic extracts were dried and concentrated under reduced pressure to give the title compound as a pale yellow solid, 54.1 g.

The ethyl acetate extracts from above were combined, evaporated under reduced pressure and the residue re-suspended in 10% aqueous citric acid solution (100 ml). This was extracted with ethyl acetate (3×50 ml), and the aqueous basified to pH 8 using 10% sodium hydroxide solution. The aqueous solution was extracted with dichloromethane (3×50 ml), and these organic extracts dried and evaporated under reduced pressure to give additional product as a pale yellow solid, 22.4 g. Overall yield of the title compound was thus 76.5 g, 93% yield.

$^1$H-NMR (CDCl$_3$, 300 MHz) (mixture of diastereoisomers) δ: 0.88 (t, 3H), 1.52 (s, 9H), 1.78 (m, 6H), 3.00 (m, 1H), 3.58 (m, 2H), 3.74 (m, 1H), 3.82 (t, 2H), 5.38 (d, 1H), 6.87 (s, 1H), 7.38 (s, 1H).

Preparation 100 tert-Butyl 3-[hydroxy(1-trityl-1H-imidazol-4-yl)methyl]-2-oxo-1-piperidinecarboxylate

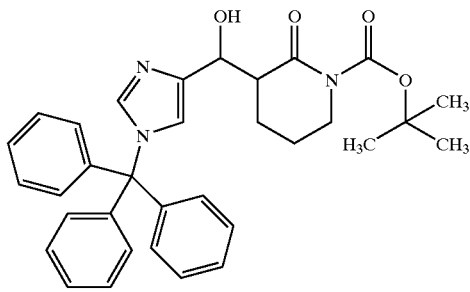

Lithium diisopropylamide (8 ml, 1.5M in cyclohexane, 12 mmol) was added dropwise over 5 minutes to a cooled (−78° C.) solution of tert-butyl 2-oxo-1-piperidinecarboxylate (*J. Org. Chem.* 1983, 48, 2424; *J. Chem. Soc.* I, 1989, 721) (1.99 g, 10 mmol) in tetrahydrofuran (40 ml), so as to maintain a temperature below −70° C. Once addition was complete, the solution was stirred for 20 minutes. A solution of 1-tritylimidazole-4-carboxaldehyde (*J. Med. Chem.* 1977, 20, 721) (4.06 g, 12 mmol) in tetrahydrofuran (60 ml) was added slowly, and once addition was complete, the reaction was stirred at −78° C. for 2 hours. Saturated aqueous ammonium chloride solution (50 ml) was added, the mixture allowed to warm to room temperature and then partitioned between water (50 ml) and ethyl acetate (300 ml). The phases were separated, the organic layer dried (MgSO$_4$), filtered, and concentrated under reduced pressure to give the title compound, 5.3 g, 99% yield.

$^1$H-NMR (CDCl$_3$, 400 MHz) (mixture of diastereoisomers) δ: 1.50 (2×s, 9H), 1.60–1.81 (m, 4H), 3.00 (m, 1H), 3.58 (m, 1H), 3.74 (m, 1H), 4.10, 4.90 (2×m, 1H), 4.62, 5.40 (2×m, 1H), 6.80 (2×s, 1H), 7.14 (m, 6H), 7.25–7.40 (m, 10H).

LMRS: m/z 538 (MH$^+$)

Preparation 101 tert-Butyl (3E)-3-[(1-isopentyl-1H-imidazol-4-yl)methylene]-2-oxo-1-piperidinecarboxylate

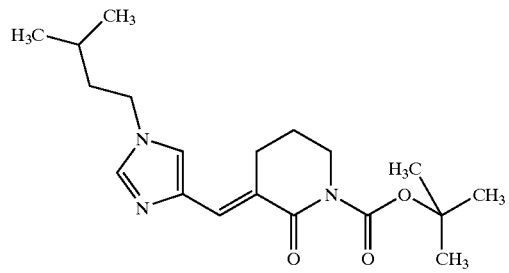

Triethylamine (1.25 ml, 9.0 mmol) and methanesulphonyl chloride (256 μl, 3.3 mmol) were added to a solution of the compound from preparation 97 (1.1 g, 3.0 mmol) in dichloromethane (15 ml), and the reaction stirred at room temperature for 18 hours. The solution was poured into water (200 ml), and extracted with ethyl acetate (300 ml). The organic extract was dried (MgSO$_4$), filtered, and concentrated under reduced pressure. The crude product was purified by column chromatography on silica gel using an elution gradient of pentane:ethyl acetate (25:75 to 0:100) to afford the title compound as a white solid, 430 mg, 41% yield.

$^1$H-NMR (CDCl$_3$, 400 MHz) δ: 0.92 (d, 6H), 1.52 (s, 9H), 1.56 (m, 1H), 1.64 (m, 2H), 1.88 (m, 2H), 3.03 (t, 2H), 3.73 (dd, 2H), 3.92 (t, 2H), 7.05 (s, 1H), 7.45 (s, 1H), 7.62 (s, 1H).

LMRS: m/z 348.1 (MH$^+$)

Anal. Found: C, 65.47; H, 8.49; N, 12.05. C$_{19}$H$_{29}$N$_3$O$_3$ requires C, 65.68; H, 8.41; N, 12.09%.

Preparation 102

(3E)-3-[(1-Isopentyl-1H-imidazol-4-yl)methylene]-1-methyl-2-piperidinone (3Z)-3-[(1-Isopentyl-1H-imidazol-4-yl)methylene]-1-methyl-2-piperidinone

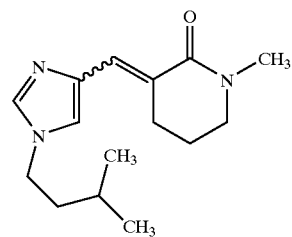

The title compound was obtained as a yellow solid in 46% yield, from the compound from preparation 98, following a similar procedure to that described in preparation 101, except ethyl acetate:diethylamine:methanol (100:0:0 to 96:2:2) was used as the column eluant.

$^1$H-NMR (CDCl$_3$, 400 MHz) δ (mixture of isomers): 0.94 (d, 6H), 1.58 (m, 1H), 1.70 (m, 2H), 1.92 (m, 2H), 3.03 (s, 3H), 3.12 (m, 2H), 3.40 (t, 2H), 3.97 (t, 2H), 7.02 (s, 1H), 7.48 (s, 1H), 7.58 (s, 1H).

LMRS: m/z 262 (MH$^+$)

Preparation 103 tert-Butyl (3E)-2-oxo-3-[(1-trityl-1H-imidazol-4-yl)methylene]-1-piperidinecarboxylate tert-Butyl (3Z)-2-oxo-3-[(1-trityl-1H-imidazol-4-yl)methylene]-1-piperidinecarboxylate

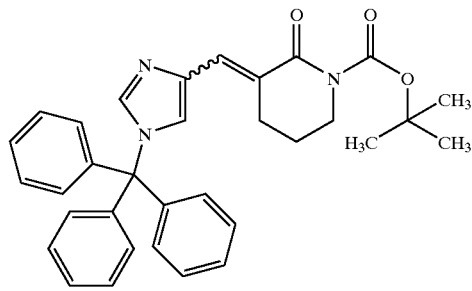

Triethylamine (2.78 ml, 20.0 mmol) and methanesulphonyl chloride (773 µl, 10.0 mmol) were added to an ice-cooled solution of the compound from preparation 100 (5.3 g, 10.0 mmol) in dichloromethane (50 ml), and the reaction stirred at room temperature for 18 hours, and a further 4 hours at reflux. The cooled solution was concentrated under reduced pressure and the residue purified by column chromatography on silica gel using an elution gradient of toluene:ethyl acetate (100:0 to 20:80) to afford the title compound, 2.6 g, 50% yield.

$^1$H-NMR (CDCl$_3$, 400 MHz) δ (mixture of isomers): 1.54 (2×s, 9H), 1.85 (m, 2H), 3.00 (t, 2H), 3.68 (t, 2H), 6.99 (s, 1H), 7.10 (m, 6H), 7.30 (m, 9H), 7.44 (s, 1H), 7.58 (s, 1H).

LMRS: m/z 520.1 (MH$^+$)

Anal. Found: C, 76.40; H, 6.51; N, 7.85. C$_{33}$H$_{33}$N$_3$O$_3$ reqires C, 76.28; H, 6.40; N, 8.09%.

Preparation 104

(2E)-2-{3-[(tert-Butoxycarbonyl)amino]propyl}-3-(1-propyl-1H-imidazol-4-yl)-2-propenoic acid

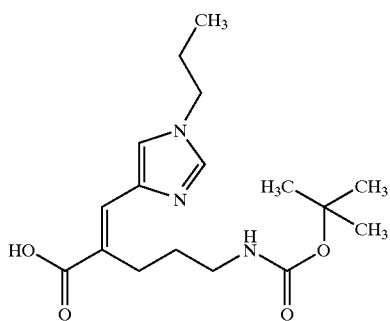

A solution of sodium hydroxide (171.3 g, 4.28M) in water (4.55 L) was added to a solution of the compound from preparation 53 (455 g, 1.42M) in tetrahydrofuran (2.275 L), and the reaction stirred at room temperature for 18 hours. The mixture was concentrated under reduced pressure to remove the tetrahydrofuran and the remaining aqueous solution was adjusted to pH 5 using glacial acetic acid. The resulting precipitate was granulated in an ice-bath for 1 hour, then filtered, washed with water and dried in vacuo. This solid was recrystallized from isopropanol and water to afford the title compound as a white solid, 304 g, 63% yield.

$^1$H-NMR (DMSOd$_6$, 400 MHz) δ: 0.81 (t, 3H), 1.38 (s, 9H), 1.56 (m, 2H), 1.74 (m, 2H), 2.75 (t, 2H), 2.93 (m, 2H), 3.95 (t, 2H), 6.97 (bs, 1H), 7.37 (s, 1H), 7.52 (s, 1H), 7.76 (s, 1H), 12.02 (bs, 1H).

Preparation 105

(±)-tert-Butyl 3-[(1-isopentyl-1H-imidazol-4-yl)methyl]-2-oxo-1-piperidinecarboxylate

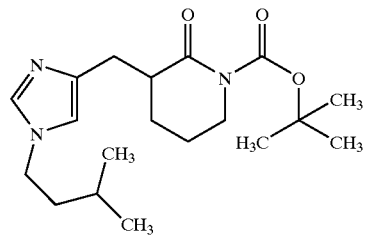

The alkene from preparation 101 (430 mg, 1.25 mmol), and 10% palladium on charcoal (Degussa® 101) (100 mg) in ethanol (10 ml) was hydrogenated at 60 psi and room temperature for 18 hours. The mixture was filtered through Arbocel®, washing through with ethanol. The filtrate was concentrated under reduced pressure to give the title compound as a colorless oil, 420 mg, 97% yield.

$^1$H-NMR (CDCl$_3$, 400 MHz) δ: 0.89 (d, 6H), 1.50 (m, 10H), 1.62 (m, 4H), 1.78 (m, 1H), 1.98 (m, 1H), 2.63 (dd, 1H), 2.77 (m, 1H), 3.15 (dd, 1H), 3.54 (m, 1H), 3.70 (m, 1H), 3.81 (t, 2H), 6.68 (s, 1H), 7.30 (s, 1H).

LMRS: m/z 350 (MH$^+$)

Preparation 106

(±)-3-[(1-Isopentyl-1H-imidazol-4-yl)methyl]-1-methyl-2-piperidinone

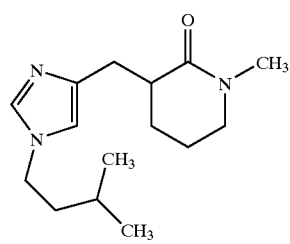

The title compound was obtained as a colorless oil in 24% yield, from the alkenes from preparation 102, following a similar procedure to that described in preparation 105, except the product was additionally purified by column chromatography on silica gel using an elution gradient of ethyl acetate:diethylamine:methanol (100:0:0 to 90:5:5).

$^1$H-NMR (CDCl$_3$, 400 MHz) δ: 0.94 (d, 6H), 1.55 (m, 1H), 1.62 (m, 3H), 1.75 (m, 2H), 1.86 (m, 1H), 2.60 (m, 1H), 2.73 (dd, 1H), 2.94 (s, 3H), 3.22 (m, 3H), 3.85 (t, 2H), 6.69 (s, 1H), 7.35 (s, 1H).

LMRS: m/z 264 (MH$^+$)

Preparation 107

(±)-tert-Butyl 3-(1H-imidazol-4-ylmethyl)-2-oxo-1-piperidinecarboxylate

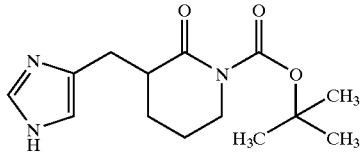

A mixture of the alkenes from preparation 103 (2.4 g, 4.6 mmol) and 10% palladium on charcoal (Degussa® 101) (200 mg) in ethanol (400 ml) was hydrogenated at 50° C. and 60 psi for 18 hours. TLC analysis showed starting material remaining, so additional 10% palladium on charcoal (Degussa® 101) (100 mg) was added, and the mixture hydrogenated for a further 72 hours. The mixture was filtered through Arbocel®, and the filtrate concentrated under reduced pressure. The crude product was purified by column chromatography on silica gel using an elution gradient of dichloromethane:ethyl acetate:methanol (100:0:0 to 0:100:0 to 0:90:10) to afford the title compound as a solid, 1.2 g, 93% yield.

$^1$H-NMR (CDCl$_3$, 400 MHz) δ: 1.46–1.62 (m, 10H), 1.81 (m, 2H), 1.98 (m, 1H), 2.66 (m, 1H), 2.95 (m, 2H), 3.55 (m, 1H), 3.78 (m, 1H), 6.80 (s, 1H), 7.24 (s, 1H), 7.50 (s, 1H).

LMRS: m/z 280 (MH$^+$)

Preparation 108

(±)-tert-Butyl 2-oxo-3-[(1-phenyl-1H-imidazol-4-yl)methyl]-1-piperidine-carboxylate

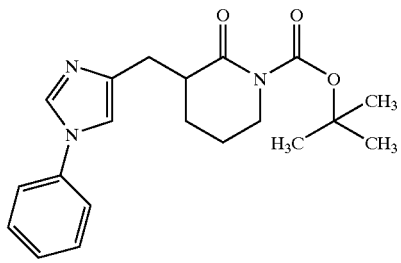

Phenylboronic acid (366 mg, 3 mmol), 4 Å molecular sieves (1 g), copper acetate (408 mg, 2.25 mmol) and pyridine (243 μl, 3 mmol) were added to a solution of the imidazole from preparation 107 (419 mg, 1.5 mmol) in dichloromethane (10 ml), and the reaction mixture stirred at room temperature for 4 hours in the presence of a slow stream of compressed air. The air flow was then stopped, and the reaction was stirred for a further 18 hours at room temperature. A solution of ethylenediaminetetraacetic acid (2 g) in aqueous sodium bicarbonate solution (10 ml) was added, the mixture stirred for 10 minutes, then diluted with dichloromethane (100 ml). The layers were separated, the organic phase dried (MgSO$_4$) and concentrated under reduced pressure. The residue was purified by column chromatography on silica gel using an elution gradient of ethyl acetate:pentane (50:50 to 80:20) to afford the title compound as a gum, 253 mg, 47% yield.

$^1$H-NMR (CDCl$_3$, 400 MHz) δ: 1.52 (s, 9H), 1.81 (m, 2H), 2.05 (m, 1H), 2.78–2.90 (m, 2H), 3.22 (dd, 1H), 3.58 (m, 1H), 3.77 (m, 2H), 7.11 (s, 1H), 7.36 (m, 3H), 7.42 (m, 2H), 7.77 (s, 1H).

LMRS: m/z 356.1 (MH$^+$)

Preparation 109

(±)-5-[(tert-Butoxycarbonyl)amino]-2-[(1-propyl-1H-imidazol-4-yl)methyl]pentanoic acid

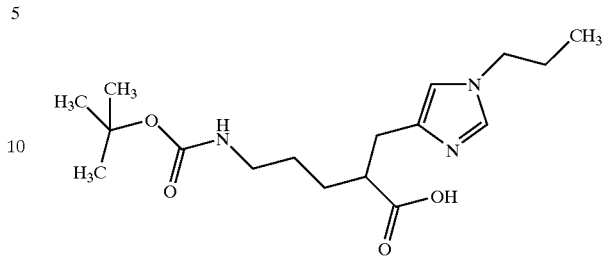

A mixture of the compound from preparation 104 (302 g, 0.895M) and 5% palladium on charcoal (30 g) in ethanol (3.0 L) was hydrogenated at 60 psi and 60° C. for 18 hours. The cooled reaction was filtered through Arbocel® and the filtrate evaporated under reduced pressure to give a colorless oil. This was crystallized from ethyl acetate and pentane, to afford the title compound as a white solid, 291.7 g, 96% yield.

$^1$H-NMR (CDCl$_3$, 300 MHz) δ: 0.90 (t, 3H), 1.42 (m, 10H), 1.58 (m, 2H), 1.66–1.86 (m, 3H), 2.70 (m, 1H), 2.83 (d, 2H), 3.10 (m, 2H), 3.84 (t, 2H), 4.63 (bs, 1H), 6.68 (s, 1H), 7.49 (s, 1H).

Preparation 110

(2S)-5-[(tert-Butoxycarbonyl)amino]-2-[(1-propyl-1H-imidazol-4-yl)methyl]pentanoic acid with quinidine

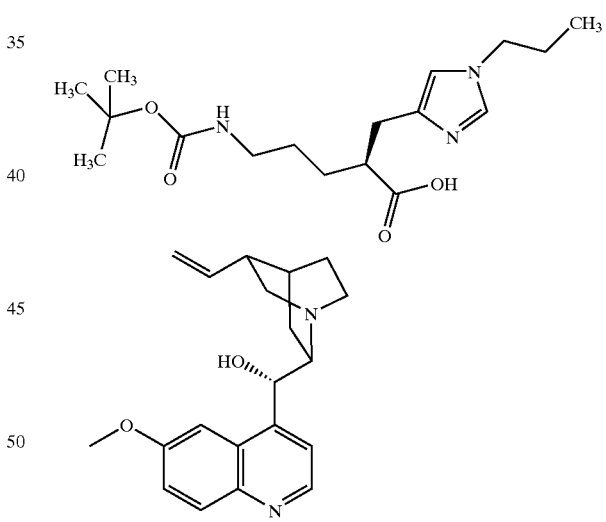

A mixture of the acid from preparation 104 (20 g, 59 mmol), quinidine (19.23 g, 59 mmol) and methanol (160 ml) in a pressure vessel was purged with nitrogen, and then hydrogen to a pressure of 3 psi. The vessel was heated to 60° C., a solution of [(R)-iPrFerroLANE Rh(COD)]BF$_4$ (Chirotech Technology Limited) (9.8 mg, 0.012 mmol) in deoxygenated methanol (1 ml) was added, and the reaction mixture hydrogenated at 145 psi for 40 hours. The cooled solution was concentrated under reduced pressure and the crude product dissolved in ethyl acetate, with warming to 60° C. On cooling to room temperature with stirring, precipitation occurred, and the solid was filtered and dried in vacuo to afford the title compound, 29.8 g, 76% yield (94% ee determined by CE).

Alternative Method of Synthesis for Title Compound in Preparation 110

A mixture of the acid from preparation 109 (50 g, 147 mmol) and quinidine (47.8 g, 147 mmol) in ethyl acetate (1.75L) was heated at 50° C. on a steam bath, until a solution was obtained. The solution was warmed to 60° C., the heat removed and the solution allowed to cool, then stirred at room temperature for 18 hours. The resulting precipitate was filtered, washed with ethyl acetate and dried at 80° C. in vacuo to afford the title compound as a white solid, 45.1 g, 46% yield.

$^1$H-NMR (CD$_3$OD, 400 MHz) δ: 0.83 (t, 3H), 1.10–1.20 (m, 1H), 1.40 (s, 9H), 1.45–1.62 (m, 5H), 1.65–1.80 (m, 4H), 1.88 (m, 1H), 2.37 (m, 1H), 2.50–2.64 (m, 3H), 2.84 (m, 1H), 3.00–3.14 (m, 3H), 2.21 (m, 1H), 3.39 (m, 1H), 3.80 (m, 2H), 3.96 (m, 4H), 5.17–5.25 (m, 2H), 5.91 (m, 1H), 6.07–6.18 (m, 1H), 6.89 (s, 1H), 7.38 (d, 1H), 7.43 (dd, 1H), 7.57 (s, 1H), 7.76 (d, 1H), 7.98 (d, 1H), 8.72 (d, 1H).

LMRS: m/z 340 (MH$^+$), 325 (quinidineH$^+$)

Anal. Found: C, 65.82; H, 8.17; N, 10.32. C$_{37}$H$_{53}$N$_5$O$_6$·0.5H$_2$O requires 66.05; H, 8.09; N, 10.41%.

$[α]_D$=+121.36 (c 0.15, methanol

We claim:

1. A compound of formula (I)

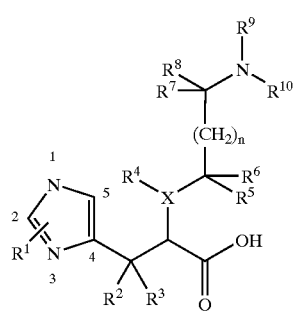

(I)

wherein

X is CH;

n is 0, 1, 2 or 3;

R$^1$ is hydrogen, heterocycle, aromatic heterocycle, aryl, (C$_1$–C$_6$)alkyl, (C$_2$–C$_6$)alkenyl, or (C$_2$–C$_6$)alkynyl, where each of (C$_1$–C$_6$)alkyl, (C$_2$–C$_6$)alkenyl, and (C$_2$–C$_6$)alkynyl are optionally substituted by (C$_3$–C$_7$)cycloalkyl, aryl, aromatic heterocycle, heterocycle, OR$^{11}$, NR$^{11}$R$^{12}$, S(O)$_p$R$^{11}$, OC(O)R$^{11}$, CO$_2$R$^{11}$, CONR$^{11}$R$^{12}$, SO$_2$NR$^{11}$R$^{12}$, halo or NHSO$_2$R$^{11}$, where p is 0, 1 or 2, and R$^{11}$ and R$^{12}$ are each independently hydrogen, (C$_1$–C$_6$)alkyl, or when forming a NR$^{11}$R$^{12}$ moiety, R$^{11}$ and R$^{12}$ is optionally taken together to form a (C$_2$–C$_6$)alkylene linkage;

R$^2$ and R$^3$ are each independently hydrogen, (C$_1$–C$_6$)alkyl optionally substituted by OR$^{11}$ or halo, or R$^2$ and R$^3$ taken together form a (C$_2$–C$_6$)alkylene linkage;

R$^4$ is hydrogen, (C$_1$–C$_6$)alkyl optionally substituted by (C$_3$–C$_7$)cycloalkyl, aryl, OR$^{11}$, halo or R$^{11}$, or R$^4$ taken together with R$^{10}$ forms a (C$_1$–C$_4$)alkylene linkage optionally substituted by halo, OR$^{11}$, or R$^{11}$, where R$^{11}$ is hydrogen or (C$_1$–C$_6$)alkyl;

R$^5$ and R$^6$ are each independently hydrogen, aryl, (C$_1$–C$_6$) alkyl optionally substituted by (C$_3$–C$_7$)cycloalkyl, aromatic heterocycle, heterocycle, aryl, OR$^{11}$, R$^{11}$ or halo, R$^5$ or R$^6$ taken together with R$^{10}$ forms a (C$_1$–C$_3$) alkylene optionally substituted by OR$^{11}$, halo, R$^{11}$, or aryl, or R$^5$ and R$^6$ taken together form a (C$_2$–C$_6$) alkylene linkage, where R$^{11}$ is hydrogen or (C$_1$–C$_6$) alkyl;

R$^7$ and R$^8$ are each independently hydrogen, (C$_1$–C$_6$)alkyl optionally substituted by OR$^{11}$, halo, aryl, or R$^{11}$, or R$^7$ and R$^8$ taken together form a (C$_2$–C$_6$)alkylene linkage, where R$^{11}$ is hydrogen or (C$_1$–C$_6$)alkyl; and R$^9$ and R$^{10}$ are each independently hydrogen, C(NR$^{11}$) NR$^{11}$R$^{12}$, (C$_1$–C$_6$)alkyl optionally substituted by OR$^{11}$, halo, aryl, or R$^{11}$, where R$^{11}$ and R$^{12}$ are each independently hydrogen or (C$_1$–C$_6$)alkyl, or R$^9$ and R$^{10}$ taken together form a (C$_2$–C$_6$)alkylene linkage;

a pharmaceutically acceptable salt thereof, a prodrug of said compound or said salt, or a solvate of said compound, said salt, or said prodrug.

2. The compound of claim 1, a pharmaceutically acceptable salt thereof, a prodrug of said compound or said salt, or a solvate of said compound, said salt or said prodrug, wherein said compound of formula (I) has the stereochemistry represented by formulae (IA) or (IB)

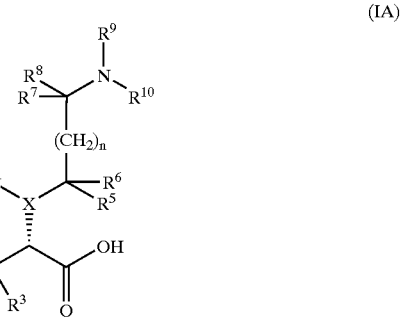

(IA)

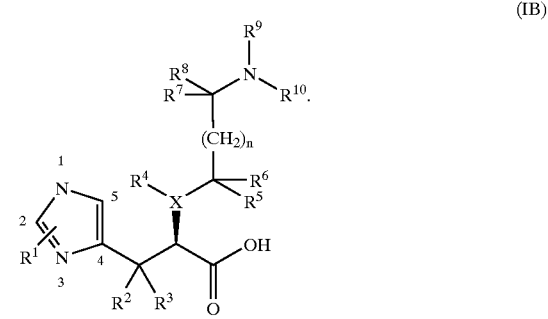

(IB)

3. The compound of claim 1, a pharmaceutically acceptable salt thereof, a prodrug of said compound or said salt, or a solvate of said compound, said salt or said prodrug, wherein said compound of formula (I) has the stereochemistry represented by formulae (IA)

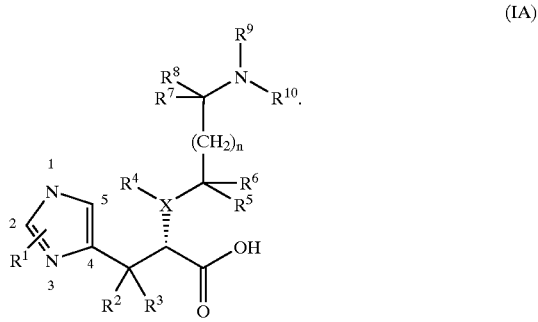

(IA)

4. The compound of claim 1 wherein the imidazole ring of said compound of formula (I) is 1,4 disubstituted where said R$^1$ group is attached to N1;

a pharmaceutically acceptable salt thereof, a prodrug of said compound or said salt, or a solvate of said compound, said salt, or said prodrug.

5. The compound of claim 1, 2, 3 or 4 wherein $R^1$ is an aryl group, $(C_2-C_6)$alkenyl group, or a $(C_2-C_6)$alkyl group optionally substituted by one or more groups selected from the group consisting of $CO_2R^{11}$, $OR^{11}$, aryl, $(C_3-C_7)$ cycloalkyl, $NHSO_2R^{11}$, halo and aromatic heterocycle;

a pharmaceutically acceptable salt thereof, a prodrug of said compound or said salt, or a solvate of said compound, said salt or said prodrug.

6. The compound of claim 5, wherein $R^1$ is $(C_1-C_3)$alkyl;

a pharmaceutically acceptable salt thereof, a prodrug of said compound or said salt, or a solvate of said compound, said salt, or said prodrug.

7. The compound of claim 1, 2, 3 or 4 wherein $R^2$ and $R^3$ are each hydrogen;

a pharmaceutically acceptable salt thereof, a prodrug of said compound or said salt, or a solvate of said compound, said salt, or said prodrug.

8. The compound of claim 1, 2, 3 or 4 wherein $R^4$ is hydrogen, $(C_1-C_3)$alkyl, or taken together with $R^{10}$ forms a $(C_2-C_3)$alkylene linkage;

a pharmaceutically acceptable salt thereof, a prodrug of said compound or said salt, or a solvate of said compound, said salt, or said prodrug.

9. The compound of claim 8 wherein $R^4$ is hydrogen;

a pharmaceutically acceptable salt thereof, a prodrug of said compound or said salt, or a solvate of said compound, said salt, or said prodrug.

10. The compound of claim 1, 2, 3 or 4 wherein $R^5$ and $R^6$ are each independently hydrogen, $(C_1-C_6)$alkyl optionally substituted by phenyl, or $R^5$ taken together with $R^{10}$ forms a $(C_1-C_3)$alkylene linkage;

a pharmaceutically acceptable salt thereof, a prodrug of said compound or said salt, or a solvate of said compound, said salt, or said prodrug.

11. The compound of claim 10 wherein $R^5$ and $R^6$ are each independently hydrogen, $(C_1-C_6)$alkyl optionally substituted by phenyl, or $R^5$ taken together with $R^6$ forms a $(C_1-C_3)$alkylene linkage;

a pharmaceutically acceptable salt thereof, a prodrug of said compound or said salt, or a solvate of said compound, said salt, or said prodrug.

12. The compound of claim 10 wherein $R^5$ and $R^6$ are each hydrogen;

a pharmaceutically acceptable salt thereof, a prodrug of said compound or said salt, or a solvate of said compound, said salt, or said prodrug.

13. The compound of claim 1, 2, 3 or 4 wherein $R^7$ and $R^8$ are each independently hydrogen or $(C_1-C_6)$alkyl;

a pharmaceutically acceptable salt thereof, a prodrug of said compound or said salt, or a solvate of said compound, said salt, or said prodrug.

14. The compound of claim 13 wherein $R^7$ and $R^8$ are each hydrogen;

a pharmaceutically acceptable salt thereof, a prodrug of said compound or said salt, or a solvate of said compound, said salt, or said prodrug.

15. The compound of claim 1, 2, 3 or 4 wherein $R^9$ and $R^{10}$ are each independently hydrogen, $(C_1-C_3)$alkyl, or $R^{10}$ taken together with $R^4$ forms a $(C_2-C_3)$alkylene;

a pharmaceutically acceptable salt thereof, a prodrug of said compound or said salt, or a solvate of said compound, said salt, or said prodrug.

16. The compound of claim 15 wherein $R^9$ and $R^{10}$ are each hydrogen;

a pharmaceutically acceptable salt thereof, a prodrug of said compound or said salt, or a solvate of said compound, said salt, or said prodrug.

17. The compound of claim 1, 2, 3 or 4 wherein $R^{11}$ and $R^{12}$ are each independently hydrogen or $(C_1-C_6)$alkyl;

a pharmaceutically acceptable salt thereof, a prodrug of said compound or said salt, or a solvate of said compound, said salt, or said prodrug.

18. The compound of claim 17 wherein $R^{11}$ and $R^{12}$ are each independently hydrogen or $CH_3$;

a pharmaceutically acceptable salt thereof, a prodrug of said compound or said salt, or a solvate of said compound, said salt, or said prodrug.

19. The compound of claim 1, 2, 3 or 4 wherein n is 0;

a pharmaceutically acceptable salt thereof, a prodrug of said compound or said salt, or a solvate of said compound, said salt, or said prodrug.

20. The compound of claim 1, 2, 3 or 4 wherein

X is CH;

n is 0;

$R^1$ is $(C_1-C_3)$alkyl;

$R^2$ and $R^3$ are each hydrogen;

$R^4$ is hydrogen;

$R^5$ and $R^6$ are each hydrogen;

$R^7$ and $R^8$ are each hydrogen;

$R^9$ and $R^{10}$ are each hydrogen;

$R^{11}$ and $R^{12}$ are each independently hydrogen or $CH_3$;

a pharmaceutically acceptable salt thereof, a prodrug of said compound or said salt, or a solvate of said compound, said salt, or said prodrug.

21. The compound of claim 1 wherein said compound is selected from the group consisting of:

(±)-5-amino-2-[(1-n-propyl-1H-imidazol-4-yl)methyl] pentanoic acid;

(+)-(2S)-5-amino-2-[(1-n-butyl-1H-imidazol-4-yl) methyl]pentanoic acid;

(+)-(2S)-5-amino-2-[(1-n-propyl-1H-imidazol-4-yl) methyl]pentanoic acid; and (+)-(2S)-5-amino-2-(1H-imidazol-4-ylmethyl)pentanoic acid;

a pharmaceutically acceptable salt thereof, a prodrug of said compound or said salt, or a solvate of said compound, said salt, or said prodrug.

22. The compound of claim 21 wherein said compound is (+)-(2S)-5-amino-2-[(1-n-propyl-1H-imidazol-4-yl)methyl] pentanoic acid;

a pharmaceutically acceptable salt thereof, a prodrug of said compound or said salt, or a solvate of said compound, said salt, or said prodrug.

23. A compound of formula (II)

(II)

wherein

X is CH;

n is 0, 1, 2 or 3;

$R^1$ is hydrogen, heterocycle, aromatic heterocycle, aryl, $(C_1-C_6)$alkyl, $(C_2-C_6)$alkenyl, or $(C_2-C_6)$alkynyl, where each of $(C_1-C_6)$alkyl, $(C_2-C_6)$alkenyl, and ($C_2$–$C_6$)alkynyl are optionally substituted by ($C_3$–$C_7$) cycloalkyl, aryl, aromatic heterocycle, heterocycle, $OR^{11}$, $NR^{11}R^{12}$, $S(O)_pR^{11}$, $OC(O)R^{11}$, $CO_2R^{11}$, $CONR^{11}R^{12}$, $SO_2NR^{11}R^{12}$, halo or $NHSO_2R^{11}$, where p is 0, 1 or 2, and $R^{11}$ and $R^{12}$ are each independently hydrogen, ($C_1$–$C_6$)alkyl, or when forming a $NR^{11}R^{12}$ moiety, $R^{11}$ and $R^{12}$ is optionally taken together to form a ($C_2$–$C_6$)alkylene linkage;

$R^2$ and $R^3$ are each independently hydrogen, ($C_1$–$C_6$)alkyl optionally substituted by $OR^{11}$ or halo, or $R^2$ and $R^3$ taken together form a ($C_2$–$C_6$)alkylene linkage;

$R^4$ is hydrogen, ($C_1$–$C_6$)alkyl optionally substituted by ($C_3$–$C_7$)cycloalkyl, aryl, $OR^{11}$, halo or $R^{11}$, or $R^4$ taken together with $R^{10}$ forms a ($C_2$–$C_4$)alkylene linkage optionally substituted by halo, $OR^{11}$, or $R^{11}$, where $R^{11}$ is hydrogen or ($C_1$–$C_6$)alkyl;

$R^5$ and $R^6$ are each independently hydrogen, aryl, ($C_1$–$C_6$) alkyl optionally substituted by ($C_3$–$C_7$)cycloalkyl, aromatic heterocycle, heterocycle, aryl, $OR^{11}$, $R^{11}$ or halo, $R^5$ or $R^6$ taken together with $R^{10}$ forms a ($C_1$–$C_3$) alkylene optionally substituted by $OR^{11}$, halo, $R^{11}$, or aryl, or $R^5$ and $R^6$ taken together form a ($C_2$–$C_6$) alkylene linkage, where $R^{11}$ is hydrogen or ($C_1$–$C_6$) alkyl;

$R^7$ and $R^8$ are each independently hydrogen, ($C_1$–$C_6$)alkyl optionally substituted by $OR^{11}$, halo, aryl, or $R^{11}$, or $R^7$ and $R^8$ taken together form a ($C_2$–$C_6$)alkylene linkage, where $R^{11}$ is hydrogen or ($C_1$–$C_6$)alkyl; and $R^9$ and $R^{10}$ are each independently hydrogen, a nitrogen-protecting group, $C(NR^{11})NR^{11}R^{12}$, ($C_1$–$C_6$)alkyl optionally substituted by $OR^{11}$, halo, aryl, or $R^{11}$, where $R^{11}$ and $R^{12}$ are each independently hydrogen or ($C_1$–$C_6$)alkyl, or $R^9$ and $R^{10}$ taken together form a ($C_2$–$C_6$)alkylene linkage; and $R^{13}$ is an oxygen-protecting group.

24. A pharmaceutical composition comprising:

(i) a compound of formula (I)

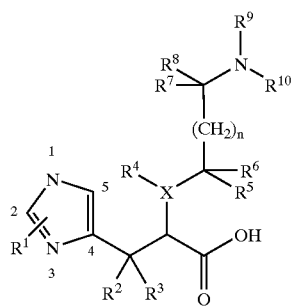

(I)

wherein

X is CH;

n is 0, 1, 2 or 3;

$R^1$ is hydrogen, heterocycle, aromatic heterocycle, aryl, ($C_1$–$C_6$)alkyl, ($C_2$–$C_6$)alkenyl, or ($C_2$–$C_6$)alkynyl, where each of ($C_1$–$C_6$)alkyl, ($C_2$–$C_6$)alkenyl, and ($C_2$–$C_6$)alkynyl are optionally substituted by ($C_3$–$C_7$) cycloalkyl, aryl, aromatic heterocycle, heterocycle, $OR^{11}$, $NR^{11}R^{12}$, $S(O)_pR^{11}$, $OC(O)R^{11}$, $CO_2R^{11}$, $CONR^{11}R^{12}$, $SO_2NR^{11}R^{12}$, halo or $NHSO_2R^{11}$, where p is 0, 1 or 2, and $R^{11}$ and $R^{12}$ are each independently hydrogen, ($C_1$–$C_6$)alkyl, or when forming a $NR^{11}R^{12}$ moiety, $R^{11}$ and $R^{12}$ is optionally taken together to form a ($C_2$–$C_6$)alkylene linkage;

$R^2$ and $R^3$ are each independently hydrogen, ($C_1$–$C_6$)alkyl optionally substituted by $OR^{11}$ or halo, or $R^2$ and $R^3$ taken together form a ($C_2$–$C_6$)alkylene linkage;

$R^4$ is hydrogen, ($C_1$–$C_6$)alkyl optionally substituted by ($C_3$–$C_7$)cycloalkyl, aryl, $OR^{11}$, halo or $R^{11}$, or $R^4$ taken together with $R^{10}$ forms a ($C_2$–$C_4$)alkylene linkage optionally substituted by halo, $OR^{11}$, or $R^{11}$, where $R^{11}$ is hydrogen or ($C_1$–$C_6$)alkyl;

$R^5$ and $R^6$ are each independently hydrogen, aryl, ($C_1$–$C_6$) alkyl optionally substituted by ($C_3$–$C_7$)cycloalkyl, aromatic heterocycle, heterocycle, aryl, $OR^{11}$, $R^{11}$ or halo, $R^5$ or $R^6$ taken together with $R^{10}$ forms a ($C_2$–$C_3$) alkylene optionally substituted by $OR^{11}$, halo, $R^{11}$, or aryl, or $R^5$ and $R^6$ taken together form a ($C_2$–$C_6$) alkylene linkage, where $R^{11}$ is hydrogen or ($C_1$–$C_6$) alkyl;

$R^7$ and $R^8$ are each independently hydrogen, ($C_1$–$C_6$)alkyl optionally substituted by $OR^{11}$, halo, aryl, or $R^{11}$, or $R^7$ and $R^8$ taken together form a ($C_2$–$C_6$)alkylene linkage, where $R^{11}$ is hydrogen or ($C_1$–$C_6$)alkyl; and $R^9$ and $R^{10}$ are each independently hydrogen, $C(NR^{11})$ $NR^{11}R^{12}$, ($C_1$–$C_6$)alkyl optionally substituted by $OR^{11}$, halo, aryl, or $R^{11}$, where $R^{11}$ and $R^{12}$ are each independently hydrogen or ($C_1$–$C_6$)alkyl, or $R^9$ and $R^{10}$ taken together form a ($C_2$–$C_6$)alkylene linkage;

a pharmaceutically acceptable salt thereof, a prodrug of said compound or said salt, or a solvate of said compound, said salt, or said prodrug; and (ii) a pharmaceutically acceptable excipient, diluent or carrier.

* * * * *